United States Patent
Walensky et al.

(10) Patent No.: US 11,078,246 B2
(45) Date of Patent: Aug. 3, 2021

(54) PEPTIDES BINDING TO BFL-1

(71) Applicant: Dana-Farber Cancer Institute, Inc., Boston, MA (US)

(72) Inventors: Loren D. Walensky, Newton, MA (US); Gregory H. Bird, Pelham, NH (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 87 days.

(21) Appl. No.: 15/752,358

(22) PCT Filed: Aug. 26, 2016

(86) PCT No.: PCT/US2016/049095
§ 371 (c)(1),
(2) Date: Feb. 13, 2018

(87) PCT Pub. No.: WO2017/040329
PCT Pub. Date: Mar. 9, 2017

(65) Prior Publication Data
US 2019/0002514 A1  Jan. 3, 2019

Related U.S. Application Data

(60) Provisional application No. 62/211,680, filed on Aug. 28, 2015.

(51) Int. Cl.
| | | |
|---|---|---|
| *A61K 38/17* | (2006.01) |
| *C07K 14/47* | (2006.01) |
| *A61K 47/54* | (2017.01) |
| *A61P 35/00* | (2006.01) |
| *A61K 45/06* | (2006.01) |
| *C12Q 1/6886* | (2018.01) |
| *A61K 38/00* | (2006.01) |

(52) U.S. Cl.
CPC ...... *C07K 14/4747* (2013.01); *A61K 38/1761* (2013.01); *A61K 45/06* (2013.01); *A61K 47/545* (2017.08); *A61P 35/00* (2018.01); *C12Q 1/6886* (2013.01); *A61K 38/00* (2013.01); *C12Q 2600/106* (2013.01)

(58) Field of Classification Search
CPC ............ A61K 38/1709; A61K 38/1761; C07K 14/4747; C07K 14/47
See application file for complete search history.

(56) References Cited

U.S. PATENT DOCUMENTS

| | | | |
|---|---|---|---|
| 5,446,090 A | 8/1995 | Harris | |
| 6,348,558 B1 | 2/2002 | Harris et al. | |
| 7,723,468 B2 | 5/2010 | Daffre et al. | |
| 8,889,632 B2 | 11/2014 | Bernal et al. | |
| 9,464,125 B2 * | 10/2016 | Link | A61K 38/12 |
| 9,493,510 B2 | 11/2016 | Skerlj | |
| 10,023,613 B2 * | 7/2018 | Guerlavais | C07K 14/4702 |
| 2004/0093164 A1 | 5/2004 | Carlson et al. | |
| 2005/0250680 A1 | 11/2005 | Walensky | |
| 2009/0048164 A1 | 2/2009 | Colman et al. | |
| 2010/0168388 A1 | 7/2010 | Bernal et al. | |
| 2010/0286057 A1 * | 11/2010 | Walensky | C07K 14/4747 514/18.9 |
| 2012/0172285 A1 | 7/2012 | Walensky et al. | |
| 2014/0296160 A1 | 9/2014 | Walensky et al. | |
| 2014/0370042 A1 | 12/2014 | Walensky et al. | |
| 2015/0051249 A1 * | 2/2015 | Walensky | A61K 31/426 514/326 |
| 2015/0119551 A1 | 4/2015 | Bernal et al. | |
| 2019/0002506 A1 | 1/2019 | Walensky et al. | |

FOREIGN PATENT DOCUMENTS

| | | |
|---|---|---|
| JP | 2008-509378 | 3/2008 |
| JP | 2012-511512 | 5/2012 |
| JP | 2015-504064 A | 2/2015 |
| WO | WO 1999/14259 | 3/1999 |
| WO | WO 1999/34833 | 7/1999 |
| WO | WO 2005/075645 | 8/2005 |
| WO | WO 2008/121767 | 10/2008 |
| WO | WO 2009/108261 | 9/2009 |
| WO | WO 2010/060112 | 5/2010 |
| WO | WO 2010/068684 | 6/2010 |
| WO | WO 2010/148335 | 12/2010 |
| WO | 2014/110420 | 7/2014 |
| WO | WO 2014/151369 | 9/2014 |
| WO | WO 2017/040323 | 3/2017 |
| WO | WO 2017/040329 | 3/2017 |
| WO | WO 2019/118719 | 6/2019 |

OTHER PUBLICATIONS

Ali et al. Stapled peptide inhibitors: a new window for target drug discovery. Computational Structural Biotechnol J 17: 263-281, 2019.*
Baggio et al. N-locking stabilization of current helical peptides: applicat6ion to Bfl-1 antagonists. Chem Biol Drug Design 00: 1-15, 2020.*
Barile et al. hBfl-1/hNOXA interaction studies provide new insights on the role of Bfl-1 in cancer cell resistance and for the design of novel anticancer agents. ACS Chem Biol 12: 444-455, 2017.*
Bork, P. Powers and pitfalls in sequence analysis: the 70% hurdle. Genome Res 10: 398-400, 2000.*
Bork, P. Go hunting in sequence databases but watch out for the traps. Trends in Genetics 12(10): 425-427, 1996.*
Brenner. S.E. Errors in genome annotation. Trends in Genetics 15:132-133, 1999.*
Chonghaile et al. Mimicking the BH3 domain to kill cancer cells. Oncogene 27: S149-S157, 2009.*
Doerks et al. Protein annotation: detective work for function prediction. Trends in Genetics 14:248-250, 1998.*
Harvey et al. Crystal structures of anti-apoptotic Bfl-1 and its complex with a covalent stapled peptide inhibitor. Structure 26: 153-160, 2018.*

(Continued)

*Primary Examiner* — Bridget E Bunner
(74) *Attorney, Agent, or Firm* — Fish & Richardson P.C.

(57) ABSTRACT

This disclosure features stapled peptide inhibitors (e.g., cysteine-reactive stapled peptides) of the anti-apoptotic protein, BFL-1, and methods of using same in the treatment of BFL-1 expressing cancers.

76 Claims, 31 Drawing Sheets

Specification includes a Sequence Listing.

(56) References Cited

OTHER PUBLICATIONS

LaBelle et al. A stapled BIM peptide overcomes apoptotic resistance in hematologic cancers. J Clin Invest 122(6): 2018-2031, 2012.*
Ngo et al. "Computational complexity, protein structure prediction, and the Levinthal paradox" in The Protein Folding Problem and Tertiary Structure Prediction, pp. 492-495, 1994.*
Skolnick et al. From genes to protein structure and function: novel applications of computational approaches in the genomic era. Trends Biotechnol 18(I):34-39 2000.*
Smith et al. The challenges of genome sequence annotation or "the devil is in the details". Nature Biotechnol 15: 1222-1223, 1997.*
Tokuriki et al. Stability effects of mutations and protein evolvability. Curr Opin Structural Biol 19: 596-604, 2009.*
Wells, J.A. Additivity of mutational effects in proteins. Biochemistry 29(37): 8509-8517, 1990.*
Altschul et al. Gapped BLAST and PSI-BLAST: a new generation of protein database search programs, Nucleic Acids Res. 25(17):3389-3402, 1997.
Bang, et al., Total Chemical Synthesis of Crambin, J. Am. Chem. Soc. 126:1377-1383, 2004.
Bird et al., Biophysical determinants for cellular uptake of hydrocarbon-stapled peptide helices, Nat Chem Biol. 12(10):845-52, 2016.
Bird et al., Chemical Synthesis of Hydrocarbon-Stapled Peptides for Protein Interaction Research and Therapeutic Targeting, Curr. Protoc. Chem. Biol., 3:99-117 2011.
Bird et. al., Synthesis and Biophysical Characterization of Stabilized alpha-Helices of BCL-2 Domains, Methods in Enzymol., 446:369-386 2008.
Blackwell et al., Ring-Closing Metathesis of Olefinic Peptides: Design, Synthesis, and Structural Characterization of Macrocyclic Helical Peptides, J. Org. Chem., 66: 5291-5302, 2001.
Devi et al., Antibodies to poly [(28)-a-N-acetylneuraminic acid] and poly [(2 9)-a-N-acetylneuraminic acid] are elicited by immunization of mice with Escherichia coli K92 conjugates: Potential vaccines for groups B and C meningococci and E. coli K1, Proc. Natl. Acad. Sci. USA 88:7175-7179, 1991.
Fattom et al., Serum Antibody Response in Adult Volunteers Elicited by Injection of Streptococcus pneumoniae Type 12F Polysaccharide Alone or Conjugated to Diphtheria Toxoid, Infect. Immun., 58(7):2309-2312, 1990.
Fields et al., Chapter 3 in Synthetic Peptides: A User's Guide, ed. Grant, W. H. Freeman & Co., New York, N.Y., 1992, p. 77-183.
Haq et al., BCL2A1 is a lineage-specific antiapoptotic melanoma oncogene that confers resistance to BRAF inhibition, Proc Natl Acad Sci U S A 110(11):4321-4326 2013.
Kawamoto et al. Design of Triazole-stapled BCL9 α-Helical Peptides to Target the β-Catenin/B-cell CLL/lymphoma 9 (BCL9) Protein-Protein Interaction, Journal of Medicinal Chemistry 55(3):1137-1146, 2012.
Leshchiner et al., Direct activation of full-length proapoptotic BAK, Proc Natl Acad Sci U S A. 110(11):E986-95, 2013.
Li et al., Comparative Immunogenicities of Vi Polysaccharide-Protein Conjugates Composed of Cholera Toxin or Its B Subunit as a Carrier Bound to High- or Lower-Molecular-Weight Vi, Infect. Immun. 57(12):3823-3827, 1989.
Lovell et al., Membrane Binding by tBid Initiates an Ordered Series of Events Culminating in Membrane Permeabilization by Bax, Cell 135, 1074-1084, 2008.
Pitter et al., Dissection of the BCL-2 Family Signaling Network with Stabilized a-Helices of BCL-2 Domains, Methods Enzymol., 446, 387-408 2008.
Schafmeister et al., An All-Hydrocarbon Cross-Linking System for Enhancing the Helicity and Metabolic Stability of Peptides, J. Am. Chem. Soc., 122:5891-5892 2000.
Szu et al., Vi Capsular Pol Ysaccharide-Protein Conjugates for Prevention of Typhoid Fever Preparation, Characterization, and Immunogenicity in Laboratory Animals, J. Exp. Med. 166:1510-1524, 1987.
Szu et al., Relation between Structure and Immunologic Properties of the Vi Capsular Polysaccharide, Infect. Immun. 59(12):4555-4561,1991.
Szu et al., Laboratory and Preliminary Clinical Characterization of Vi Capsular Polysaccharide-Protein Conjugate Vaccines, Infect. Immun. 62(10):4440-4444, 1994.
Walensky et al., Activation of Apoptosis in Vivo by a Hydrocarbon-Stapled BH3 Helix, Science, 305(5689):1466-1470 2004.
Wilen, S. H., et al., Strategies in Optical Resolutions, Tetrahedron 33:2725, 1977.
Wilen, S. H. Tables of Resolving Agents and Optical Resolutions, EX. Eliel, Ed., Univ. of Notre Dame Press, Notre Dame, IN, 1972, pp. 268-308.
Williams et al. Asymmetric Synthesis of Monosubstituted and α,α-Disubstituted α-Amino Acids via Diastereoselective Glycine Enolate Alkylation, J. Am. Chem. Soc., 113:9276-9286, 1991.
Williams et al., Efficient Asymmetric Synthesis of N-tert-Butoxycarbonyl alpha-Aminoacids Using 4-tert-Butoxycarbonyl-5,6-Diphenylmorpholin-2-ONE: (R)-(N-tert-Butoxycarbonyl)Allylglycine [(4-Pentenoic acid, 2-[[(1,1-dimethylethoxy)carbonyl]amino]-, (2R)-)], Org. Synth., 80:31-37, 2003.
Yang et al., Calculation of Protein Conformation from Circular Dichroism, Methods Enzymol. 130:208-269 1986.
ISA/US, International Search Report and Written Opinion for PCT/US2016/049083 (dated Feb. 16, 2017) (19 pp).
ISA/US, International Preliminary Report on Patentability for PCT/US2016/049095 dated Mar. 6, 2018 (12 pages).
ISA/US, International Preliminary Report on Patentability for PCT/US2016/049083 dated Mar. 6, 2018 (13 pages).
ISA/US, International Search Report and Written Opinion issued for PCT/US2016/049095 (dated Feb. 21, 2017) (17 pp).
Billard "Design of novel BH3 mimetics for the treatment of chronic lymphocytic leukemia", Leukemia, 2012, 26(9):2032-2038.
European Search Report in European Application No. 16842712.8, dated Jan. 24, 2019, 19 pages.
Huhn et al., "Selective covalent targeting of anti-apoptotic BFL-1 by cysteine-reactive stapled peptide inhibitors," Cell Chemical Biology, 2016, 23(9):1123-1134.
International Search Report and Written Opinion in International Appl. No. PCT/US2018/065438, dated May 5, 2019, 14 pages.
Leverson, "A New Staple: Peptide-Targeted Covalent Inhibitors," Cell chemical biology, 2016, 23(9):1043-1044.
Nakajima et al., "Noxa determines localization and stability of MCL-1 and consequently ABT-737 sensitivity in small cell lung cancer", Cell Death & Disease, 2014, 5(2):e1052.
Walensky et al., "Hydrocarbon-stapled peptides: principles, practice, and progress: miniperspective," Journal of medicinal chemistry, 2004, 57(15):6275-6288.
Youle et al., "The BCL-2 protein family: opposing activities that mediate cell death," Nature reviews Molecular cell biology, 2008, 9(1):47-59.
U.S. Appl. No. 15/752,372, US2019/0002506, filed Feb. 13, 2018, Walensky.
Adams et al., "PHENIX: A Comprehensive Python-based System for Macromolecular Structure Solution," Acta Crystallogr D Biol Cjystallogr, 2010, 66(pt. 2)213-221.
Anderson et al., "CCT241533 is a potent and selective inhibitor of CHK2 that potentiates the cytotoxicity of PARP inhibitors," Cancer Research, 2011, 74:463-472.
Awasthi et al., "ATM and ATR signaling at a glance," Journal of the Cell Science, Dec. 2015, 128:4255-4262.
Ayaz et al., "Conformational Adaption May Explain the Slow Dissociation Kinetics of Roniciclib (BAY 1000394), a Type I CDK Inhibitor With Kinetic Selectivity for CDK2 and CDK9," ACS Chem Biol, Jun. 2016, 11(6):1710-1719.
Balaram, "Non standard amino acids in peptide design and protein engineering," Current Opinion in Structural Biology, 1992, 2(6):845-851.
Beroukhim et al., "The landscape of somatic copy-number alteration across human cancers," Nature, Feb. 2010, 463(7283):899-905.
Blackwell et al., "Highly Efficient Synthesis of Covalently Cross-Linked Peptide Helices by Ring-Closing Metathesis," Angewandte Chem. Int. Ed., 1994, 37(23):3281-4.

(56) References Cited

OTHER PUBLICATIONS

Boehrer et al., "Suppression of the DNA damage response in acute myeloid leukemia versus myelodysplastic syndrome," *Oncogene*, 2009, 28(22):2205-2218.

Booth et al., "The Chk1 inhibitor SRA737 synergizes with PARP1 inhibitors to kill carcinoma cells," *Cancer Biology and Therapy*, 2018, 9:786-796.

Bridges el al., "Niraparib (MK-4827), a Novel poly(ADP-Ribose) Polymerase Inhibitor, Radiosensitizes Human Lung and Breast Cancer Cells," *Oncotarget*, Jul. 2014, 5(13):5076-5086.

Brock et al., "Radiosensitization of human and rodent cell lines by INO-1001, a novel inhibitor of poly(ADP-ribose) polymerase," *Cancer Letters*, 2004, 205(2):155-160.

Brunel et al., "Synthesis of constrained helical peptides by thioether ligation application to analogs of gp41," *Chemical Communications*, 2005, 20:2552-4.

Caenepeel et al., "Abstract 2027: Preclinical evaluation of AMG 176, a novel, potent and selective Mcl-1 inhibitor with robust anti-tumor activity in Mcl-1 dependent cancer models," *Cancer Research*, 2017, 4 pages.

Chapman et al., "A highly stable short a-helix constrained by a main-chain hydrogen-bond surrogate," *Journal of the American Chemical Society*, 2004, 126(39):12252-12253.

Chin et al., "Design and Evolution of a Miniature Bcl-2 Binding Protein," *Angew Chem Int Ed Engl.*, 2001, 40:3806-09.

Curtin et al., "Novel poly(ADP-ribose) polymerase-1 Inhibitor, AG14361, Restores Sensitivity to Temozolomide in Mismatch Repair-Deficient Cells," *Clin Cancer Res*, 2004, 10(3):881-889.

Daniel et al., "Inhibition of poly(ADP-ribose) polymerase-1 enhances temozolomide and topotecan activity against childhood neuroblastoma," *Cancer Therapy: Prechnical*, 2009, 15(4):1241-1249.

Day et al., "Structure of the BH3 Domains From the p53-inducible BH3-only Proteins Noxa and Puma in Coiriplex With Mcl-1," *J Mol. Biol.*, 2008, 380(5):958-971.

Donawho et al., "ABT-888, and orally active poly(ADP-Ribose) polymerase inhibtor that potentiates DNA-damaging agents in preclinical tumor models," *Clinical Cancer Research*, 2007, 13(9):2728-2737.

Emsley et al., "Coot: Model-Building Tools for Molecular Graphics," *Acta Crystallogr D Biol Crystallogr*, 2004, 60:2126-2132.

Evans, "Scaling and Assessment of Data Quality," *Acta Crystallogr D Biol Crystallogr*, 2006, 62 (Pt. 1):72-82.

Golding et al., "Improved ATM kinase inhibitor KU-60019 radiosensitizes glioma cells, compromises insulin, AKT and ERK prosurvival signaling, and inhibits migration and invasion," *Mol. Cancer Ther*, 2009, 8(10):2894-2902.

Gunnoo et al., "Bioconjuation—Using selective chemistry to enhance the properties of proteins and peptides as therapeutics and carriers," *Organic & Biomolecular Chemistry*, Jul. 2016, 14(34):8002-8013.

Haney et al.. "Promoting peptide a-helix formation with dynamic covalent oxime side-chain cross-links," *Chemical Communications*, Jun. 2011, 47:10915-10917.

Hickson et al., "Identification and characterization of a novel and specific inhibitor of the ataxia-telangiectasia mutated kinase ATM," *Cancer Res*, 2004, 64(24):9152-9159.

Hong et al., "Phase I Study of LY2606368, a Checkpoint Kinase 1 Inhibitor, in Patients With Advanced Cancer," *J Clin Oncol*, Apr. 2016, 34(15):1764-1771.

Horne et al., "Sequence-based Design of alpha/beta-peptide Foldamers That Mimic BH3 Domains," *Agnew Chem Int Ed Engl.*, 2008, 47(15):2853-6.

Jackson et al., "An indolocarbazole inhibitor of human checkpoint kinase (Chk1) abrogates cell cycle arrest caused by DNA damage," *Cancer Research*, 2000, 60:566-572.

Jackson et al., "General Approach to the synthesis of short a-helical peptides," *Journal of American Chemical Society*, 1991, 113:9391-9392.

Jobson et al., "Identification of a Bis-guanylhydrazone [4,4'-Diacetyldiphenylurea-bis(guanylhydrazone); NSC 109555] as a novel chemotype for inhibition of Chk2 Kinase," *Molecular Pharmacology*, 2007, 72:876-884.

Kabsch, "Integration, Scaling, Space-Group Assignment and Post-Refinement," *Acta Crystallogr D Biol Crystallogr*, 2010, 66(Pt 2):133-144.

Kemp et al., "The Structure and Energetics of Helix Formation by Short Templated Peptides in Aqueous Solution. 2. Characterization of Helical Structure of Ac—He11—Ala6—OH," *Journal of the American Chemical Society*, 1996, 118(18):4240-4248.

Kim et al., "Oxidative stress attenuates Fas-mediated apoptosis in Jurkat T cell line through Bfl-1 induction," *Oncogene*, 2005, 24, 1252-1261.

Kotschy et al., "The MCL1 Inhibitor S63845 is Tolerable and Effective in Diverse Cancer Models," *Nature*, Oct. 2016, 538(7626):477-482.

Kumita el al., "Photo control of helix content in a short peptide," *Proceedings of the National Academy of Sciences*, 2000, 3803-3808.

Laird et al., "Talazoparib is a Potent Radiosensitizer in Small Cell Lung Cancer Cell Lines and Xenografts," *Clin Cancer Res*, 2018, 24(20):5143-5152.

Lau el al., "Functionalised staple linkages for modulating the cellular activity of stapled peptides," *Chemical Science*, Mar. 2014, 5(5):1804-1809.

Lau et al., "Peptide stapling techniques based on different macrocyclisation chemistries," *Chemical Society Reviews*, Jan. 2015, 44:91-102.

Liu et al., "Iniparib nonselectively modifies cysteine containing proteins in tumor cells and is not a bona fide PARP inhibitor," *Cancer Therapy: Preclinical*, 2012, 18(2):510-523.

Madden et al., "Facile synthesis of stapled, structurally reinforced peptide helices via a photoinduced intramolecular 1,3-dipolar cycloaddition reaction," *Chem. Commun. (Camb)*, Oct. 2009, 7(37):5588-5590.

Madden el al., "Synthesis of Cell-Permeable Stapled Peptide Dual Inhibitors of the p53-Mdm2/Mdmx Interactions via Photoinduced Cycloaddition," *Bioorg. Med. Chem. Letter*, 2011, 21(5):1472-1475.

McCoy et al., "Phaser Crystallographic Software," *J Appl Crystallogr*, 2007, 40(Pt 4):658-674.

McGonigle et al., "E7449: A Dual Inhibitor of PARP1/2 and tankyrase1/2 inhibits Growth of DNA Repair Deficient Tumors and Antagonizes Wnt Signaling," *Oncotarget*, Dec. 2015, 6(38):41307-41323.

Menear et al., "4-[3-(4-Cyclopropanecarbonylpiperazine-1-carbonyl)-4-flurobenzyl]-2H-phthalazin-1-one: a novel bioavailahle inhibitor of poly(ADP-ribose_ Polymerase-1," *Journal of Medicinal Chemistry*, 2008, 51(20):6581-6591.

Meyers et al., "Computational correction of copy number effect improves specificity of CRISPR-Cas9 essentiality screens in cancer cells," *Nat. Genet*, 2017, 49(12):1779-1784.

O'Connor et al., "The PARP Inhibitor AZD2461 Provides Insights Into the Role of PARP3 Inhibition for Both Synthetic Lethality and Tolerability With Chemotherapy in Preclinical Models," *Cancer Res*, Oct. 2016, 76(20):6084-6094.

Omer et al., "Toward Proteomimetics: Terphenyl Derivatives as Structural and Functional Mimics of Extended Regions of an a-Helix," *Journal of the American Chemical Society*, 2001, 123(22):5382-5383.

PCT international Preliminary Report on Patentability in International Appln. No. PCT/US2018/065438, dated Jun. 16, 2020, 10 pages.

Penning et al., "Optimization of Phenyl-Substituted Benzimidazole Carboxamide poly(ADP-ribose) Polymerase Inhibitors: Identification of (S)-2-(2-fluoro-4-(pyrrolidin-2-yl)phenyl)-1H-benzimidazole-4-carboxamide (A-966492), a Highly Potent and Efficacious Inhibitor," *J Med Chem*, 2010, 53(8):3142-3153.

Phelan et al., "A general method for constraining short peptides to an a-helical conformation," *Journal of the American Chemical Society*, 1997, 119(3):455-460.

(56) References Cited

OTHER PUBLICATIONS

Roberts et al., "Targeting BCL2 With Venetoclax in Relapsed Chronic Lymphocytic Leukemia," *N Engl J Med*, Dec. 2016, 374(4):311-322.

Scagliotti et al., "Phase II evaluation of LY2603618, a first generation CHK1 inhibitor, in combination with pemetrexed in patients with advanced or metastatic non small cell lung cancer," *Invest New Drugs*, Oct. 2016, 34(5):625-635.

Shepherd et al., "Single Turn Peptide Alpha Helices with Exceptional Stability in Water," *Journal of the American Chemical Society*, 2005, 127(9):2974-2983.

Smaill et al., "Synthesis and structure—activity relationships of N-6 substituted analogues of 9-hydroxy-4-phenylpyrrol[3,4-c]carbazole-1,3(2H,6H)-diones as inhibitors of Wee1 and Chk1 checkpoint kinases," *European Journal of Medicinal Chemistry*, 2008, 43:1276-1296.

Spokoyny et al., "A perfluoroatyl-cysteine SnAr Chemistry approach to unprotected peptide stapling," *Journal of American Chemical Society*, 2013, 135(16):5946-5949.

Stewart et al., "The MCL-1 BH3 Helix is an Exclusive MCL-1 Inhibitor and Apoptosis Sensitizer", *Natural Chemical Biology*, 2010, 6(8):595-601.

Teng et al., "Structure-based Design and Synthesis of (5-arylamino-2H-pyrazol-3-yl)-biphenyl-2',4'-diols as Novel and Potent Human CHK1 Inhibitors," *J Med Chem*, 2007, 50(22):5253-6.

Tshemiak et. al., "Defining a Cancer Dependency Map," *Cell*, 2017, 170(3):564-576.

Weber et al., "ATM and ATR as therapeutic targets in cancer," *Pharmacology and Therapeutics*, Dec. 2014, 149:124-138.

Winter, "xia2: an expert system for macromolecular crystallography data reduction," *Appl Crystallogr*, 2010, 43(1):186-190.

Zabludoff et al., "AZD7762, a novel checkpoint kinase inhibitor, drives checkpoint abrogation and potentiates DNA-targeted therapies," *Molecular Cancer Therapeutics*, 2008, 7(9):2955-2966.

Zhu et al., "Identification of a Novel Senolytic Agent, Navitoclax, Targeting the Bcl-2 Family of Anti-Apppotic Factors," *Aging Cell*, Jun. 2016, 15(3):428-35.

U.S. Appl. No. 15/752,372, filed Feb. 13, 2018, Walensky.

International Search Report and Written Opinion in International Appln. No. PCT/US2018/065438, dated May 22, 2019, 18 pages.

Holm et al., "Electrophilic Affibodies Forming Covalent Bonds to Protein Targets," The Journal of Biological Chemistry, Nov. 2009, 284(47):32906-32913.

Walensky et al., "A Stapled BID BH3 Helix Directly Binds and Activates BAX," Molecular Cell, Oct. 2006, 24:199-210.

Clinicaltrials.gov, [online], "Phase I Study of MIK665, a Mcl-1 Inhibitor, in Patients With Refractory or Relapsed Lymphoma or Multiple Myeloma," Dec. 14, 2016, retrieved on Nov. 16, 2020, retrieved from URL<https://www.clinicaltrials.gov/ct2/show/NCT02992483?term=NCT02992483&draw=2&rank=1>, Clinical Trial ID NCT02992483, 8 pages.

Clinicaltrials.gov, [online], "Phase I Study of S64315 Administered Intravenously in Patients With Acute Myeloid Leukaemia or Myelodysplastic Syndrome," Dec. 1, 2016, retrieved on Nov. 16, 2020, retrieved from URL<https://www.clinicaltrials.gov/ct2/show/NCT02979366?term=NCT02979366&draw=2&rank=1>, Clinical Trial ID NCT02979366, 10 pages.

Clinicaltrials.gov, [online], "Safety, Tolerability, Pharmacokinetics and Efficacy of AMG 397 in Subjects With Selected Relapsed or Refractory Hematological Malignancies," Mar. 14, 2018, retrieved on Nov. 16, 2020, retrieved from URL<https://www.clinicaltrials.gov/ct2/show/NCT03465540?term=NCT03465540&draw=2&rank=1>, Clinical Trial ID NCT03465540, 20 pages.

U.S. Appl. No. 15/752,372, 2019/0002506, filed Feb. 13, 2018, Walensky.

U.S. Appl. No. 16/766,201, filed May 21, 2020, Walensky.

\* cited by examiner

| | |
|---|---|
| AELEVECATQLRXFGDXLNFRQKLL | NOXA SAHB$_A$ |
| AELEVECATQLRXFGDXLNFRQKDL | NOXA SAHB$_A$ L42D |
| AELEVELATQLRXFGDXLNFRQKLL | NOXA SAHB$_A$ C25L |
| AELEVECLTQLRXFGDXLNFRQKLL | NOXA SAHB$_A$ A26L |
| AELEVESATQLRXFGDXLNFRQKLL | NOXA SAHB$_A$ C25S |
| LEVECATQLRXFGDXLNFRQKLL | NOXA SAHB$_A$ Δ21 |
| AELEVECATQLRXFGDXLNFRQ | NOXA SAHB$_A$ Δ40 |
| AELEVECATQLRXYGDXLNFRQKLL | NOXA SAHB$_A$ F32Y |
| AELEVECATQLRXIGDXLNFRQKLL | NOXA SAHB$_A$ F32I |
| VECATQLRXFGDXLNFRQKL | NOXA SAHB$_A$ mod |
| VECATQLRXFGFXLNFRQKL | NOXA SAHB$_A$ D34F |
| AELEVXCATXLRRFGDKLNFRQKL

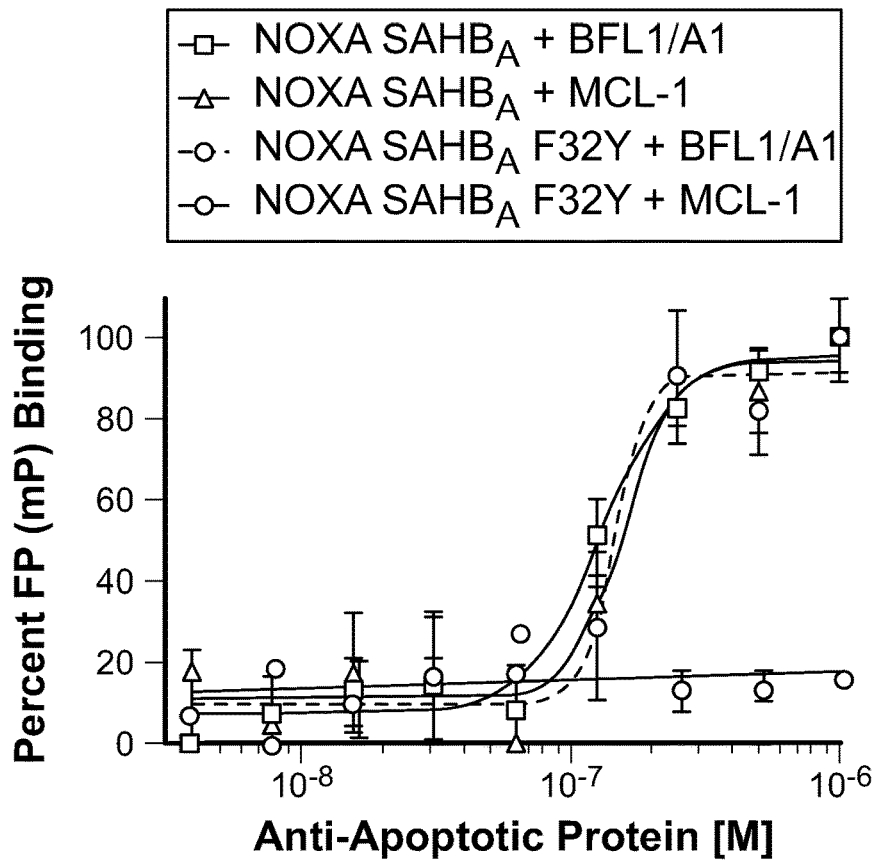

FIG. 3A

NOXA Phe32 panel: (AELEVECATQLRXFGDXLNFRQKLL)

Fmoc-Tle-OH
Fmoc-Val-OH
Fmoc-Nle-OH
Fmoc-His-OH
Fmoc-4-Pal-OH
Fmoc-Phe-OH
Fmoc-Phe(3-I)-OH
Fmoc-Phe(4-I)-OH
Fmoc-Phe(4-CN)-OH
Fmoc-Phe(4-Me)-OH
Fmoc-Phe(4-NO2)-OH
Fmoc-Phe(3,4-Cl2)-OH
Fmoc-Phe(2-F)-OH
Fmoc-Phe(3-F)-OH
Fmoc-Phe(4-F)-OH
Fmoc-Phe(3,4-F2)-OH
Fmoc-Phe(F5)-OH
Fmoc-L-homo-Phe-OH
Fmoc-Phe(4-NHBoc)-OH
Fmoc-Phe(4-guanidino-Boc2)-OH
Fmoc-Tyr(Me)-OH
Fmoc-Ala(2-naphthyl)-OH
Fmoc-Bip-OH
Fmoc-Trp-OH

FIG. 3B

| | |
|---|---|
| JEVESATQLRXFGDXLNFRQKLLK | NOXA BH3 Leu21-Lys |
| JATQLRXFGDXLNFRQKLLK | NOXA BH3 Cys25-Lys |
| JEVESATQLRXFGDXLNFRQKLL | NOXA BH3 Leu21 |
| JATQLRXFGDXLNFRQKLL | NOXA BH3 Cys25 |
| JLSESLKXIGDXLDSNK | BAX BH3 |
| JAQELRXIGDXFNAYYARK | BIM1 BH3 IIe148-Lys |
| JIAQELRXIGDXFNAYYARK | BIM2 BH3 Trp147-Lys |
| JAQELRXIGDXFNAYYARR | BIM1 BH3 IIe148 |
| JIAQELRXIGDXFNAYYARR | BIM2 BH3 Trp147 |
| | |
| JVGXQLAXIGDDINRR | BAK BH3 Gln73 |
| JGXQLAXIGDDINRR | BAK BH3 Val74 |
| JEVSTVLLRLGDELEQ | BOK BH3 Ala65 |
| JVSTVLLRLGDELEQ | BOK BH3 Glu66 |
| JSTVLLRLGDELEQ | BOK BH3 Val67 |
| JTVLLRLGDELEQ | BOK BH3 Cys68 |
| | |
| AELEVECATQLRRFGDKLNFRQKLL | NOXA |
|  GQ---VGRQLAIIGDDINR | BAK |
|   IW---IAQELRRIGDEFNAYYARR | BIM |
|    K---LSECLKRIGDELDSN | BAX |
| LAE---CTVLLRLGDELEQ | BOK (putative) |
|    ** ** ** ** ** ** | |

FIG. 6

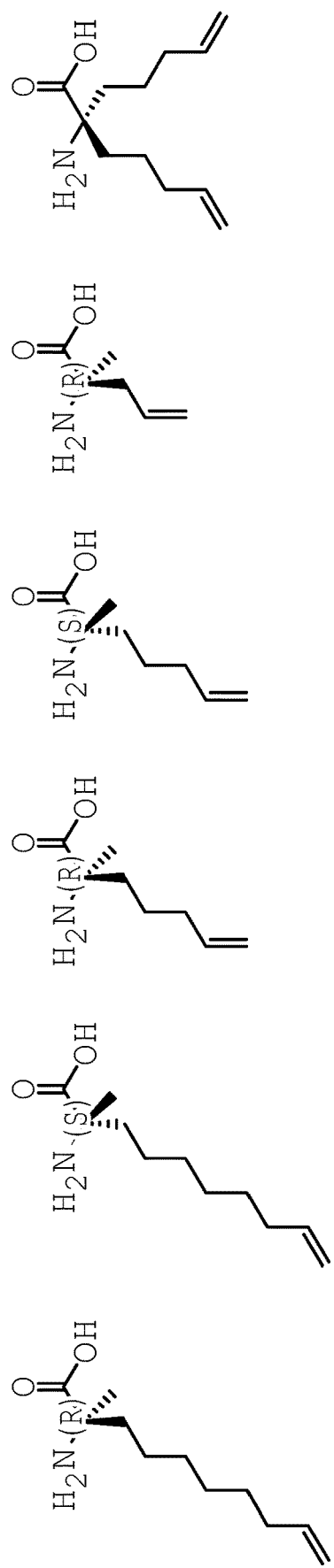
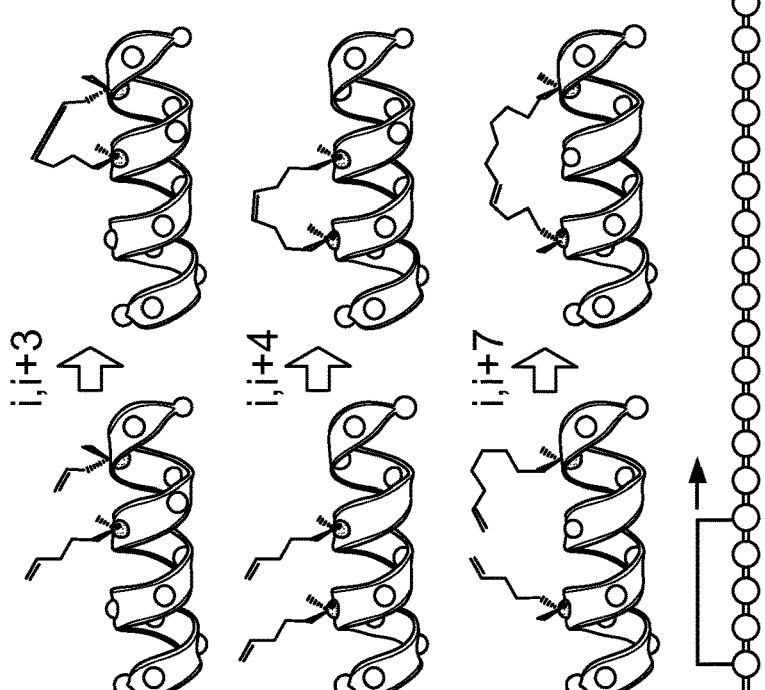
FIG. 7

NOXA BH3

BFL-1ΔC

NOXA SAHB$_A$: $^{19}$AELEVECATQLRXFGDXLNFRQKLL$^{43}$

NOXA SAHB$_A$ C25S: $^{19}$AELEVESATQLRXFGDXLNFRQKLL$^{43}$

| Protein | SAHB | $K_d$ (nM) |
|---|---|---|
| BFL-1 WT | NOXA WT | 122 |
| BFL-1 C4S/C19S | NOXA WT | 165 |
| BFL-1 C4S/C19S/C55S | NOXA WT | 118 |
| BFL-1 WT | NOXA C25S | 46.6 |
| BFL-1 C4S/C19S | NOXA C25S | 47.2 |
| BFL-1 C4S/C19S/C55S | NOXA C25S | 58.2 |

NOXA SAHB$_A$-WH: $^{21}$JEVESATQLRXFGDXLNFRQKLL$^{43}$
BIM SAHB$_A$-WH: $^{147}$JIAQELRXIGDXFNAYYARR$^{166}$

| Peptide | N-terminus | Sequence | C-terminus | MW | (M+3)/3 |
|---|---|---|---|---|---|
| NOXA SAHB$_A$ WT (aa 19-43) | FITC-βAla- | AELEVECATQLRXFGDXLNFRQKLL | | 3403.1 | 1135.3 |
| NOXA SAHB$_A$ WT | Btn-PEG-βAla- | AELEVECATQLRXFGDXLNFRQKLL | | 3556.0 | 1186.3 |
| NOXA SAHB$_A$ C25S | FITC-βAla- | AELEVESATQLRXFGDXLNFRQKLL | | 3387.0 | 1130.1 |
| NOXA SAHB$_A$ C25S | Btn-PEG-βAla- | AELEVESATQLRXFGDXLNFRQKLL | | 3539.9 | 1181.1 |
| NOXA SAHB$_A$-1 | 1 | EVESATQLRXFGDXLNFRQKLLK | | 2892.6 | 965.3 |
| NOXA SAHB$_A$-2 | 2 | EVESATQLRXFGDXLNFRQKLLK | | 2906.6 | 970.0 |
| NOXA SAHB$_A$-3 | 3 | EVESATQLRXFGDXLNFRQKLL | | 2778.4 | 927.2 |
| NOXA SAHB$_A$-3 | 3 | EVESATQLRXFGDXLNFRQKLL | Lys(biotin) | 3132.6 | 1045.2 |
| NOXA SAHB$_A$-4 | 4 | EVESATQLRXFGDXLNFRQKLLK | | 2906.6 | 969.9 |
| NOXA SAHB$_A$-5 | 5 | EVESATQLRXFGDXLNFRQKLLK | | 2892.6 | 965.2 |
| NOXA SAHB$_A$-6 | 6 | EVESATQLRXFGDXLNFRQKLLK | | 2892.6 | 965.3 |
| NOXA SAHB$_A$-7 | 7 | EVESATQLRXFGDXLNFRQKLLK | | 2852.5 | 951.8 |
| NOXA SAHB$_A$-8 | 8 | EVESATQLRXFGDXLNFRQKLLK | | 2795.4 | 932.9 |
| NOXA SAHB$_A$(aa 22-43) | Ac | EVESATQLRXFGDXLNFRQKLL | | 2655.3 | 886.0 |
| NOXA SAHB$_A$ | Ac | EVESATQLRXFGDXLNFRQKLL | Lys(biotin) | 3009.4 | 1004.2 |
| BIM SAHB$_A$-1 | 1 | IAQELRXIGDXFNAYYARK | | 2428.0 | 810.5 |
| BIM SAHB$_A$-2 | 2 | IAQELRXIGDXFNAYYARK | | 2442.0 | 815.0 |
| BIM SAHB$_A$-3 | 3 | IAQELRXIGDXFNAYYARR | | 2469.3 | 824.4 |
| BIM SAHB$_A$-3 | 3 | IAQELRXIGDXFNAYYARR | Lys(biotin) | 2823.5 | 942.3 |
| BIM SAHB$_A$-4 | 4 | IAQELRXIGDXFNAYYARK | | 2442.0 | 815.0 |
| BIM SAHB$_A$-5 | 5 | IAQELRXIGDXFNAYYARK | | 2428.0 | 810.3 |
| BIM SAHB$_A$-6 | 6 | IAQELRXIGDXFNAYYARK | | 2428.0 | 810.3 |
| BIM SAHB$_A$-7 | 7 | IAQELRXIGDXFNAYYARK | | 2388.0 | 797.1 |
| BIM SAHB$_A$-8 | 8 | IAQELRXIGDXFNAYYARK | | 2330.9 | 778.0 |
| BIM SAHB$_A$(aa 148-166) | Ac | IAQELRXIGDXFNAYYARR | | 2346.9 | 783.3 |
| BIM SAHB$_A$ | Ac | IAQELRXIGDXFNAYYARR | Lys(biotin) | 2701.1 | 901.4 |
| BIM SAHB$_{A1}$(aa 146-166) | FITC-βAla- | IWIAQELRXIGDXFNAYYARR | | 3064.3 | 1022.4 |
| BIM SAHB$_A$-3 | FITC-Cyste-3- | IAQELRXIGDXFNAYYARR | | 2935.5 | 979.8 |
| BIM SAHB$_{A1}$(aa 146-166) | Ac | IWIAQELRXIGDXFNAYYARR | | 2646.3 | 883.1 |

1: (S)-1-acryloylpyrrolidine-3-carboxamide; 2: 1-acryloylpiperidine-4-carboxamide;
3: (R)-1 acryloylpiperidine-3-carboxamide; 4: (S)-1-acryloylpiperidine-3-carboxamide;
5: (S)-1-acryloylpyrrolidine-2-carboxamide; 6: (R)-1 acryloylpyrrolidine-2-carboxamide;
7: (E)-4-(dimethylamino)but-2-enamide; 8: acrylamide; FITC-Cyste: FITC-cysteamine.

FIG. 18

4zeq_BID-BFL1
JDIIRNIARHLAQVGDSMDRSI (SEQ ID NO: 41)
EDJIRNIARHLAQVGDSMDRSI (SEQ ID NO: 42)
EDIIRJIARHLAQVGDSMDRSI (SEQ ID NO: 43)
EDIIRNJARHLAQVGDSMDRSI (SEQ ID NO: 44)
JIIRNIARHLAXVGDXBDR (SEQ ID NO: 45)
JIRNIARHLAXVGDXBDR (SEQ ID NO: 46)
JIARHLAXVGDXBDR (SEQ ID NO: 47)
JARHLAXVGDXBDR (SEQ ID NO: 48)

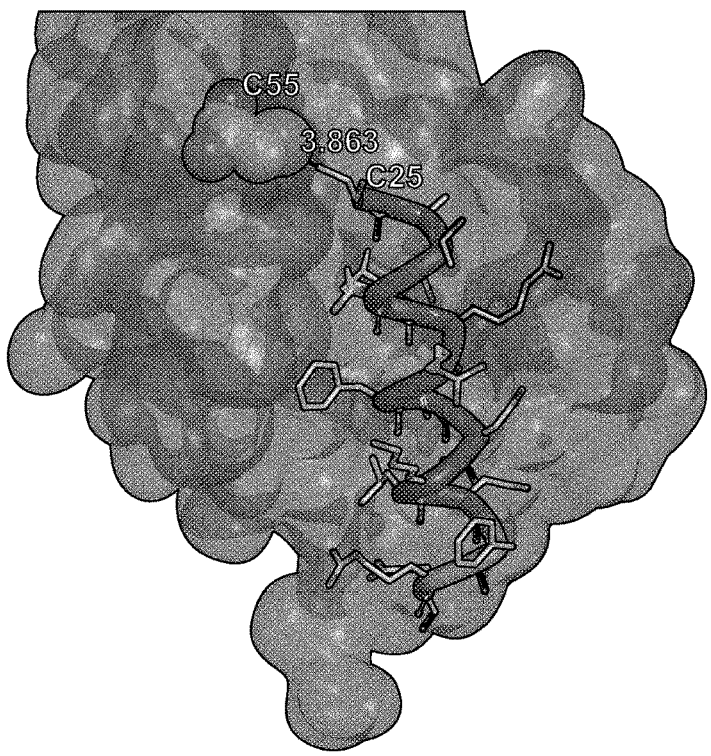

3mqp_shNOXA-BFL1

| | |
|---|---|
| JXTQLXRFGDKLNFRQ | (SEQ ID NO: 49) |
| JAXQLRXFGDKLNFRQ | (SEQ ID NO: 50) |
| JATXLRRXGDKLNFRQ | (SEQ ID NO: 51) |
| JATQXRRFXDKLNFRQ | (SEQ ID NO: 52) |
| JATQLXRFGXKLNFRQ | (SEQ ID NO: 53) |
| JATQLRXFGDXLNFRQ | (SEQ ID NO: 54) |
| JATQLRRXGDKXNFRQ | (SEQ ID NO: 55) |
| JATQLRRFXDKLXFRQ | (SEQ ID NO: 56) |
| JATQLRRFGXKLNXRQ | (SEQ ID NO: 57) |
| JATQLRRFGDKXNFRX | (SEQ ID NO: 58) |
| JATQLRRFGDKLXFRQX | (SEQ ID NO: 59) |
| J8TQLRRFXDKLNFRQ | (SEQ ID NO: 60) |
| JA8QLRRFGXKLNFRQ | (SEQ ID NO: 61) |
| JAT8LRRFGDXLNFRQ | (SEQ ID NO: 62) |
| JATQ8RRFGDKXNFRQ | (SEQ ID NO: 63) |
| JATQL8RFGDKLXFRQ | (SEQ ID NO: 64) |
| JATQLR8FGDKLNXRQ | (SEQ ID NO: 65) |
| JATQLRR8GDKLNFXQ | (SEQ ID NO: 66) |
| JATQLRRF8DKLNFRX | (SEQ ID NO: 67) |

FIG. 20

3i1h_BAK-BFL1

BAK BH3 Stapled Peptides With Warheads:

| | |
|---|---|
| GQVGRQLAIIGDDINR | (SEQ ID NO: 37) |
| JXRQLXIIGDDINR | (SEQ ID NO: 68) |
| JGXQLAXIGDDINR | (SEQ ID NO:32) |
| JGRXLAIXGDDINR | (SEQ ID NO:69) |
| JGRQXAIIXDDINR | (SEQ ID NO:70) |
| JGRQLXIIGXDINR | (SEQ ID NO:71) |
| JGRQLAXIGDXINR | (SEQ ID NO:72) |
| JGRQLAIXGDDXNR | (SEQ ID NO:73) |
| JGRQLAIIXDDIXR | (SEQ ID NO:74) |
| JGRQLAIIGXDINX | (SEQ ID NO:75) |
| JGRQLAIIGDXINRX | (SEQ ID NO:76) |
| J8RQLAIIXDDINR | (SEQ ID NO:77) |
| JG8QLAIIGXDINR | (SEQ ID NO:78) |
| JGR8LAIIGDXINR | (SEQ ID NO:79) |
| JGRQ8AIIGDDXNR | (SEQ ID NO:80) |
| JGRQL8IIGDDIXR | (SEQ ID NO:81) |
| JGRQLA8IGDDINX | (SEQ ID NO:82) |
| JGRQLAI8GDDINRX | (SEQ ID NO:83) |
| JVXRQLXIIGDDINR | (SEQ ID NO:84) |
| JVGXQLAXIGDDINR | (SEQ ID NO:85) |
| JVGRXLAIXGDDINR | (SEQ ID NO:86) |
| JVGRQXAIIXDDINR | (SEQ ID NO:87) |
| JVGRQLXIIGXDINR | (SEQ ID NO:88) |
| JVGRQLAXIGDXINR | (SEQ ID NO:89) |
| JVGRQLAIXGDDXNR | (SEQ ID NO:90) |
| JVGRQLAIIXDDIXR | (SEQ ID NO:91) |
| JVGRQLAIIGXDINX | (SEQ ID NO:92) |
| JVGRQLAIIGDXINRX | (SEQ ID NO:93) |
| JV8RQLAIIXDDINR | (SEQ ID NO:94) |
| JVG8QLAIIGXDINR | (SEQ ID NO:95) |
| JVGR8LAIIGDXINR | (SEQ ID NO:96) |
| JVGRQ8AIIGDDXNR | (SEQ ID NO:97) |
| JVGRQL8IIGDDIXR | (SEQ ID NO:98) |
| JVGRQLA8IGDDINX | (SEQ ID NO:99) |
| JVGRQLAI8GDDINRX | (SEQ ID NO:100) |

FIG. 23

BAX BH3 Stapled Peptides With Warheads:

| | |
|---|---|
| JXSESXKRIGDELDS | (SEQ ID NO:101) |
| JLXESLXRIGDELDS | (SEQ ID NO:102) |
| JLSXSLKXIGDELDS | (SEQ ID NO:103) |
| JLSEXLKRXGDELDS | (SEQ ID NO:104) |
| JLSESXKRIXDELDS | (SEQ ID NO:105) |
| JLSESLXRIGXELDS | (SEQ ID NO:106) |
| JLSESLKXIGDXLDS | (SEQ ID NO:107) |
| JLSESLKRXGDEXDS | (SEQ ID NO:108) |
| JLSESLKRIXDELXS | (SEQ ID NO:109) |
| JLSESLKRIGXELDX | (SEQ ID NO:110) |
| JLSESLKRIGDXLDSX | (SEQ ID NO:111) |
| J8SESLKRXGDELDS | (SEQ ID NO:112) |
| JL8ESLKRIXDELDS | (SEQ ID NO:113) |
| JLS8SLKRIGXELDS | (SEQ ID NO:114) |
| JLSE8LKRIGDXLDS | (SEQ ID NO:115) |
| JLSES8KRIGDEXDS | (SEQ ID NO:116) |
| JLSESL8RIGDELXS | (SEQ ID NO:117) |
| JLSESLK8IGDELDX | (SEQ ID NO:118) |
| JLSESLKR8GDELDSX | (SEQ ID NO:119) |

FIG. 24

| | |
|---|---|
| BIM5 | JIAQELRXIGDXFNAYYARR (SEQ ID NO: 30) |
| NOXA1 | JXTQLXRFGDKLNFRQ (SEQ ID NO: 49) |
| NOXA2 | JAXQLRXFGDKLNFRQ (SEQ ID NO: 50) |
| NOXA3 | JATXLRRXGDKLNFRQ (SEQ ID NO: 51) |
| NOXA6 | JATQLRXFGDXLNFRQ (SEQ ID NO: 54) |
| NOXA11 | JATQLRRFGDKXNFRX (SEQ ID NO: 58) |
| NOXA12 | JATQLRRFGDKLXFRQX (SEQ ID NO: 59) |
| NOXA13 | J8TQLRRFXDKLNFRQ (SEQ ID NO: 60) |
| NOXA15 | JAT8LRRFGDXLNFRQ (SEQ ID NO: 62) |
| NOXA18 | JATQLR8FGDKLNXRQ (SEQ ID NO: 65) |
| NOXA19 | JATQLRR8GDKLNFXQ (SEQ ID NO: 66) |

SEQUENCE LISTING

```
<160> NUMBER OF SEQ ID NOS: 210

<210> SEQ ID NO 1
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Glu Leu Glu Val Glu Ser Ala Thr Gln Leu Arg Arg Phe Gly Asp
1               5                   10                  15

Lys Leu Asn Phe Arg Gln Lys Leu Leu
            20                  25

<210> SEQ ID NO 2
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Met Pro Arg Glu Ile Trp Ile Ala Gln Glu Leu Arg Arg Ile Gly
1               5                   10                  15

Asp Glu Phe Asn Ala Tyr Tyr Ala Arg Arg
            20                  25
```

```
<210> SEQ ID NO 3
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Asp Ala Ser Thr Lys Lys Leu Ser Glu Ser Leu Lys Arg Ile Gly
1               5                   10                  15

Asp Glu Leu Asp Ser Asn Met Glu Leu Gln Arg
            20                  25

<210> SEQ ID NO 4
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ser Ser Thr Met Gly Gln Val Gly Arg Gln Leu Ala Ile Ile Gly Asp
1               5                   10                  15

Asp Ile Asn Arg Arg Tyr Asp Ser Glu Phe Gln Thr Met Leu Gln His
            20                  25                  30

Leu Gln

<210> SEQ ID NO 5
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Pro Gly Gly Arg Leu Ala Glu Val Ser Thr Val Leu Leu Arg Leu Gly
1               5                   10                  15

Asp Glu Leu Glu Gln Ile Arg Pro Ser
            20                  25

<210> SEQ ID NO 6
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Glu Ser Gln Glu Asp Ile Ile Arg Asn Ile Ala Arg His Leu Ala
1               5                   10                  15

Gln Val Gly Asp Ser Met Asp Arg Ser Ile Pro Pro Gly
            20                  25

<210> SEQ ID NO 7
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7
```

```
Glu Gln Glu Gln Trp Ala Arg Glu Ile Gly Ala Gln Leu Arg Arg Met
1               5                   10                  15

Ala Asp Asp Leu Asn Ala Gln Tyr Glu Arg Arg Gln Glu Glu Gln
            20                  25                  30

Gln

<210> SEQ ID NO 8
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Lys Lys Phe Glu Pro Lys Ser Gly Trp Met Thr Phe Leu Glu Val Thr
1               5                   10                  15

Gly Lys Ile Cys Glu Met Leu Ser Leu Leu Lys Gln Tyr Cys
            20                  25                  30

<210> SEQ ID NO 9
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Any non-natural amino acid
<220> FEATURE:
<221> NAME/KEY: MOD_RES
<222> LOCATION: (17)..(17)
<223> OTHER INFORMATION: Any non-natural amino acid

<400> SEQUENCE: 9

Ala Glu Leu Glu Val Glu Cys Ala Thr Gln Leu Arg Xaa Phe Gly Asp
1               5                   10                  15

Xaa Leu Asn Phe Arg Gln Lys Leu Leu
            20                  25

<210> SEQ ID NO 10
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Any non-natural amino acid
<220> FEATURE:
<221> NAME/KEY: MOD_RES
<222> LOCATION: (17)..(17)
<223> OTHER INFORMATION: Any non-natural amino acid

<400> SEQUENCE: 10

Ala Glu Leu Glu Val Glu Cys Ala Thr Gln Leu Arg Xaa Phe Gly Asp
1               5                   10                  15

Xaa Leu Asn Phe Arg Gln Lys Asp Leu
            20                  25

<210> SEQ ID NO 11
<211> LENGTH: 25
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Any non-natural amino acid
<220> FEATURE:
<221> NAME/KEY: MOD_RES
<222> LOCATION: (17)..(17)
<223> OTHER INFORMATION: Any non-natural amino acid

<400> SEQUENCE: 11

Ala Glu Leu Glu Val Glu Leu Ala Thr Gln Leu Arg Xaa Phe Gly Asp
1               5                   10                  15

Xaa Leu Asn Phe Arg Gln Lys Leu Leu
            20                  25

<210> SEQ ID NO 12
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Any non-natural amino acid
<220> FEATURE:
<221> NAME/KEY: MOD_RES
<222> LOCATION: (17)..(17)
<223> OTHER INFORMATION: Any non-natural amino acid

<400> SEQUENCE: 12

Ala Glu Leu Glu Val Glu Cys Leu Thr Gln Leu Arg Xaa Phe Gly Asp
1               5                   10                  15

Xaa Leu Asn Phe Arg Gln Lys Leu Leu
            20                  25

<210> SEQ ID NO 13
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Any non-natural amino acid
<220> FEATURE:
<221> NAME/KEY: MOD_RES
<222> LOCATION: (17)..(17)
<223> OTHER INFORMATION: Any non-natural amino acid

<400> SEQUENCE: 13

Ala Glu Leu Glu Val Glu Ser Ala Thr Gln Leu Arg Xaa Phe Gly Asp
1               5                   10                  15

Xaa Leu Asn Phe Arg Gln Lys Leu Leu
            20                  25

<210> SEQ ID NO 14
<211> LENGTH: 23
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<221> NAME/KEY: MOD_RES
<222> LOCATION: (11)..(11)
<223> OTHER INFORMATION: Any non-natural amino acid
<220> FEATURE:
<221> NAME/KEY: MOD_RES
<222> LOCATION: (15)..(15)
<223> OTHER INFORMATION: Any non-natural amino acid

<400> SEQUENCE: 14

Leu Glu Val Glu Cys Ala Thr Gln Leu Arg Xaa Phe Gly Asp Xaa Leu
1               5                  10                  15

Asn Phe Arg Gln Lys Leu Leu
            20

<210> SEQ ID NO 15
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Any non-natural amino acid
<220> FEATURE:
<221> NAME/KEY: MOD_RES
<222> LOCATION: (17)..(17)
<223> OTHER INFORMATION: Any non-natural amino acid

<400> SEQUENCE: 15

Ala Glu Leu Glu Val Glu Cys Ala Thr Gln Leu Arg Xaa Phe Gly Asp
1               5                  10                  15

Xaa Leu Asn Phe Arg Gln
            20

<210> SEQ ID NO 16
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Any non-natural amino acid
<220> FEATURE:
<221> NAME/KEY: MOD_RES
<222> LOCATION: (17)..(17)
<223> OTHER INFORMATION: Any non-natural amino acid

<400> SEQUENCE: 16

Ala Glu Leu Glu Val Glu Cys Ala Thr Gln Leu Arg Xaa Tyr Gly Asp
1               5                  10                  15

Xaa Leu Asn Phe Arg Gln Lys Leu Leu
            20                  25

<210> SEQ ID NO 17
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
```

```
<223> OTHER INFORMATION: Any non-natural amino acid
<220> FEATURE:
<221> NAME/KEY: MOD_RES
<222> LOCATION: (17)..(17)
<223> OTHER INFORMATION: Any non-natural amino acid

<400> SEQUENCE: 17

Ala Glu Leu Glu Val Glu Cys Ala Thr Gln Leu Arg Xaa Ile Gly Asp
1               5                   10                  15

Xaa Leu Asn Phe Arg Gln Lys Leu Leu
            20                  25

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any non-natural amino acid
<220> FEATURE:
<221> NAME/KEY: MOD_RES
<222> LOCATION: (13)..(13)
<223> OTHER INFORMATION: Any non-natural amino acid

<400> SEQUENCE: 18

Val Glu Cys Ala Thr Gln Leu Arg Xaa Phe Gly Asp Xaa Leu Asn Phe
1               5                   10                  15

Arg Gln Lys Leu
            20

<210> SEQ ID NO 19
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any non-natural amino acid
<220> FEATURE:
<221> NAME/KEY: MOD_RES
<222> LOCATION: (13)..(13)
<223> OTHER INFORMATION: Any non-natural amino acid

<400> SEQUENCE: 19

Val Glu Cys Ala Thr Gln Leu Arg Xaa Phe Gly Phe Xaa Leu Asn Phe
1               5                   10                  15

Arg Gln Lys Leu
            20

<210> SEQ ID NO 20
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any non-natural amino acid
<220> FEATURE:
<221> NAME/KEY: MOD_RES
<222> LOCATION: (10)..(10)
```

```
<223> OTHER INFORMATION: Any non-natural amino acid

<400> SEQUENCE: 20

Ala Glu Leu Glu Val Xaa Cys Ala Thr Xaa Leu Arg Arg Phe Gly Asp
1               5                   10                  15

Lys Leu Asn Phe Arg Gln Lys Leu Leu
            20                  25

<210> SEQ ID NO 21
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Any non-natural amino acid
<220> FEATURE:
<221> NAME/KEY: MOD_RES
<222> LOCATION: (23)..(23)
<223> OTHER INFORMATION: Any non-natural amino acid

<400> SEQUENCE: 21

Ala Glu Leu Glu Val Glu Cys Ala Thr Gln Leu Arg Arg Phe Gly Asp
1               5                   10                  15

Lys Leu Xaa Phe Arg Gln Xaa Leu Leu
            20                  25

<210> SEQ ID NO 22
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (11)..(11)
<223> OTHER INFORMATION: Any non-natural amino acid
<220> FEATURE:
<221> NAME/KEY: MOD_RES
<222> LOCATION: (15)..(15)
<223> OTHER INFORMATION: Any non-natural amino acid

<400> SEQUENCE: 22

Xaa Glu Val Glu Ser Ala Thr Gln Leu Arg Xaa Phe Gly Asp Xaa Leu
1               5                   10                  15

Asn Phe Arg Gln Lys Leu Leu Lys
            20

<210> SEQ ID NO 23
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
```

<221> NAME/KEY: MOD_RES
<222> LOCATION: (7)..(7)
<223> OTHER INFORMATION: Any non-natural amino acid
<220> FEATURE:
<221> NAME/KEY: MOD_RES
<222> LOCATION: (11)..(11)
<223> OTHER INFORMATION: Any non-natural amino acid

<400> SEQUENCE: 23

Xaa Ala Thr Gln Leu Arg Xaa Phe Gly Asp Xaa Leu Asn Phe Arg Gln
1               5                   10                  15

Lys Leu Leu Lys
            20

<210> SEQ ID NO 24
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (11)..(11)
<223> OTHER INFORMATION: Any non-natural amino acid
<220> FEATURE:
<221> NAME/KEY: MOD_RES
<222> LOCATION: (15)..(15)
<223> OTHER INFORMATION: Any non-natural amino acid

<400> SEQUENCE: 24

Xaa Glu Val Glu Ser Ala Thr Gln Leu Arg Xaa Phe Gly Asp Xaa Leu
1               5                   10                  15

Asn Phe Arg Gln Lys Leu Leu
            20

<210> SEQ ID NO 25
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (7)..(7)
<223> OTHER INFORMATION: Any non-natural amino acid
<220> FEATURE:
<221> NAME/KEY: MOD_RES
<222> LOCATION: (11)..(11)
<223> OTHER INFORMATION: Any non-natural amino acid

<400> SEQUENCE: 25

Xaa Ala Thr Gln Leu Arg Xaa Phe Gly Asp Xaa Leu Asn Phe Arg Gln
1               5                   10                  15

Lys Leu Leu

<210> SEQ ID NO 26
<211> LENGTH: 17
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (8)..(8)
<223> OTHER INFORMATION: Any non-natural amino acid
<220> FEATURE:
<221> NAME/KEY: MOD_RES
<222> LOCATION: (12)..(12)
<223> OTHER INFORMATION: Any non-natural amino acid

<400> SEQUENCE: 26

Xaa Leu Ser Glu Ser Leu Lys Xaa Ile Gly Asp Xaa Leu Asp Ser Asn
1               5                   10                  15

Lys

<210> SEQ ID NO 27
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (7)..(7)
<223> OTHER INFORMATION: Any non-natural amino acid
<220> FEATURE:
<221> NAME/KEY: MOD_RES
<222> LOCATION: (11)..(11)
<223> OTHER INFORMATION: Any non-natural amino acid

<400> SEQUENCE: 27

Xaa Ala Gln Glu Leu Arg Xaa Ile Gly Asp Xaa Phe Asn Ala Tyr Tyr
1               5                   10                  15

Ala Arg Lys

<210> SEQ ID NO 28
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (8)..(8)
<223> OTHER INFORMATION: Any non-natural amino acid
<220> FEATURE:
<221> NAME/KEY: MOD_RES
<222> LOCATION: (12)..(12)
<223> OTHER INFORMATION: Any non-natural amino acid

<400> SEQUENCE: 28

Xaa Ile Ala Gln Glu Leu Arg Xaa Ile Gly Asp Xaa Phe Asn Ala Tyr
```

```
1               5                   10                  15
Tyr Ala Arg Lys
            20

<210> SEQ ID NO 29
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (7)..(7)
<223> OTHER INFORMATION: Any non-natural amino acid
<220> FEATURE:
<221> NAME/KEY: MOD_RES
<222> LOCATION: (11)..(11)
<223> OTHER INFORMATION: Any non-natural amino acid

<400> SEQUENCE: 29

Xaa Ala Gln Glu Leu Arg Xaa Ile Gly Asp Xaa Phe Asn Ala Tyr Tyr
1               5                   10                  15

Ala Arg Arg

<210> SEQ ID NO 30
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (8)..(8)
<223> OTHER INFORMATION: Any non-natural amino acid
<220> FEATURE:
<221> NAME/KEY: MOD_RES
<222> LOCATION: (12)..(12)
<223> OTHER INFORMATION: Any non-natural amino acid

<400> SEQUENCE: 30

Xaa Ile Ala Gln Glu Leu Arg Xaa Ile Gly Asp Xaa Phe Asn Ala Tyr
1               5                   10                  15

Tyr Ala Arg Arg
            20

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
```

```
<222> LOCATION: (4)..(4)
<223> OTHER INFORMATION: Any non-natural amino acid
<220> FEATURE:
<221> NAME/KEY: MOD_RES
<222> LOCATION: (8)..(8)
<223> OTHER INFORMATION: Any non-natural amino acid

<400> SEQUENCE: 31

Xaa Val Gly Xaa Gln Leu Ala Xaa Ile Gly Asp Asp Ile Asn Arg Arg
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (3)..(3)
<223> OTHER INFORMATION: Any non-natural amino acid
<220> FEATURE:
<221> NAME/KEY: MOD_RES
<222> LOCATION: (7)..(7)
<223> OTHER INFORMATION: Any non-natural amino acid
<220> FEATURE:
<221> NAME/KEY: MOD_RES
<222> LOCATION: (15)..(15)
<223> OTHER INFORMATION: May or may not be present

<400> SEQUENCE: 32

Xaa Gly Xaa Gln Leu Ala Xaa Ile Gly Asp Asp Ile Asn Arg Arg
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present

<400> SEQUENCE: 33

Xaa Glu Val Ser Thr Val Leu Leu Arg Leu Gly Asp Glu Leu Glu Gln
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present

<400> SEQUENCE: 34

Xaa Val Ser Thr Val Leu Leu Arg Leu Gly Asp Glu Leu Glu Gln
```

```
<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present

<400> SEQUENCE: 35

Xaa Ser Thr Val Leu Leu Arg Leu Gly Asp Glu Leu Glu Gln
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present

<400> SEQUENCE: 36

Xaa Thr Val Leu Leu Arg Leu Gly Asp Glu Leu Glu Gln
1               5                   10

<210> SEQ ID NO 37
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Gln Val Gly Arg Gln Leu Ala Ile Ile Gly Asp Asp Ile Asn Arg
1               5                   10                  15

<210> SEQ ID NO 38
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ile Trp Ile Ala Gln Glu Leu Arg Arg Ile Gly Asp Glu Phe Asn Ala
1               5                   10                  15

Tyr Tyr Ala Arg Arg
            20

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 39

Lys Leu Ser Glu Cys Leu Lys Arg Ile Gly Asp Glu Leu Asp Ser Asn
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Leu Ala Glu Cys Thr Val Leu Leu Arg Leu Gly Asp Glu Leu Glu Gln
1               5                   10                  15

<210> SEQ ID NO 41
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present

<400> SEQUENCE: 41

Xaa Asp Ile Ile Arg Asn Ile Ala Arg His Leu Ala Gln Val Gly Asp
1               5                   10                  15

Ser Met Asp Arg Ser Ile
            20

<210> SEQ ID NO 42
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Non-natural electrophile containing amino acid
      or not present

<400> SEQUENCE: 42

Glu Asp Xaa Ile Arg Asn Ile Ala Arg His Leu Ala Gln Val Gly Asp
1               5                   10                  15

Ser Met Asp Arg Ser Ile
            20

<210> SEQ ID NO 43
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Non-natural electrophile containing amino acid
      or not present

<400> SEQUENCE: 43

```
Glu Asp Ile Ile Arg Xaa Ile Ala Arg His Leu Ala Gln Val Gly Asp
1               5                   10                  15

Ser Met Asp Arg Ser Ile
            20
```

<210> SEQ ID NO 44
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Non-natural electrophile containing amino acid
      or not present

<400> SEQUENCE: 44

```
Glu Asp Ile Ile Arg Asn Xaa Ala Arg His Leu Ala Gln Val Gly Asp
1               5                   10                  15

Ser Met Asp Arg Ser Ile
            20
```

<210> SEQ ID NO 45
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (12)..(12)
<223> OTHER INFORMATION: Any non-natural amino acid
<220> FEATURE:
<221> NAME/KEY: MOD_RES
<222> LOCATION: (16)..(16)
<223> OTHER INFORMATION: Any non-natural amino acid
<220> FEATURE:
<221> NAME/KEY: MOD_RES
<222> LOCATION: (17)..(17)
<223> OTHER INFORMATION: Norleucine

<400> SEQUENCE: 45

```
Xaa Ile Ile Arg Asn Ile Ala Arg His Leu Ala Xaa Val Gly Asp Xaa
1               5                   10                  15

Xaa Asp Arg
```

<210> SEQ ID NO 46
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (11)..(11)
<223> OTHER INFORMATION: Any non-natural amino acid

```
<220> FEATURE:
<221> NAME/KEY: MOD_RES
<222> LOCATION: (15)..(15)
<223> OTHER INFORMATION: Any non-natural amino acid
<220> FEATURE:
<221> NAME/KEY: MOD_RES
<222> LOCATION: (16)..(16)
<223> OTHER INFORMATION: Norleucine

<400> SEQUENCE: 46

Xaa Ile Arg Asn Ile Ala Arg His Leu Ala Xaa Val Gly Asp Xaa Xaa
1               5                   10                  15

Asp Arg

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (8)..(8)
<223> OTHER INFORMATION: Any non-natural amino acid
<220> FEATURE:
<221> NAME/KEY: MOD_RES
<222> LOCATION: (12)..(12)
<223> OTHER INFORMATION: Any non-natural amino acid
<220> FEATURE:
<221> NAME/KEY: MOD_RES
<222> LOCATION: (13)..(13)
<223> OTHER INFORMATION: Norleucine

<400> SEQUENCE: 47

Xaa Ile Ala Arg His Leu Ala Xaa Val Gly Asp Xaa Xaa Asp Arg
1               5                   10                  15

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (7)..(7)
<223> OTHER INFORMATION: Any non-natural amino acid
<220> FEATURE:
<221> NAME/KEY: MOD_RES
<222> LOCATION: (11)..(11)
<223> OTHER INFORMATION: Any non-natural amino acid
<220> FEATURE:
<221> NAME/KEY: MOD_RES
<222> LOCATION: (12)..(12)
<223> OTHER INFORMATION: Norleucine

<400> SEQUENCE: 48

Xaa Ala Arg His Leu Ala Xaa Val Gly Asp Xaa Xaa Asp Arg
1               5                   10
```

```
<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (2)..(2)
<223> OTHER INFORMATION: Any non-natural amino acid
<220> FEATURE:
<221> NAME/KEY: MOD_RES
<222> LOCATION: (6)..(6)
<223> OTHER INFORMATION: Any non-natural amino acid

<400> SEQUENCE: 49

Xaa Xaa Thr Gln Leu Xaa Arg Phe Gly Asp Lys Leu Asn Phe Arg Gln
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (3)..(3)
<223> OTHER INFORMATION: Any non-natural amino acid
<220> FEATURE:
<221> NAME/KEY: MOD_RES
<222> LOCATION: (7)..(7)
<223> OTHER INFORMATION: Any non-natural amino acid

<400> SEQUENCE: 50

Xaa Ala Xaa Gln Leu Arg Xaa Phe Gly Asp Lys Leu Asn Phe Arg Gln
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (4)..(4)
<223> OTHER INFORMATION: Any non-natural amino acid
<220> FEATURE:
<221> NAME/KEY: MOD_RES
<222> LOCATION: (8)..(8)
<223> OTHER INFORMATION: Any non-natural amino acid

<400> SEQUENCE: 51

Xaa Ala Thr Xaa Leu Arg Arg Xaa Gly Asp Lys Leu Asn Phe Arg Gln
1               5                   10                  15
```

```
<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (5)..(5)
<223> OTHER INFORMATION: Any non-natural amino acid
<220> FEATURE:
<221> NAME/KEY: MOD_RES
<222> LOCATION: (9)..(9)
<223> OTHER INFORMATION: Any non-natural amino acid

<400> SEQUENCE: 52

Xaa Ala Thr Gln Xaa Arg Arg Phe Xaa Asp Lys Leu Asn Phe Arg Gln
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (6)..(6)
<223> OTHER INFORMATION: Any non-natural amino acid
<220> FEATURE:
<221> NAME/KEY: MOD_RES
<222> LOCATION: (10)..(10)
<223> OTHER INFORMATION: Any non-natural amino acid

<400> SEQUENCE: 53

Xaa Ala Thr Gln Leu Xaa Arg Phe Gly Xaa Lys Leu Asn Phe Arg Gln
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (7)..(7)
<223> OTHER INFORMATION: Any non-natural amino acid
<220> FEATURE:
<221> NAME/KEY: MOD_RES
<222> LOCATION: (11)..(11)
<223> OTHER INFORMATION: Any non-natural amino acid

<400> SEQUENCE: 54
```

Xaa Ala Thr Gln Leu Arg Xaa Phe Gly Asp Xaa Leu Asn Phe Arg Gln
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (8)..(8)
<223> OTHER INFORMATION: Any non-natural amino acid
<220> FEATURE:
<221> NAME/KEY: MOD_RES
<222> LOCATION: (12)..(12)
<223> OTHER INFORMATION: Any non-natural amino acid

<400> SEQUENCE: 55

Xaa Ala Thr Gln Leu Arg Arg Xaa Gly Asp Lys Xaa Asn Phe Arg Gln
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (9)..(9)
<223> OTHER INFORMATION: Any non-natural amino acid
<220> FEATURE:
<221> NAME/KEY: MOD_RES
<222> LOCATION: (13)..(13)
<223> OTHER INFORMATION: Any non-natural amino acid

<400> SEQUENCE: 56

Xaa Ala Thr Gln Leu Arg Arg Phe Xaa Asp Lys Leu Xaa Phe Arg Gln
1               5                   10                  15

<210> SEQ ID NO 57
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: MOD_RES
<222> LOCATION: (14)..(14)
<223> OTHER INFORMATION: Any non-natural amino acid

```
<400> SEQUENCE: 57

Xaa Ala Thr Gln Leu Arg Arg Phe Gly Xaa Lys Leu Asn Xaa Arg Gln
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (12)..(12)
<223> OTHER INFORMATION: Any non-natural amino acid
<220> FEATURE:
<221> NAME/KEY: MOD_RES
<222> LOCATION: (16)..(16)
<223> OTHER INFORMATION: Any non-natural amino acid

<400> SEQUENCE: 58

Xaa Ala Thr Gln Leu Arg Arg Phe Gly Asp Lys Xaa Asn Phe Arg Xaa
1               5                   10                  15

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (13)..(13)
<223> OTHER INFORMATION: Any non-natural amino acid
<220> FEATURE:
<221> NAME/KEY: MOD_RES
<222> LOCATION: (17)..(17)
<223> OTHER INFORMATION: Any non-natural amino acid

<400> SEQUENCE: 59

Xaa Ala Thr Gln Leu Arg Arg Phe Gly Asp Lys Leu Xaa Phe Arg Gln
1               5                   10                  15

Xaa

<210> SEQ ID NO 60
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (2)..(2)
<223> OTHER INFORMATION: R-octenyl alanine
<220> FEATURE:
```

```
<221> NAME/KEY: MOD_RES
<222> LOCATION: (9)..(9)
<223> OTHER INFORMATION: Any non-natural amino acid

<400> SEQUENCE: 60

Xaa Ala Thr Gln Leu Arg Arg Phe Xaa Asp Lys Leu Asn Phe Arg Gln
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: Any non-natural amino acid

<400> SEQUENCE: 61

Xaa Ala Ala Gln Leu Arg Arg Phe Gly Xaa Lys Leu Asn Phe Arg Gln
1               5                   10                  15

<210> SEQ ID NO 62
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (4)..(4)
<223> OTHER INFORMATION: R-octenyl alanine
<220> FEATURE:
<221> NAME/KEY: MOD_RES
<222> LOCATION: (11)..(11)
<223> OTHER INFORMATION: Any non-natural amino acid

<400> SEQUENCE: 62

Xaa Ala Thr Ala Leu Arg Arg Phe Gly Asp Xaa Leu Asn Phe Arg Gln
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (5)..(5)
```

```
<223> OTHER INFORMATION: R-octenyl alanine
<220> FEATURE:
<221> NAME/KEY: MOD_RES
<222> LOCATION: (12)..(12)
<223> OTHER INFORMATION: Any non-natural amino acid

<400> SEQUENCE: 63

Xaa Ala Thr Gln Ala Arg Arg Phe Gly Asp Lys Xaa Asn Phe Arg Gln
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (6)..(6)
<223> OTHER INFORMATION: R-octenyl alanine
<220> FEATURE:
<221> NAME/KEY: MOD_RES
<222> LOCATION: (13)..(13)
<223> OTHER INFORMATION: Any non-natural amino acid

<400> SEQUENCE: 64

Xaa Ala Thr Gln Leu Ala Arg Phe Gly Asp Lys Leu Xaa Phe Arg Gln
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (7)..(7)
<223> OTHER INFORMATION: R-octenyl alanine
<220> FEATURE:
<221> NAME/KEY: MOD_RES
<222> LOCATION: (14)..(14)
<223> OTHER INFORMATION: Any non-natural amino acid

<400> SEQUENCE: 65

Xaa Ala Thr Gln Leu Arg Ala Phe Gly Asp Lys Leu Asn Xaa Arg Gln
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
```

<221> NAME/KEY: MOD_RES
<222> LOCATION: (8)..(8)
<223> OTHER INFORMATION: R-octenyl alanine
<220> FEATURE:
<221> NAME/KEY: MOD_RES
<222> LOCATION: (15)..(15)
<223> OTHER INFORMATION: Any non-natural amino acid

<400> SEQUENCE: 66

Xaa Ala Thr Gln Leu Arg Arg Ala Gly Asp Lys Leu Asn Phe Xaa Gln
1               5                   10                  15

<210> SEQ ID NO 67
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (9)..(9)
<223> OTHER INFORMATION: R-octenyl alanine
<220> FEATURE:
<221> NAME/KEY: MOD_RES
<222> LOCATION: (16)..(16)
<223> OTHER INFORMATION: Any non-natural amino acid

<400> SEQUENCE: 67

Xaa Ala Thr Gln Leu Arg Arg Phe Ala Asp Lys Leu Asn Phe Arg Xaa
1               5                   10                  15

<210> SEQ ID NO 68
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (2)..(2)
<223> OTHER INFORMATION: Any non-natural amino acid
<220> FEATURE:
<221> NAME/KEY: MOD_RES
<222> LOCATION: (6)..(6)
<223> OTHER INFORMATION: Any non-natural amino acid

<400> SEQUENCE: 68

Xaa Xaa Arg Gln Leu Xaa Ile Ile Gly Asp Asp Ile Asn Arg
1               5                   10

<210> SEQ ID NO 69
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid

```
         or not present
<220> FEATURE:
<221> NAME/KEY: MOD_RES
<222> LOCATION: (4)..(4)
<223> OTHER INFORMATION: Any non-natural amino acid
<220> FEATURE:
<221> NAME/KEY: MOD_RES
<222> LOCATION: (8)..(8)
<223> OTHER INFORMATION: Any non-natural amino acid

<400> SEQUENCE: 69

Xaa Gly Arg Xaa Leu Ala Ile Xaa Gly Asp Asp Ile Asn Arg
1               5                   10

<210> SEQ ID NO 70
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (5)..(5)
<223> OTHER INFORMATION: Any non-natural amino acid
<220> FEATURE:
<221> NAME/KEY: MOD_RES
<222> LOCATION: (9)..(9)
<223> OTHER INFORMATION: Any non-natural amino acid

<400> SEQUENCE: 70

Xaa Gly Arg Gln Xaa Ala Ile Ile Xaa Asp Asp Ile Asn Arg
1               5                   10

<210> SEQ ID NO 71
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (6)..(6)
<223> OTHER INFORMATION: Any non-natural amino acid
<220> FEATURE:
<221> NAME/KEY: MOD_RES
<222> LOCATION: (10)..(10)
<223> OTHER INFORMATION: Any non-natural amino acid

<400> SEQUENCE: 71

Xaa Gly Arg Gln Leu Xaa Ile Ile Gly Xaa Asp Ile Asn Arg
1               5                   10

<210> SEQ ID NO 72
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (7)..(7)
<223> OTHER INFORMATION: Any non-natural amino acid
<220> FEATURE:
<221> NAME/KEY: MOD_RES
<222> LOCATION: (11)..(11)
<223> OTHER INFORMATION: Any non-natural amino acid

<400> SEQUENCE: 72

Xaa Gly Arg Gln Leu Ala Xaa Ile Gly Asp Xaa Ile Asn Arg
1               5                   10

<210> SEQ ID NO 73
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (8)..(8)
<223> OTHER INFORMATION: Any non-natural amino acid
<220> FEATURE:
<221> NAME/KEY: MOD_RES
<222> LOCATION: (12)..(12)
<223> OTHER INFORMATION: Any non-natural amino acid

<400> SEQUENCE: 73

Xaa Gly Arg Gln Leu Ala Ile Xaa Gly Asp Asp Xaa Asn Arg
1               5                   10

<210> SEQ ID NO 74
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (9)..(9)
<223> OTHER INFORMATION: Any non-natural amino acid
<220> FEATURE:
<221> NAME/KEY: MOD_RES
<222> LOCATION: (13)..(13)
<223> OTHER INFORMATION: Any non-natural amino acid

<400> SEQUENCE: 74

Xaa Gly Arg Gln Leu Ala Ile Ile Xaa Asp Asp Ile Xaa Arg
1               5                   10

<210> SEQ ID NO 75
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: MOD_RES
<222> LOCATION: (14)..(14)
<223> OTHER INFORMATION: Any non-natural amino acid

<400> SEQUENCE: 75

Xaa Gly Arg Gln Leu Ala Ile Ile Gly Xaa Asp Ile Asn Xaa
1               5                   10

<210> SEQ ID NO 76
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (11)..(11)
<223> OTHER INFORMATION: Any non-natural amino acid
<220> FEATURE:
<221> NAME/KEY: MOD_RES
<222> LOCATION: (15)..(15)
<223> OTHER INFORMATION: Any non-natural amino acid

<400> SEQUENCE: 76

Xaa Gly Arg Gln Leu Ala Ile Ile Gly Asp Xaa Ile Asn Arg Xaa
1               5                   10                  15

<210> SEQ ID NO 77
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (2)..(2)
<223> OTHER INFORMATION: R-octenyl alanine
<220> FEATURE:
<221> NAME/KEY: MOD_RES
<222> LOCATION: (9)..(9)
<223> OTHER INFORMATION: Any non-natural amino acid

<400> SEQUENCE: 77

Xaa Ala Arg Gln Leu Ala Ile Ile Xaa Asp Asp Ile Asn Arg
1               5                   10

<210> SEQ ID NO 78
<211> LENGTH: 14
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: Any non-natural amino acid

<400> SEQUENCE: 78

Xaa Gly Ala Gln Leu Ala Ile Ile Gly Xaa Asp Ile Asn Arg
1               5                   10

<210> SEQ ID NO 79
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (4)..(4)
<223> OTHER INFORMATION: R-octenyl alanine
<220> FEATURE:
<221> NAME/KEY: MOD_RES
<222> LOCATION: (11)..(11)
<223> OTHER INFORMATION: Any non-natural amino acid

<400> SEQUENCE: 79

Xaa Gly Arg Ala Leu Ala Ile Ile Gly Asp Xaa Ile Asn Arg
1               5                   10

<210> SEQ ID NO 80
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (5)..(5)
<223> OTHER INFORMATION: R-octenyl alanine
<220> FEATURE:
<221> NAME/KEY: MOD_RES
<222> LOCATION: (12)..(12)
<223> OTHER INFORMATION: Any non-natural amino acid

<400> SEQUENCE: 80

Xaa Gly Arg Gln Ala Ala Ile Ile Gly Asp Asp Xaa Asn Arg
1               5                   10

<210> SEQ ID NO 81
<211> LENGTH: 14
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (6)..(6)
<223> OTHER INFORMATION: R-octenyl alanine
<220> FEATURE:
<221> NAME/KEY: MOD_RES
<222> LOCATION: (13)..(13)
<223> OTHER INFORMATION: Any non-natural amino acid

<400> SEQUENCE: 81

Xaa Gly Arg Gln Leu Ala Ile Ile Gly Asp Asp Ile Xaa Arg
1               5                   10

<210> SEQ ID NO 82
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (7)..(7)
<223> OTHER INFORMATION: R-octenyl alanine
<220> FEATURE:
<221> NAME/KEY: MOD_RES
<222> LOCATION: (14)..(14)
<223> OTHER INFORMATION: Any non-natural amino acid

<400> SEQUENCE: 82

Xaa Gly Arg Gln Leu Ala Ala Ile Gly Asp Asp Ile Asn Xaa
1               5                   10

<210> SEQ ID NO 83
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (8)..(8)
<223> OTHER INFORMATION: R-octenyl alanine
<220> FEATURE:
<221> NAME/KEY: MOD_RES
<222> LOCATION: (15)..(15)
<223> OTHER INFORMATION: Any non-natural amino acid

<400> SEQUENCE: 83

Xaa Gly Arg Gln Leu Ala Ile Ala Gly Asp Asp Ile Asn Arg Xaa
1               5                   10                  15

<210> SEQ ID NO 84
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (3)..(3)
<223> OTHER INFORMATION: Any non-natural amino acid
<220> FEATURE:
<221> NAME/KEY: MOD_RES
<222> LOCATION: (7)..(7)
<223> OTHER INFORMATION: Any non-natural amino acid

<400> SEQUENCE: 84

Xaa Val Xaa Arg Gln Leu Xaa Ile Ile Gly Asp Asp Ile Asn Arg
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (4)..(4)
<223> OTHER INFORMATION: Any non-natural amino acid
<220> FEATURE:
<221> NAME/KEY: MOD_RES
<222> LOCATION: (8)..(8)
<223> OTHER INFORMATION: Any non-natural amino acid

<400> SEQUENCE: 85

Xaa Val Gly Xaa Gln Leu Ala Xaa Ile Gly Asp Asp Ile Asn Arg
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (5)..(5)
<223> OTHER INFORMATION: Any non-natural amino acid
<220> FEATURE:
<221> NAME/KEY: MOD_RES
<222> LOCATION: (9)..(9)
<223> OTHER INFORMATION: Any non-natural amino acid

<400> SEQUENCE: 86

Xaa Val Gly Arg Xaa Leu Ala Ile Xaa Gly Asp Asp Ile Asn Arg
1               5                   10                  15
```

```
<210> SEQ ID NO 87
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (6)..(6)
<223> OTHER INFORMATION: Any non-natural amino acid
<220> FEATURE:
<221> NAME/KEY: MOD_RES
<222> LOCATION: (10)..(10)
<223> OTHER INFORMATION: Any non-natural amino acid

<400> SEQUENCE: 87

Xaa Val Gly Arg Gln Xaa Ala Ile Ile Xaa Asp Asp Ile Asn Arg
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (7)..(7)
<223> OTHER INFORMATION: Any non-natural amino acid
<220> FEATURE:
<221> NAME/KEY: MOD_RES
<222> LOCATION: (11)..(11)
<223> OTHER INFORMATION: Any non-natural amino acid

<400> SEQUENCE: 88

Xaa Val Gly Arg Gln Leu Xaa Ile Ile Gly Xaa Asp Ile Asn Arg
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (8)..(8)
<223> OTHER INFORMATION: Any non-natural amino acid
<220> FEATURE:
<221> NAME/KEY: MOD_RES
<222> LOCATION: (12)..(12)
<223> OTHER INFORMATION: Any non-natural amino acid

<400> SEQUENCE: 89

Xaa Val Gly Arg Gln Leu Ala Xaa Ile Gly Asp Xaa Ile Asn Arg
```

<210> SEQ ID NO 90
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (9)..(9)
<223> OTHER INFORMATION: Any non-natural amino acid
<220> FEATURE:
<221> NAME/KEY: MOD_RES
<222> LOCATION: (13)..(13)
<223> OTHER INFORMATION: Any non-natural amino acid

<400> SEQUENCE: 90

Xaa Val Gly Arg Gln Leu Ala Ile Xaa Gly Asp Asp Xaa Asn Arg
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: MOD_RES
<222> LOCATION: (14)..(14)
<223> OTHER INFORMATION: Any non-natural amino acid

<400> SEQUENCE: 91

Xaa Val Gly Arg Gln Leu Ala Ile Ile Xaa Asp Asp Ile Xaa Arg
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (11)..(11)
<223> OTHER INFORMATION: Any non-natural amino acid
<220> FEATURE:
<221> NAME/KEY: MOD_RES
<222> LOCATION: (15)..(15)
<223> OTHER INFORMATION: Any non-natural amino acid

<400> SEQUENCE: 92

```
Xaa Val Gly Arg Gln Leu Ala Ile Ile Gly Xaa Asp Ile Asn Xaa
1               5                   10                  15
```

<210> SEQ ID NO 93
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (12)..(12)
<223> OTHER INFORMATION: Any non-natural amino acid
<220> FEATURE:
<221> NAME/KEY: MOD_RES
<222> LOCATION: (16)..(16)
<223> OTHER INFORMATION: Any non-natural amino acid

<400> SEQUENCE: 93

```
Xaa Val Gly Arg Gln Leu Ala Ile Ile Gly Asp Xaa Ile Asn Arg Xaa
1               5                   10                  15
```

<210> SEQ ID NO 94
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: Any non-natural amino acid

<400> SEQUENCE: 94

```
Xaa Val Ala Arg Gln Leu Ala Ile Ile Xaa Asp Asp Ile Asn Arg
1               5                   10                  15
```

<210> SEQ ID NO 95
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (4)..(4)
<223> OTHER INFORMATION: R-octenyl alanine
<220> FEATURE:
<221> NAME/KEY: MOD_RES
<222> LOCATION: (11)..(11)
<223> OTHER INFORMATION: Any non-natural amino acid

<400> SEQUENCE: 95

Xaa Val Gly Ala Gln Leu Ala Ile Ile Gly Xaa Asp Ile Asn Arg
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (5)..(5)
<223> OTHER INFORMATION: R-octenyl alanine
<220> FEATURE:
<221> NAME/KEY: MOD_RES
<222> LOCATION: (12)..(12)
<223> OTHER INFORMATION: Any non-natural amino acid

<400> SEQUENCE: 96

Xaa Val Gly Arg Ala Leu Ala Ile Ile Gly Asp Xaa Ile Asn Arg
1               5                   10                  15

<210> SEQ ID NO 97
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (6)..(6)
<223> OTHER INFORMATION: R-octenyl alanine
<220> FEATURE:
<221> NAME/KEY: MOD_RES
<222> LOCATION: (13)..(13)
<223> OTHER INFORMATION: Any non-natural amino acid

<400> SEQUENCE: 97

Xaa Val Gly Arg Gln Ala Ala Ile Ile Gly Asp Asp Xaa Asn Arg
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (7)..(7)
<223> OTHER INFORMATION: R-octenyl alanine
<220> FEATURE:
<221> NAME/KEY: MOD_RES -continued
<222> LOCATION: (14)..(14)
<223> OTHER INFORMATION: Any non-natural amino acid

<400> SEQUENCE: 98

Xaa Val Gly Arg Gln Leu Ala Ile Ile Gly Asp Asp Ile Xaa Arg
1               5                   10                  15

<210> SEQ ID NO 99
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (8)..(8)
<223> OTHER INFORMATION: R-octenyl alanine
<220> FEATURE:
<221> NAME/KEY: MOD_RES
<222> LOCATION: (15)..(15)
<223> OTHER INFORMATION: Any non-natural amino acid

<400> SEQUENCE: 99

Xaa Val Gly Arg Gln Leu Ala Ala Ile Gly Asp Asp Ile Asn Xaa
1               5                   10                  15

<210> SEQ ID NO 100
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (9)..(9)
<223> OTHER INFORMATION: R-octenyl alanine
<220> FEATURE:
<221> NAME/KEY: MOD_RES
<222> LOCATION: (16)..(16)
<223> OTHER INFORMATION: Any non-natural amino acid

<400> SEQUENCE: 100

Xaa Val Gly Arg Gln Leu Ala Ile Ala Gly Asp Asp Ile Asn Arg Xaa
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (2)..(2)
<223> OTHER INFORMATION: Any non-natural amino acid

```
<220> FEATURE:
<221> NAME/KEY: MOD_RES
<222> LOCATION: (6)..(6)
<223> OTHER INFORMATION: Any non-natural amino acid

<400> SEQUENCE: 101

Xaa Xaa Ser Glu Ser Xaa Lys Arg Ile Gly Asp Glu Leu Asp Ser
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (3)..(3)
<223> OTHER INFORMATION: Any non-natural amino acid
<220> FEATURE:
<221> NAME/KEY: MOD_RES
<222> LOCATION: (7)..(7)
<223> OTHER INFORMATION: Any non-natural amino acid

<400> SEQUENCE: 102

Xaa Leu Xaa Glu Ser Leu Xaa Arg Ile Gly Asp Glu Leu Asp Ser
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (4)..(4)
<223> OTHER INFORMATION: Any non-natural amino acid
<220> FEATURE:
<221> NAME/KEY: MOD_RES
<222> LOCATION: (8)..(8)
<223> OTHER INFORMATION: Any non-natural amino acid

<400> SEQUENCE: 103

Xaa Leu Ser Xaa Ser Leu Lys Xaa Ile Gly Asp Glu Leu Asp Ser
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
```

```
<222> LOCATION: (5)..(5)
<223> OTHER INFORMATION: Any non-natural amino acid
<220> FEATURE:
<221> NAME/KEY: MOD_RES
<222> LOCATION: (9)..(9)
<223> OTHER INFORMATION: Any non-natural amino acid

<400> SEQUENCE: 104

Xaa Leu Ser Glu Xaa Leu Lys Arg Xaa Gly Asp Glu Leu Asp Ser
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (6)..(6)
<223> OTHER INFORMATION: Any non-natural amino acid
<220> FEATURE:
<221> NAME/KEY: MOD_RES
<222> LOCATION: (10)..(10)
<223> OTHER INFORMATION: Any non-natural amino acid

<400> SEQUENCE: 105

Xaa Leu Ser Glu Ser Xaa Lys Arg Ile Xaa Asp Glu Leu Asp Ser
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (7)..(7)
<223> OTHER INFORMATION: Any non-natural amino acid
<220> FEATURE:
<221> NAME/KEY: MOD_RES
<222> LOCATION: (11)..(11)
<223> OTHER INFORMATION: Any non-natural amino acid

<400> SEQUENCE: 106

Xaa Leu Ser Glu Ser Leu Xaa Arg Ile Gly Xaa Glu Leu Asp Ser
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
```

```
<220> FEATURE:
<221> NAME/KEY: MOD_RES
<222> LOCATION: (8)..(8)
<223> OTHER INFORMATION: Any non-natural amino acid
<220> FEATURE:
<221> NAME/KEY: MOD_RES
<222> LOCATION: (12)..(12)
<223> OTHER INFORMATION: Any non-natural amino acid

<400> SEQUENCE: 107

Xaa Leu Ser Glu Ser Leu Lys Xaa Ile Gly Asp Xaa Leu Asp Ser
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (9)..(9)
<223> OTHER INFORMATION: Any non-natural amino acid
<220> FEATURE:
<221> NAME/KEY: MOD_RES
<222> LOCATION: (13)..(13)
<223> OTHER INFORMATION: Any non-natural amino acid

<400> SEQUENCE: 108

Xaa Leu Ser Glu Ser Leu Lys Arg Xaa Gly Asp Glu Xaa Asp Ser
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: MOD_RES
<222> LOCATION: (14)..(14)
<223> OTHER INFORMATION: Any non-natural amino acid

<400> SEQUENCE: 109

Xaa Leu Ser Glu Ser Leu Lys Arg Ile Xaa Asp Glu Leu Xaa Ser
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Non-natural electrophile containing amino acid
      or not present
<220> FEATURE:
<221> NAME/KEY: MOD_RES
<222> LOCATION: (11)..(11)
<223> OTHER INFORMATION: Any non-natural amino acid
<220> FEATURE:
<221> NAME/KEY: MOD_RES
<222> LOCATION: (15)..(15)
<223> OTHER INFORMATION: Any non-natural amino acid

<400> SEQUENCE: 110

Xaa Leu Ser Glu Ser Leu Lys Arg Ile Gly Xaa Glu Leu Asp Xaa
1               5                   10                  15

<210> SEQ ID NO 111
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (12)..(12)
<223> OTHER INFORMATION: Any non-natural amino acid
<220> FEATURE:
<221> NAME/KEY: MOD_RES
<222> LOCATION: (16)..(16)
<223> OTHER INFORMATION: Any non-natural amino acid

<400> SEQUENCE: 111

Xaa Leu Ser Glu Ser Leu Lys Arg Ile Gly Asp Xaa Leu Asp Ser Xaa
1               5                   10                  15

<210> SEQ ID NO 112
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (2)..(2)
<223> OTHER INFORMATION: R-octenyl alanine
<220> FEATURE:
<221> NAME/KEY: MOD_RES
<222> LOCATION: (9)..(9)
<223> OTHER INFORMATION: Any non-natural amino acid

<400> SEQUENCE: 112

Xaa Ala Ser Glu Ser Leu Lys Arg Xaa Gly Asp Glu Leu Asp Ser
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

-continued

```
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (3)..(3)
<223> OTHER INFORMATION: R-octenyl alanine
<220> FEATURE:
<221> NAME/KEY: MOD_RES
<222> LOCATION: (10)..(10)
<223> OTHER INFORMATION: Any non-natural amino acid

<400> SEQUENCE: 113

Xaa Leu Ala Glu Ser Leu Lys Arg Ile Xaa Asp Glu Leu Asp Ser
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (4)..(4)
<223> OTHER INFORMATION: R-octenyl alanine
<220> FEATURE:
<221> NAME/KEY: MOD_RES
<222> LOCATION: (11)..(11)
<223> OTHER INFORMATION: Any non-natural amino acid

<400> SEQUENCE: 114

Xaa Leu Ser Ala Ser Leu Lys Arg Ile Gly Xaa Glu Leu Asp Ser
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (5)..(5)
<223> OTHER INFORMATION: R-octenyl alanine
<220> FEATURE:
<221> NAME/KEY: MOD_RES
<222> LOCATION: (12)..(12)
<223> OTHER INFORMATION: Any non-natural amino acid

<400> SEQUENCE: 115

Xaa Leu Ser Glu Ala Leu Lys Arg Ile Gly Asp Xaa Leu Asp Ser
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Description of Artificial Sequence: Synthetic
```

```
       peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (6)..(6)
<223> OTHER INFORMATION: R-octenyl alanine
<220> FEATURE:
<221> NAME/KEY: MOD_RES
<222> LOCATION: (13)..(13)
<223> OTHER INFORMATION: Any non-natural amino acid

<400> SEQUENCE: 116

Xaa Leu Ser Glu Ser Ala Lys Arg Ile Gly Asp Glu Xaa Asp Ser
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (7)..(7)
<223> OTHER INFORMATION: R-octenyl alanine
<220> FEATURE:
<221> NAME/KEY: MOD_RES
<222> LOCATION: (14)..(14)
<223> OTHER INFORMATION: Any non-natural amino acid

<400> SEQUENCE: 117

Xaa Leu Ser Glu Ser Leu Ala Arg Ile Gly Asp Glu Leu Xaa Ser
1               5                   10                  15

<210> SEQ ID NO 118
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (8)..(8)
<223> OTHER INFORMATION: R-octenyl alanine
<220> FEATURE:
<221> NAME/KEY: MOD_RES
<222> LOCATION: (15)..(15)
<223> OTHER INFORMATION: Any non-natural amino acid

<400> SEQUENCE: 118

Xaa Leu Ser Glu Ser Leu Lys Ala Ile Gly Asp Glu Leu Asp Xaa
1               5                   10                  15

<210> SEQ ID NO 119
<211> LENGTH: 16
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
<220> FEATURE:
<221> NAME/KEY: MOD_RES
<222> LOCATION: (9)..(9)
<223> OTHER INFORMATION: R-octenyl alanine
<220> FEATURE:
<221> NAME/KEY: MOD_RES
<222> LOCATION: (16)..(16)
<223> OTHER INFORMATION: Any non-natural amino acid

<400> SEQUENCE: 119

Xaa Leu Ser Glu Ser Leu Lys Arg Ala Gly Asp Glu Leu Asp Ser Xaa
1               5                   10                  15

<210> SEQ ID NO 120

<400> SEQUENCE: 120

000

<210> SEQ ID NO 121
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ala Thr Gln Leu Arg Arg Phe Gly Asp Lys Leu Asn Phe Arg Gln
1               5                   10                  15

<210> SEQ ID NO 122
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ala Glu Leu Glu Val Glu Cys Ala Thr Gln Leu Arg Arg Phe Gly Asp
1               5                   10                  15

Lys Leu Asn Phe Arg Gln Lys Leu Leu Asn
            20                  25

<210> SEQ ID NO 123
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Glu Ile Trp Ile Ala Gln Glu Leu Arg Arg Ile Gly Asp Glu Phe Asn
1               5                   10                  15

Ala Tyr Tyr Ala Arg Arg
            20

<210> SEQ ID NO 124
```

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Asp Ile Ile Arg Asn Ile Ala Arg His Leu Ala Gln Val Gly Asp Ser
1               5                   10                  15

Met Asp Arg Ser Ile
            20

<210> SEQ ID NO 125
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ser Ser Thr Met Gly Gln Val Gly Arg Gln Leu Ala Ile Ile Gly Asp
1               5                   10                  15

Asp Ile Asn Arg Arg Tyr
            20

<210> SEQ ID NO 126
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gln Asp Ala Ser Thr Lys Lys Leu Ser Glu Ser Leu Lys Arg Ile Gly
1               5                   10                  15

Asp Glu Leu Asp Ser Asn Met Glu Leu
            20                  25

<210> SEQ ID NO 127
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Arg Leu Ala Glu Val Cys Ala Val Leu Leu Arg Leu Gly Asp Glu Leu
1               5                   10                  15

Glu Met Ile Arg
            20

<210> SEQ ID NO 128
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present
```

<400> SEQUENCE: 128

Xaa Ala Thr Gln Leu Arg Arg Phe Gly Asp Lys Leu Asn Phe Arg Gln
1               5                   10                  15

Lys Leu Leu

<210> SEQ ID NO 129
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present

<400> SEQUENCE: 129

Xaa Glu Val Glu Ser Ala Thr Gln Leu Arg Arg Phe Gly Asp Lys Leu
1               5                   10                  15

Asn Phe Arg Gln Lys Leu Leu
                20

<210> SEQ ID NO 130
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
      or not present

<400> SEQUENCE: 130

Xaa Ile Ala Gln Glu Leu Arg Arg Ile Gly Asp Glu Phe Asn Ala Tyr
1               5                   10                  15

Tyr Ala Arg Arg
                20

<210> SEQ ID NO 131
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ala Thr Gln Leu Arg Arg Phe Gly Asp Lys Leu Asn Phe Arg Gln
1               5                   10                  15

<210> SEQ ID NO 132
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ile Ala Gln Glu Leu Arg Arg Ile Gly Asp Glu Phe Asn Ala Tyr Tyr
1               5                   10                  15

Ala Arg Arg

<210> SEQ ID NO 133
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ala Arg His Leu Ala Gln Val Gly Asp Ser Met Asp Arg
1               5                   10

<210> SEQ ID NO 134
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gly Arg Gln Leu Ala Ile Ile Gly Asp Asp Ile Asn Arg
1               5                   10

<210> SEQ ID NO 135
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Leu Ser Glu Ser Leu Lys Arg Ile Gly Asp Glu Leu Asp Ser
1               5                   10

<210> SEQ ID NO 136
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Cys Ala Val Leu Leu Arg Leu Gly Asp Glu Leu Glu Met
1               5                   10

<210> SEQ ID NO 137
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid

<400> SEQUENCE: 137

Xaa Glu Val Glu Ser Ala Thr Gln Leu Arg
1               5                   10

<210> SEQ ID NO 138

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid

<400> SEQUENCE: 138

Xaa Ala Thr Gln Leu Arg
1               5

<210> SEQ ID NO 139
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid

<400> SEQUENCE: 139

Xaa Val Glu Ser Ala Thr Gln Leu Arg
1               5

<210> SEQ ID NO 140
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid

<400> SEQUENCE: 140

Xaa Glu Ser Ala Thr Gln Leu Arg
1               5

<210> SEQ ID NO 141
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid

<400> SEQUENCE: 141

Xaa Ser Ala Thr Gln Leu Arg
1               5

<210> SEQ ID NO 142
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (5)..(5)
<223> OTHER INFORMATION: Any cell permeability enhancing amino acid
      (e.g., amino acids that change or shift the distribution of charge
      or hydrophobic character) or a stability enhancing amino acid (
      e.g., non- native, D, or alpha methyl amino acid point mutations)

<400> SEQUENCE: 142

Leu Asn Phe Arg Xaa
1               5

<210> SEQ ID NO 143
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any cell permeability enhancing amino acid
      (e.g., amino acids that change or shift the distribution of charge
      or hydrophobic character) or a stability enhancing amino acid
      (e.g., non- native, D, or alpha methyl amino acid point mutations)

<400> SEQUENCE: 143

Leu Asn Phe Arg Gln Xaa
1               5

<210> SEQ ID NO 144
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any cell permeability enhancing amino acid
      (e.g., amino acids that change or shift the distribution of charge
      or hydrophobic character) or a stability enhancing amino acid
      (e.g., non- native, D, or alpha methyl amino acid point mutations)

<400> SEQUENCE: 144

Leu Asn Phe Arg Gln Lys Xaa
1               5

<210> SEQ ID NO 145
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any cell permeability enhancing amino acid
      (e.g., amino acids that change or shift the distribution of charge
      or hydrophobic character) or a stability enhancing amino acid
      (e.g., non- native, D, or alpha methyl amino acid point mutations)

<400> SEQUENCE: 145

Leu Asn Phe Arg Gln Lys Leu Leu Xaa
1               5

<210> SEQ ID NO 146
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any cell permeability enhancing amino acid
      (e.g., amino acids that change or shift the distribution of charge
      or hydrophobic character) or a stability enhancing amino acid
      (e.g., non-native, D, or alpha methyl amino acid point mutations)

<400> SEQUENCE: 146

Leu Asn Phe Arg Gln Lys Leu Leu Lys Xaa
1               5                   10

<210> SEQ ID NO 147
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid

<400> SEQUENCE: 147

Xaa Ile Ala Gln Glu Leu Arg
1               5

<210> SEQ ID NO 148
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid

<400> SEQUENCE: 148

Xaa Ala Gln Glu Leu Arg
1               5

<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid

<400> SEQUENCE: 149

Xaa Ala Gln Glu Leu Arg Arg
1               5

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (9)..(9)
<223> OTHER INFORMATION: Any cell permeability enhancing amino acid
      (e.g., amino acids that change or shift the distribution of charge
      or hydrophobic character) or a stability enhancing amino acid
      (e.g., non- native, D, or alpha methyl amino acid point mutations)

<400> SEQUENCE: 150

Phe Asn Ala Tyr Tyr Ala Arg Lys Xaa
1               5

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any cell permeability enhancing amino acid
      (e.g., amino acids that change or shift the distribution of charge
      or hydrophobic character) or a stability enhancing amino acid
      (e.g., non- native, D, or alpha methyl amino acid point mutations)

<400> SEQUENCE: 151

Phe Asn Ala Tyr Tyr Ala Arg Arg Xaa
1               5

<210> SEQ ID NO 152
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid

<400> SEQUENCE: 152

Xaa Leu Ser Glu Ser Leu Lys
1               5

<210> SEQ ID NO 153
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid

<400> SEQUENCE: 153

Xaa Ser Glu Ser Leu Lys
1               5

<210> SEQ ID NO 154
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (6)..(6)
<223> OTHER INFORMATION: Any cell permeability enhancing amino acid
      (e.g., amino acids that change or shift the distribution of charge
      or hydrophobic character) or a stability enhancing amino acid
      (e.g., non- native, D, or alpha methyl amino acid point mutations)

<400> SEQUENCE: 154

Leu Asp Ser Asn Lys Xaa
1               5

<210> SEQ ID NO 155
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any cell permeability enhancing amino acid
      (e.g., amino acids that change or shift the distribution of charge
      or hydrophobic character) or a stability enhancing amino acid
      (e.g., non- native, D, or alpha methyl amino acid point mutations)

<400> SEQUENCE: 155

Leu Asp Ser Asn Xaa
1               5

<210> SEQ ID NO 156
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any cell permeability enhancing amino acid
      (e.g., amino acids that change or shift the distribution of
      charge or hydrophobic character) or a stability enhancing amino
      acid (e.g., non- native, D, or alpha methyl amino acid point
      mutations)

<400> SEQUENCE: 156

Ile Gly Asp Asp Ile Asn Arg Arg Xaa
1               5

<210> SEQ ID NO 157
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any cell permeability enhancing amino acid
      (e.g., amino acids that change or shift the distribution of charge
      or hydrophobic
      character) or a stability enhancing amino acid (e.g., non-
      native, D, or alpha methyl amino acid point mutations)

<400> SEQUENCE: 157

Ile Gly Asp Asp Ile Asn Arg Xaa
1               5

<210> SEQ ID NO 158
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid

<400> SEQUENCE: 158

Xaa Pro Gly Gly Arg Leu Ala Glu Val Cys Thr Val Leu Leu Arg
1               5                   10                  15

<210> SEQ ID NO 159
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid

<400> SEQUENCE: 159

Xaa Gly Gly Arg Leu Ala Glu Val Cys Thr Val Leu Leu Arg
1               5                   10

<210> SEQ ID NO 160
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any cell permeability enhancing amino acid
      (e.g., amino acids that change or shift the distribution of charge
      or hydrophobic character) or a stability enhancing amino acid
      (e.g., non- native, D, or alpha methyl amino acid point mutations)

<400> SEQUENCE: 160

Glu Leu Glu Gln Ile Arg Pro Ser Xaa
1               5

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any cell permeability enhancing amino acid
      (e.g., amino acids that change or shift the distribution of charge
      or hydrophobic character) or a stability enhancing amino acid
      (e.g., non- native, D, or alpha methyl amino acid point mutations)

<400> SEQUENCE: 161

Glu Leu Glu Gln Ile Arg Xaa
1               5

<210> SEQ ID NO 162
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid

<400> SEQUENCE: 162

Xaa Asp Ile Ile Arg Asn Ile Ala Arg His Leu Ala
1               5                   10

<210> SEQ ID NO 163
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid

<400> SEQUENCE: 163

Xaa Ile Ile Arg Asn Ile Ala Arg His Leu Ala
1               5                   10

<210> SEQ ID NO 164
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (6)..(6)
<223> OTHER INFORMATION: Any cell permeability enhancing amino acid
      (e.g., amino acids that change or shift the distribution of charge
      or hydrophobic character) or a stability enhancing amino acid
      (e.g., non- native, D, or alpha methyl amino acid point mutations)

<400> SEQUENCE: 164

Xaa Asp Arg Ser Ile Xaa
1               5

<210> SEQ ID NO 165
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (7)..(7)
<223> OTHER INFORMATION: Any cell permeability enhancing amino acid
      (e.g., amino acids that change or shift the distribution of charge
      or hydrophobic character) or a stability enhancing amino acid
      (e.g., non- native, D, or alpha methyl amino acid point mutations)

<400> SEQUENCE: 165
```

```
Xaa Asp Arg Ser Ile Arg Xaa
1               5
```

<210> SEQ ID NO 166
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid

<400> SEQUENCE: 166

```
Xaa Glu Gln Trp Ala Arg Glu Ile Gly Ala Gln Leu Arg
1               5                   10
```

<210> SEQ ID NO 167
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid

<400> SEQUENCE: 167

```
Xaa Gln Trp Ala Arg Glu Ile Gly Ala Gln Leu Arg
1               5                   10
```

<210> SEQ ID NO 168
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid

<400> SEQUENCE: 168

```
Xaa Arg Glu Ile Gly Ala Gln Leu Arg
1               5
```

<210> SEQ ID NO 169
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid

<400> SEQUENCE: 169

```
Xaa Glu Ile Gly Ala Gln Leu Arg
1               5
```

<210> SEQ ID NO 170
<211> LENGTH: 6

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any cell permeability enhancing amino acid
      (e.g., amino acids that change or shift the distribution of charge
      or hydrophobic character) or a stability enhancing amino acid
      (e.g., non- native, D, or alpha methyl amino acid point mutations)

<400> SEQUENCE: 170

Leu Asn Ala Gln Tyr Xaa
1               5

<210> SEQ ID NO 171
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any cell permeability enhancing amino acid
      (e.g., amino acids that change or shift the distribution of charge
      or hydrophobic character) or a stability enhancing amino acid
      (e.g., non- native, D, or alpha methyl amino acid point mutations)

<400> SEQUENCE: 171

Leu Asn Ala Gln Tyr Glu Xaa
1               5

<210> SEQ ID NO 172
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any cell permeability enhancing amino acid
      (e.g., amino acids that change or shift the distribution of charge
      or hydrophobic character) or a stability enhancing amino acid
      (e.g., non- native, D, or alpha methyl amino acid point mutations)

<400> SEQUENCE: 172

Leu Asn Phe Arg Gln Lys Leu Xaa
1               5

<210> SEQ ID NO 173
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
<220> FEATURE:
<221> NAME/KEY: MISC_FEATURE
<222> LOCATION: (2)..(5)
<223> OTHER INFORMATION: May or may not be present
<220> FEATURE:
<221> NAME/KEY: MISC_FEATURE
<222> LOCATION: (2)..(10)
```

```
<223> OTHER INFORMATION: This region may encompass "EVESATQLR" or
      "VESATQLR" or "ESATQLR" or "SATQLR" or "ATQLR" wherein some
      positions may be absent
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (15)..(15)
<223> OTHER INFORMATION: Any amino acid
<220> FEATURE:
<221> NAME/KEY: MISC_FEATURE
<222> LOCATION: (16)..(24)
<223> OTHER INFORMATION: This region may encompass "LNFRQKLLK" or
      "LNFRQKLL" or "LNFRQKL" or "LNFRQK" or "LNFRQ" or "LNFR"
      wherein some positions may be absent
<220> FEATURE:
<221> NAME/KEY: MISC_FEATURE
<222> LOCATION: (20)..(24)
<223> OTHER INFORMATION: May or may not be present
<220> FEATURE:
<221> NAME/KEY: MOD_RES
<222> LOCATION: (25)..(25)
<223> OTHER INFORMATION: Any cell permeability enhancing amino acid
      (e.g., amino acids that change or shift the distribution of charge
      or hydrophobic character) or a stability enhancing amino acid
      (e.g., non- native, D, or alpha methyl amino acid point mutations)
<220> FEATURE:
<223> OTHER INFORMATION: See specification as filed for detailed
      description of substitutions and preferred embodiments

<400> SEQUENCE: 173

Xaa Glu Val Glu Ser Ala Thr Gln Leu Arg Xaa Phe Gly Asp Xaa Leu
1               5                   10                  15

Asn Phe Arg Gln Lys Leu Leu Lys Xaa
            20                  25

<210> SEQ ID NO 174
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
<220> FEATURE:
<221> NAME/KEY: MISC_FEATURE
<222> LOCATION: (2)..(2)
<223> OTHER INFORMATION: May or may not be present
<220> FEATURE:
<221> NAME/KEY: MISC_FEATURE
<222> LOCATION: (2)..(8)
<223> OTHER INFORMATION: This region may encompass "IAQELR" or "AQELR"
      or "AQELRR" wherein some positions may be absent
<220> FEATURE:
<221> NAME/KEY: MISC_FEATURE
<222> LOCATION: (8)..(8)
<223> OTHER INFORMATION: May or may not be present
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MISC_FEATURE
<222> LOCATION: (14)..(21)
<223> OTHER INFORMATION: This region may encompass "FNAYYARK" or
"FNAYYARR"
      wherein some positions may be absent
```

```
<220> FEATURE:
<221> NAME/KEY: MOD_RES
<222> LOCATION: (21)..(21)
<223> OTHER INFORMATION: Arg or Lys
<220> FEATURE:
<221> NAME/KEY: MOD_RES
<222> LOCATION: (22)..(22)
<223> OTHER INFORMATION: Any cell permeability enhancing amino acid
      (e.g., amino acids that change or shift the distribution of charge
      or hydrophobic character) or a stability enhancing amino acid
      (e.g., non- native, D, or alpha methyl amino acid point mutations)
<220> FEATURE:
<223> OTHER INFORMATION: See specification as filed for detailed
      description of substitutions and preferred embodiments

<400> SEQUENCE: 174

Xaa Ile Ala Gln Glu Leu Arg Arg Xaa Ile Gly Asp Xaa Phe Asn Ala
1               5                   10                  15

Tyr Tyr Ala Arg Xaa Xaa
            20

<210> SEQ ID NO 175
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
<220> FEATURE:
<221> NAME/KEY: MISC_FEATURE
<222> LOCATION: (2)..(2)
<223> OTHER INFORMATION: May or may not be present
<220> FEATURE:
<221> NAME/KEY: MISC_FEATURE
<222> LOCATION: (2)..(7)
<223> OTHER INFORMATION: This region may encompass “LSESLK” or “SESLK”
      wherein some positions may be absent
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MISC_FEATURE
<222> LOCATION: (13)..(17)
<223> OTHER INFORMATION: This region may encompass “LDSNK” or “LDSN”
      wherein some positions may be absent
<220> FEATURE:
<221> NAME/KEY: MISC_FEATURE
<222> LOCATION: (17)..(17)
<223> OTHER INFORMATION: May or may not be present
<220> FEATURE:
<221> NAME/KEY: MOD_RES
<222> LOCATION: (18)..(18)
<223> OTHER INFORMATION: Any cell permeability enhancing amino acid
      (e.g., amino acids that change or shift the distribution of charge
      or hydrophobic
      character) or a stability enhancing amino acid (e.g., non-
      native, D, or alpha methyl amino acid point mutations)
<220> FEATURE:
<223> OTHER INFORMATION: See specification as filed for detailed
      description of substitutions and preferred embodiments

<400> SEQUENCE: 175

Xaa Leu Ser Glu Ser Leu Lys Xaa Ile Gly Asp Xaa Leu Asp Ser Asn
1               5                   10                  15

Lys Xaa
```

```
<210> SEQ ID NO 176
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
<220> FEATURE:
<221> NAME/KEY: MISC_FEATURE
<222> LOCATION: (2)..(2)
<223> OTHER INFORMATION: May or may not be present
<220> FEATURE:
<221> NAME/KEY: MISC_FEATURE
<222> LOCATION: (2)..(3)
<223> OTHER INFORMATION: This region may encompass "VG" or "G"
      wherein some positions may be absent
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MISC_FEATURE
<222> LOCATION: (9)..(16)
<223> OTHER INFORMATION: This region may encompass "IGDDINRR" or
      "IGDDINR" wherein some positions may be absent
<220> FEATURE:
<221> NAME/KEY: MISC_FEATURE
<222> LOCATION: (16)..(16)
<223> OTHER INFORMATION: May or may not be present
<220> FEATURE:
<221> NAME/KEY: MOD_RES
<222> LOCATION: (17)..(17)
<223> OTHER INFORMATION: Any cell permeability enhancing amino acid
      (e.g., amino acids that change or shift the distribution of charge
      or hydrophobic character) or a stability enhancing amino acid
      (e.g., non- native, D, or alpha methyl amino acid point mutations)
<220> FEATURE:
<223> OTHER INFORMATION: See specification as filed for detailed
      description of substitutions and preferred embodiments

<400> SEQUENCE: 176

Xaa Val Gly Xaa Gln Leu Ala Xaa Ile Gly Asp Asp Ile Asn Arg Arg
1               5                   10                  15

Xaa

<210> SEQ ID NO 177
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
<220> FEATURE:
<221> NAME/KEY: MISC_FEATURE
<222> LOCATION: (2)..(2)
<223> OTHER INFORMATION: May or may not be present
<220> FEATURE:
<221> NAME/KEY: MISC_FEATURE
<222> LOCATION: (2)..(15)
<223> OTHER INFORMATION: This region may encompass "PGGRLAEVCTVLLR" or
      "GGRLAEVCTVLLR" wherein some positions may be absent
<220> FEATURE:
```

<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (20)..(20)
<223> OTHER INFORMATION: Any amino acid
<220> FEATURE:
<221> NAME/KEY: MISC_FEATURE
<222> LOCATION: (21)..(28)
<223> OTHER INFORMATION: This region may encompass "ELEQIRPS" or "ELEQIR" wherein some positions may be absent
<220> FEATURE:
<221> NAME/KEY: MISC_FEATURE
<222> LOCATION: (27)..(28)
<223> OTHER INFORMATION: May or may not be present
<220> FEATURE:
<221> NAME/KEY: MOD_RES
<222> LOCATION: (29)..(29)
<223> OTHER INFORMATION: Any cell permeability enhancing amino acid (e.g., amino acids that change or shift the distribution of charge or hydrophobic character) or a stability enhancing amino acid (e.g., non- native, D, or alpha methyl amino acid point mutations)
<220> FEATURE:
<223> OTHER INFORMATION: See specification as filed for detailed description of substitutions and preferred embodiments

<400> SEQUENCE: 177

Xaa Pro Gly Gly Arg Leu Ala Glu Val Cys Thr Val Leu Leu Arg Xaa
1               5                   10                  15

Leu Gly Asp Xaa Glu Leu Glu Gln Ile Arg Pro Ser Xaa
            20                  25

<210> SEQ ID NO 178
<211> LENGTH: 24
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(1)
<223> OTHER INFORMATION: Non-natural electrophile containing amino acid
<220> FEATURE:
<221> NAME/KEY: MISC_FEATURE
<222> LOCATION: (2)..(2)
<223> OTHER INFORMATION: May or may not be present
<220> FEATURE:
<221> NAME/KEY: MISC_FEATURE
<222> LOCATION: (2)..(12)
<223> OTHER INFORMATION: This region may encompass "DIIRNIARHLA" or "IIRNIARHLA" wherein some positions may be absent
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (18)..(18)
<223> OTHER INFORMATION: Norleucine
<220> FEATURE:
<221> NAME/KEY: MISC_FEATURE
<222> LOCATION: (18)..(23)
<223> OTHER INFORMATION: This region may encompass "BDRSIR" or "BDRSI" wherein B is norleucine and some positions may be absent
<220> FEATURE:
<221> NAME/KEY: MISC_FEATURE
<222> LOCATION: (23)..(23)
<223> OTHER INFORMATION: May or may not be present
<220> FEATURE:
<221> NAME/KEY: MOD_RES

```
<222> LOCATION: (24)..(24)
<223> OTHER INFORMATION: Any cell permeability enhancing amino acid
      (e.g., amino acids that change or shift the distribution of charge
      or hydrophobic character) or a stability enhancing amino acid
      (e.g., non- native, D, or alpha methyl amino acid point mutations)
<220> FEATURE:
<223> OTHER INFORMATION: See specification as filed for detailed
      description of substitutions and preferred embodiments

<400> SEQUENCE: 178

Xaa Asp Ile Ile Arg Asn Ile Ala Arg His Leu Ala Xaa Val Gly Asp
1               5                   10                  15

Xaa Xaa Asp Arg Ser Ile Arg Xaa
            20

<210> SEQ ID NO 179
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Non-natural electrophile containing amino acid
<220> FEATURE:
<221> NAME/KEY: MISC_FEATURE
<222> LOCATION: (2)..(6)
<223> OTHER INFORMATION: May or may not be present
<220> FEATURE:
<221> NAME/KEY: MISC_FEATURE
<222> LOCATION: (2)..(13)
<223> OTHER INFORMATION: This region may encompass "EQWAREIGAQLR" or
      "QWAREIGAQLR" "REIGAQLR" or "EIGAQLR" wherein some positions may
      be absent
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (15)..(15)
<223> OTHER INFORMATION: Met or norleucine
<220> FEATURE:
<221> NAME/KEY: MOD_RES
<222> LOCATION: (18)..(18)
<223> OTHER INFORMATION: Any amino acid
<220> FEATURE:
<221> NAME/KEY: MISC_FEATURE
<222> LOCATION: (19)..(24)
<223> OTHER INFORMATION: This region may encompass "LNAQYE" or "LNAQY"
      wherein some positions may be absent
<220> FEATURE:
<221> NAME/KEY: MISC_FEATURE
<222> LOCATION: (24)..(24)
<223> OTHER INFORMATION: May or may not be present
<220> FEATURE:
<221> NAME/KEY: MOD_RES
<222> LOCATION: (25)..(25)
<223> OTHER INFORMATION: Any cell permeability enhancing amino acid
      (e.g., amino acids that change or shift the distribution of charge
      or hydrophobic character) or a stability enhancing amino acid
      (e.g., non- native, D, or alpha methyl amino acid point mutations)
<220> FEATURE:
<223> OTHER INFORMATION: See specification as filed for detailed
      description of substitutions and preferred embodiments

<400> SEQUENCE: 179

Xaa Glu Gln Trp Ala Arg Glu Ile Gly Ala Gln Leu Arg Xaa Xaa Ala
1               5                   10                  15

Asp Xaa Leu Asn Ala Gln Tyr Glu Xaa
            20                  25
```

```
<210> SEQ ID NO 180
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: beta-Ala
<220> FEATURE:
<221> NAME/KEY: MOD_RES
<222> LOCATION: (14)..(14)
<223> OTHER INFORMATION: Any non-natural amino acid
<220> FEATURE:
<221> NAME/KEY: MOD_RES
<222> LOCATION: (18)..(18)
<223> OTHER INFORMATION: Any non-natural amino acid

<400> SEQUENCE: 180

Ala Ala Glu Leu Glu Val Glu Cys Ala Thr Gln Leu Arg Xaa Phe Gly
1               5                   10                  15

Asp Xaa Leu Asn Phe Arg Gln Lys Leu Leu
            20                  25

<210> SEQ ID NO 181
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: beta-Ala
<220> FEATURE:
<221> NAME/KEY: MOD_RES
<222> LOCATION: (14)..(14)
<223> OTHER INFORMATION: Any non-natural amino acid
<220> FEATURE:
<221> NAME/KEY: MOD_RES
<222> LOCATION: (18)..(18)
<223> OTHER INFORMATION: Any non-natural amino acid

<400> SEQUENCE: 181

Ala Ala Glu Leu Glu Val Glu Cys Ala Thr Gln Leu Arg Xaa Phe Gly
1               5                   10                  15

Asp Xaa Leu Asn Phe Arg Gln Lys Leu Leu
            20                  25

<210> SEQ ID NO 182
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: beta-Ala
<220> FEATURE:
<221> NAME/KEY: MOD_RES
<222> LOCATION: (14)..(14)
<223> OTHER INFORMATION: Any non-natural amino acid
<220> FEATURE:
<221> NAME/KEY: MOD_RES
<222> LOCATION: (18)..(18)
<223> OTHER INFORMATION: Any non-natural amino acid
```

-continued

```
<400> SEQUENCE: 182

Ala Ala Glu Leu Glu Val Glu Ser Ala Thr Gln Leu Arg Xaa Phe Gly
1               5                   10                  15

Asp Xaa Leu Asn Phe Arg Gln Lys Leu Leu
            20                  25

<210> SEQ ID NO 183
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: beta-Ala
<220> FEATURE:
<221> NAME/KEY: MOD_RES
<222> LOCATION: (14)..(14)
<223> OTHER INFORMATION: Any non-natural amino acid
<220> FEATURE:
<221> NAME/KEY: MOD_RES
<222> LOCATION: (18)..(18)
<223> OTHER INFORMATION: Any non-natural amino acid

<400> SEQUENCE: 183

Ala Ala Glu Leu Glu Val Glu Ser Ala Thr Gln Leu Arg Xaa Phe Gly
1               5                   10                  15

Asp Xaa Leu Asn Phe Arg Gln Lys Leu Leu
            20                  25

<210> SEQ ID NO 184
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: MOD_RES
<222> LOCATION: (14)..(14)
<223> OTHER INFORMATION: Any non-natural amino acid

<400> SEQUENCE: 184

Glu Val Glu Ser Ala Thr Gln Leu Arg Xaa Phe Gly Asp Xaa Leu Asn
1               5                   10                  15

Phe Arg Gln Lys Leu Leu Lys
            20

<210> SEQ ID NO 185
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: MOD_RES
<222> LOCATION: (14)..(14)
<223> OTHER INFORMATION: Any non-natural amino acid
```

```
<400> SEQUENCE: 185

Glu Val Glu Ser Ala Thr Gln Leu Arg Xaa Phe Gly Asp Xaa Leu Asn
1               5                   10                  15

Phe Arg Gln Lys Leu Leu Lys
            20

<210> SEQ ID NO 186
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: MOD_RES
<222> LOCATION: (14)..(14)
<223> OTHER INFORMATION: Any non-natural amino acid

<400> SEQUENCE: 186

Glu Val Glu Ser Ala Thr Gln Leu Arg Xaa Phe Gly Asp Xaa Leu Asn
1               5                   10                  15

Phe Arg Gln Lys Leu Leu
            20

<210> SEQ ID NO 187
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: MOD_RES
<222> LOCATION: (14)..(14)
<223> OTHER INFORMATION: Any non-natural amino acid

<400> SEQUENCE: 187

Glu Val Glu Ser Ala Thr Gln Leu Arg Xaa Phe Gly Asp Xaa Leu Asn
1               5                   10                  15

Phe Arg Gln Lys Leu Leu Lys
            20

<210> SEQ ID NO 188
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: MOD_RES
<222> LOCATION: (14)..(14)
<223> OTHER INFORMATION: Any non-natural amino acid

<400> SEQUENCE: 188

Glu Val Glu Ser Ala Thr Gln Leu Arg Xaa Phe Gly Asp Xaa Leu Asn
1               5                   10                  15
```

Phe Arg Gln Lys Leu Leu Lys
            20

<210> SEQ ID NO 189
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: MOD_RES
<222> LOCATION: (14)..(14)
<223> OTHER INFORMATION: Any non-natural amino acid

<400> SEQUENCE: 189

Glu Val Glu Ser Ala Thr Gln Leu Arg Xaa Phe Gly Asp Xaa Leu Asn
1               5                   10                  15

Phe Arg Gln Lys Leu Leu Lys
            20

<210> SEQ ID NO 190
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: MOD_RES
<222> LOCATION: (14)..(14)
<223> OTHER INFORMATION: Any non-natural amino acid

<400> SEQUENCE: 190

Glu Val Glu Ser Ala Thr Gln Leu Arg Xaa Phe Gly Asp Xaa Leu Asn
1               5                   10                  15

Phe Arg Gln Lys Leu Leu Lys
            20

<210> SEQ ID NO 191
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: MOD_RES
<222> LOCATION: (14)..(14)
<223> OTHER INFORMATION: Any non-natural amino acid

<400> SEQUENCE: 191

Glu Val Glu Ser Ala Thr Gln Leu Arg Xaa Phe Gly Asp Xaa Leu Asn
1               5                   10                  15

Phe Arg Gln Lys Leu Leu Lys
            20

<210> SEQ ID NO 192
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: MOD_RES
<222> LOCATION: (14)..(14)
<223> OTHER INFORMATION: Any non-natural amino acid

<400> SEQUENCE: 192

Glu Val Glu Ser Ala Thr Gln Leu Arg Xaa Phe Gly Asp Xaa Leu Asn
1               5                   10                  15

Phe Arg Gln Lys Leu Leu Lys
            20

<210> SEQ ID NO 193
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: MOD_RES
<222> LOCATION: (14)..(14)
<223> OTHER INFORMATION: Any non-natural amino acid

<400> SEQUENCE: 193

Glu Val Glu Ser Ala Thr Gln Leu Arg Xaa Phe Gly Asp Xaa Leu Asn
1               5                   10                  15

Phe Arg Gln Lys Leu Leu
            20

<210> SEQ ID NO 194
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: MOD_RES
<222> LOCATION: (14)..(14)
<223> OTHER INFORMATION: Any non-natural amino acid

<400> SEQUENCE: 194

Glu Val Glu Ser Ala Thr Gln Leu Arg Xaa Phe Gly Asp Xaa Leu Asn
1               5                   10                  15

Phe Arg Gln Lys Leu Leu Lys
            20

<210> SEQ ID NO 195
<211> LENGTH: 19
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any non-natural amino acid
<220> FEATURE:
<221> NAME/KEY: MOD_RES
<222> LOCATION: (11)..(11)
<223> OTHER INFORMATION: Any non-natural amino acid

<400> SEQUENCE: 195

Ile Ala Gln Glu Leu Arg Xaa Ile Gly Asp Xaa Phe Asn Ala Tyr Tyr
1               5                   10                  15

Ala Arg Lys

<210> SEQ ID NO 196
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any non-natural amino acid
<220> FEATURE:
<221> NAME/KEY: MOD_RES
<222> LOCATION: (11)..(11)
<223> OTHER INFORMATION: Any non-natural amino acid

<400> SEQUENCE: 196

Ile Ala Gln Glu Leu Arg Xaa Ile Gly Asp Xaa Phe Asn Ala Tyr Tyr
1               5                   10                  15

Ala Arg Lys

<210> SEQ ID NO 197
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any non-natural amino acid
<220> FEATURE:
<221> NAME/KEY: MOD_RES
<222> LOCATION: (11)..(11)
<223> OTHER INFORMATION: Any non-natural amino acid

<400> SEQUENCE: 197

Ile Ala Gln Glu Leu Arg Xaa Ile Gly Asp Xaa Phe Asn Ala Tyr Tyr
1               5                   10                  15

Ala Arg Arg

<210> SEQ ID NO 198
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
```

<223> OTHER INFORMATION: Any non-natural amino acid
<220> FEATURE:
<221> NAME/KEY: MOD_RES
<222> LOCATION: (11)..(11)
<223> OTHER INFORMATION: Any non-natural amino acid

<400> SEQUENCE: 198

Ile Ala Gln Glu Leu Arg Xaa Ile Gly Asp Xaa Phe Asn Ala Tyr Tyr
1               5                   10                  15

Ala Arg Arg Lys
            20

<210> SEQ ID NO 199
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any non-natural amino acid
<220> FEATURE:
<221> NAME/KEY: MOD_RES
<222> LOCATION: (11)..(11)
<223> OTHER INFORMATION: Any non-natural amino acid

<400> SEQUENCE: 199

Ile Ala Gln Glu Leu Arg Xaa Ile Gly Asp Xaa Phe Asn Ala Tyr Tyr
1               5                   10                  15

Ala Arg Lys

<210> SEQ ID NO 200
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any non-natural amino acid
<220> FEATURE:
<221> NAME/KEY: MOD_RES
<222> LOCATION: (11)..(11)
<223> OTHER INFORMATION: Any non-natural amino acid

<400> SEQUENCE: 200

Ile Ala Gln Glu Leu Arg Xaa Ile Gly Asp Xaa Phe Asn Ala Tyr Tyr
1               5                   10                  15

Ala Arg Lys

<210> SEQ ID NO 201
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any non-natural amino acid
<220> FEATURE:
<221> NAME/KEY: MOD_RES
<222> LOCATION: (11)..(11)
<223> OTHER INFORMATION: Any non-natural amino acid

```
<400> SEQUENCE: 201

Ile Ala Gln Glu Leu Arg Xaa Ile Gly Asp Xaa Phe Asn Ala Tyr Tyr
1               5                   10                  15

Ala Arg Lys

<210> SEQ ID NO 202
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any non-natural amino acid
<220> FEATURE:
<221> NAME/KEY: MOD_RES
<222> LOCATION: (11)..(11)
<223> OTHER INFORMATION: Any non-natural amino acid

<400> SEQUENCE: 202

Ile Ala Gln Glu Leu Arg Xaa Ile Gly Asp Xaa Phe Asn Ala Tyr Tyr
1               5                   10                  15

Ala Arg Lys

<210> SEQ ID NO 203
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any non-natural amino acid
<220> FEATURE:
<221> NAME/KEY: MOD_RES
<222> LOCATION: (11)..(11)
<223> OTHER INFORMATION: Any non-natural amino acid

<400> SEQUENCE: 203

Ile Ala Gln Glu Leu Arg Xaa Ile Gly Asp Xaa Phe Ala Asn Tyr Tyr
1               5                   10                  15

Ala Arg Lys

<210> SEQ ID NO 204
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any non-natural amino acid
<220> FEATURE:
<221> NAME/KEY: MOD_RES
<222> LOCATION: (11)..(11)
<223> OTHER INFORMATION: Any non-natural amino acid

<400> SEQUENCE: 204

Ile Ala Gln Glu Leu Arg Xaa Ile Gly Asp Xaa Phe Asn Ala Tyr Tyr
1               5                   10                  15

Ala Arg Arg
```

```
<210> SEQ ID NO 205
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any non-natural amino acid
<220> FEATURE:
<221> NAME/KEY: MOD_RES
<222> LOCATION: (11)..(11)
<223> OTHER INFORMATION: Any non-natural amino acid

<400> SEQUENCE: 205

Ile Ala Gln Glu Leu Arg Xaa Ile Gly Asp Xaa Phe Asn Ala Tyr Tyr
1               5                   10                  15

Ala Arg Arg Lys
            20

<210> SEQ ID NO 206
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: beta-Ala
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: MOD_RES
<222> LOCATION: (14)..(14)
<223> OTHER INFORMATION: Any non-natural amino acid

<400> SEQUENCE: 206

Ala Ile Trp Ile Ala Gln Glu Leu Arg Xaa Ile Gly Asp Xaa Phe Asn
1               5                   10                  15

Ala Tyr Tyr Ala Arg Arg
            20

<210> SEQ ID NO 207
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any non-natural amino acid
<220> FEATURE:
<221> NAME/KEY: MOD_RES
<222> LOCATION: (11)..(11)
<223> OTHER INFORMATION: Any non-natural amino acid

<400> SEQUENCE: 207

Ile Ala Gln Glu Leu Arg Xaa Ile Gly Asp Xaa Phe Asn Ala Tyr Tyr
1               5                   10                  15

Ala Arg Arg
```

```
<210> SEQ ID NO 208
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any non-natural amino acid
<220> FEATURE:
<221> NAME/KEY: MOD_RES
<222> LOCATION: (13)..(13)
<223> OTHER INFORMATION: Any non-natural amino acid

<400> SEQUENCE: 208

Ile Trp Ile Ala Gln Glu Leu Arg Xaa Ile Gly Asp Xaa Phe Asn Ala
1               5                   10                  15

Tyr Tyr Ala Arg Arg
            20

<210> SEQ ID NO 209
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ala Glu Leu Glu Val Glu Cys Ala Thr Gln Leu Arg Arg Phe Gly Asp
1               5                   10                  15

Lys Leu Asn Phe Arg Gln Lys Leu Leu
            20                  25

<210> SEQ ID NO 210
<211> LENGTH: 9
<212> TYPE: PRT
<213> ORGANISM: Artificial Sequence
<220> FEATURE:
<223> OTHER INFORMATION: Description of Artificial Sequence: Synthetic
      9xHis tag

<400> SEQUENCE: 210

His His His His His His His His His
1               5
```

PEPTIDES BINDING TO BFL-1

CROSS-REFERENCE TO RELATED APPLICATIONS

This application is a U.S. National Stage application, and claims priority of International Application No. PCT/US2016/049095, filed Aug. 26, 2016, which claims priority to U.S. Provisional Application No. 62/211,680, filed Aug. 28, 2015. The contents of all of the prior applications are incorporated by reference herein in their entirety.

STATEMENT REGARDING FEDERALLY SPONSORED RESEARCH

This invention was made with government support under grant number 1R35CA197583 awarded by the National Institutes of Health. The government has certain rights in the invention.

TECHNICAL FIELD

This disclosure relates to structurally stabilized peptides that can bind to Bfl-1 and methods for using such peptides in the treatment of cancer.

BACKGROUND

The BCL-2 protein family, which includes both pro-apoptotic and anti-apoptotic members, forms a complex network of checks and balances that dictate cell fate. The family is structurally defined by the presence of up to four conserved "BCL-2 homology" (BH) domains, all of which include alpha-helical portions. Anti-apoptotic proteins such as Bfl-1 and MCL-1 display sequence conservation in all BH domains, whereas pro-apoptotic proteins are divided into "multi-BH domain" members (e.g., BAX and BAK) and "BH3-only" members (e.g., BIM and NOXA) that display sequence similarity only in the alpha-helical BH3 domain. The BH3-only subgroup is diverse and transmits pro-death signals from disparate stimuli to apoptotic machinery located at the mitochondria. The BH3-only protein's death signal will either be neutralized by anti-apoptotic proteins or delivered, directly or indirectly, to the mitochondrial executioners BAX and BAK. When activated, BAX/BAK induce outer mitochondrial membrane permeabilization, enabling released mitochondrial factors to induce caspases, which irreversibly execute the death program.

Cancer cells overexpress anti-apoptotic proteins to suppress pro-apoptotic proteins, thereby mounting an apoptotic blockade that ensures their survival. Drugs that disrupt BCL-2 family protein interaction can induce apoptosis in cancer cells.

BFL-1 has been implicated in suppressing the mitochondrial apoptotic pathway in a wide variety of liquid and solid tumors. For example, when overexpressed or mutated to resist ubiquitin-mediated degradation, Bfl-1 induces chemoresistance in discrete lymphomas, including the BCR-dependent/elevated NFκB subclass of germinal center lymphomas and diffuse large B-cell lymphomas. Bfl-1 was also recently identified as a pathologic survival factor in approximately 30% of human melanomas, including those with clinically relevant BRAF V600E resistance mutations. Thus, compounds that interfere with BFL-1 activity could be useful in treating melanoma and a variety of other cancers.

SUMMARY

The present disclosure provides structurally stabilized peptides related to (e.g., sharing sequence homology with) NOXA, BAX, BIM, BID, PUMA, BAK or BOK, and methods for using such stabilized peptides as therapeutic and/or prophylactic agents. The stabilized peptides can bind and, in certain instances, can covalently link to BFL-1 thereby modulating (e.g., interfering with) BFL-1 activity.

In some aspects, the present disclosure provides internally cross-linked polypeptides comprising the amino acid sequence of all or a portion (e.g., 6, 7, 8, 9, 10, 11, 12, 13, 14, 15, 16, 17, 18, 19, 20, 21, 22, 23, 24, 25, 26, 27, 28, 29, 30 amino acids) of the BH3 domain of NOXA, BAX, BIM, BID, PUMA, BAK, or BOK, wherein:

the side chains of two amino acids separated by two, three or six amino acids are replaced by an internal staple; the side chains of three amino acids are replaced by internal stitch; the side chains of four amino acids are replaced by two internal staples, the side chains of five amino acids are replaced by the combination of a stitch and a staple, or the sides chains of six amino acids are replaced by two stiches or three staples; and, optionally, the side chain, or N-terminus of one amino acid is replaced by an electrophilic group that can covalently react with the side chain of a cysteine in Bfl-1. In certain instances, the side-chain of an amino acid of the cross-linked polypeptide, or the N-terminus or C-terminus is replaced with an electrophilic warhead that is not an amino acid. The electrophile can thus, not only be installed in the context of a non-natural amino acid, but also as a chemical cap to the N or C terminus of the cross-linked polypeptide.

In some embodiments, internally cross-linked peptides can be made by modifying (e.g., by amino acid substitution) a polypeptide selected from the group consisting of SEQ ID NOs:1-7 or 37-40. In some embodiments, the internal staple replaces the side chains of 2 amino acids, i.e., each staple is between two amino acids separated by, for example, 3, 4, or 6 amino acids. In some embodiments, the internal stitch replaces the side chains of 3 amino acids, i.e., the stitch is a pair of crosslinks between three amino acids separated by, for example, 3 and 6 amino acids. In some embodiments, the internal staples and/or the internal stitch comprises at least two internal staples (replacing the side chains of 4 amino acids, i.e., each staple is between two amino acids separated by, for example, 3 amino acids). In some embodiments, the internal staples and/or the internal stitch comprises a combination of at least one internal staple and an internal stitch. In some embodiments, the internal stitch replaces the side chain of a first amino acid and a second and a third amino acid thereby cross-linking the first amino acid (which lies between the second and third amino acids) to the second and third amino acid via an internal cross-link, wherein the first and second amino acid are separated by two, three, or six amino acids, the first and the third amino acids are separated by two, three, or six amino acids, and the second and third amino acids are distinct amino acids. In some embodiments, the side chains of the four amino acids of the internally cross-linked polypeptides of the disclosure are replaced by two distinct internal staples. In some embodiments, a first of the two distinct internal staples cross-links a first pair of amino acids separated by two, three, or six amino acids, and a second of the at least two distinct internal staples cross-links a second pair of amino acids separated by two, three, or six amino acids. In some embodiments, internally cross-linked polypeptides of the disclosure are prepared from polypeptides selected from the group consisting of SEQ ID NOs: 1-7 or 37-40; the group consisting of SEQ ID NOs: 1-7 or 37-40 and having an amino terminal or carboxy terminal modification; and the group consisting of SEQ ID NOs: 1-7 or 37-40 and having 1, 2, 3, 4, or 5 amino acid substitutions (e.g., 1, 2, 3, 4, or 5 amino acids are conservatively or non-conservatively substituted).

In some aspects, the disclosure features a polypeptide that binds Bfl-1, the polypeptide comprising an amino acid sequence that is at least 40%, at least 50%, at least 60%, at least 65% at least 70%, at least 75%, at least 80%, at least 85%, at least 90%, at least 95%, or at least 97% identical to the interacting face of the helix (i.e., the helix interacting with Bfl-1) of an amino acid sequence set forth below:

(i) AELEVECATQLRRFGDKLNFRQKLLN (SEQ ID NO:122):

(ii) EIWIAQELRRIGDEFNAYYARR (SEQ ID NO:123);

(iii) DIIRNIARHLAQVGDSMDRSI (SEQ ID NO:124):

(iv) SSTMGQVGRQLAIIGDDINRRY (SEQ ID NO:125):

(v) QDASTKKLSESLKRIGDELDSNMEL (SEQ ID NO:126); or (vi) RLAEVCAVLLRLGDELEMIR (SEQ ID NO:127), wherein the polypeptide selectively binds Bfl-1 over MCL-1: wherein at least two amino acids in each amino acid sequence are substituted by non-natural amino acids with olefinic side chains, wherein at least one cysteine, if present, in the polypeptide could be replaced by serine, and wherein at least one methionine, if present, in the polypeptide could be replaced by norleucine; and wherein the polypeptide comprises a non-natural amino acid bearing an electrophilic group. As indicated above, the percent identities referenced above with respect to the peptide sequence refer to the Bfl-1-interacting face of the helix of each peptide. Much greater variability is permitted in the region of the peptide that does not interact with Bfl-1. In fact, just about every one of those amino acids (e.g., 10, 9, 8, 7, 6, 5, 4, 3, 2, or 1 amino acid of the non-interacting face of the helix) can be substituted (e.g., conservative or non-conservative amino acid substitutions or alanine). In certain embodiments, the interacting face of the helix of these peptides have 1 to 10, 1 to 9, 1 to 8, 1 to 7, 1 to 6, 1 to 5, 1 to 4, 1 to 3, 1 to 2, or 1 amino acid substitution(s). In some instances, the substitution is a conservative amino acid substitution.

In some aspects, the disclosure features a polypeptide that binds to Bfl-1, the polypeptide comprising an amino acid sequence that is at least 40%, at least 50%, at least 60%, at least 65% at least 70%, at least 75%, at least 80%, at least 85%, at least 90%, at least 95%, or at least 97% identical to the interacting face of the helix (i.e., the helix interacting with Bfl-1) of an amino acid sequence set forth below:

(i) ATQLRRFGDKLNFRQ (SEQ ID NO:131);

(ii) IAQELRRIGDEFNAYYARR (SEQ ID NO:132):

(iii) ARHLAQVGDSMDR (SEQ ID NO:133):

(iv) GRQLAIIGDDINR (SEQ ID NO: 134);

(v) LSESLKRIGDELDS (SEQ ID NO:135); or (vi) CAVLLRLGDELEM (SEQ ID NO:136), wherein the polypeptide selectively binds Bfl-1 over MCL-1; wherein at least two amino acids in each amino acid sequence are substituted by non-natural amino acids with olefinic side chains, wherein at least one cysteine, if present, in the polypeptide could be replaced by serine, and wherein at least one methionine, if present, in the polypeptide could be replaced by norleucine; and wherein the polypeptide comprises a non-natural amino acid bearing an electrophilic group. As indicated above, the percent identities referenced above with respect to the peptide sequence refer to the Bfl-1-interacting face of the helix of each peptide. Much greater variability is permitted in the region of the peptide that does not interact with Bfl-1. In fact, just about every one of those amino acids (e.g., 10, 9, 8, 7, 6, 5, 4, 3, 2, or 1 amino acid of the non-interacting face of the helix) can be substituted (e.g., conservative or non-conservative amino acid substitutions or alanine). In certain embodiments, the interacting face of the helix of these peptides have 1 to 10, 1 to 9, 1 to 8, 1 to 7, 1 to 6, 1 to 5, 1 to 4, 1 to 3, 1 to 2, or 1 amino acid substitution(s). In some instances, the substitution is a conservative amino acid substitution.

In some aspects, the disclosure features a polypeptide that binds Bfl-1, the polypeptide comprising an amino acid sequence that is at least 40%, 50%, 55%, 60%, 65%, 70%, 75%, 80%, 85%, 90%, 95%, or 97% identical to the Bfl-1 interacting alpha-helical face of an amino acid sequence set forth in any one of SEQ ID NOs.: 22-36, 41-119, or in FIG. 18. In certain cases, the disclosure provides a polypeptide that binds Bfl-1 and comprises an amino acid sequence set forth in any one of SEQ ID NOs.: 22-36, 41-119, or in FIG. 18. These polypeptides include "warheads" that are essential for covalent modification of Bfl-1. The warheads may be at the N-terminus, C-terminus, or within the polypeptide sequence. In some cases, the warhead is a non-natural electrophile bearing amino acid. In certain embodiments, the warhead is selected from the group consisting of: 3S-1-pyrrolidine-3-carboxylic acid terminating in acrylamide; D-homoproline terminating in acrylamide; L-homoproline terminating in acrylamide: isonipecotic acid terminating in acrylamide: D-nipecotic acid terminating in acrylamide; L-nipecotic acid terminating in acrylamide; D-proline terminating in acrylamide; L-proline terminating in acrylamide; trans-4-dimethylaminocrotonic acid; and acrylic acid. In other embodiments, the warhead is a non-natural amino acid bearing an electrophilic group that is selected from the group consisting of: (S)-1-acryloylpyrrolidine-3-carboxamide: 1-acnylopiperidine-4-carboxamide, (R)-1 acryloylpiperidine-3-carboxamide; (S)-1-acryloylpiperidine-3-carboxamide; (S)-1-acryloylpyyrolidine-2-carboxamide; (R)-1-acryloylpyrrolidine-2-carboxamide; (E)-4-(dimethylamino)but-2-enamide; and acrylamide. In other embodiments, the warhead is not an amino acid. For example, the electrophilic moiety and peptide are linked via a nitrogen containing heterocycle, either saturated (aziridine, diaziridine, azetidine, pyrrolidine, imidazolidine, pyrazolidine, oxazolidine, isoxazolidine, thiazolidine, isothiazolidine, piperidine, piperazine, morpholine, thiomorpholine, azepane) or unsaturated (azirine, diazirine, azete, pyrrole, imidazole, pyrazole, oxazole, isoxazole, thiazole, isothiazole, pyridine, diazines, oxazine, thiazine, azepine). The peptide and electrophile can also be linked by a substituted amino-functionalized ring (e.g. N-arylacrylamide) such as phenyl (aniline) or by more complex bicyclic or polycyclic rings, for instance, naphthalene, anthracene, phenanthrene, indole, isoindole, indolizine, quinolone, isoquinoline, quinoxaline, phthalzine, quinazoline, purine, carbazole, indazole, benzimidazole, azaindole. The electrophilic warhead in some embodiments is an acrylamide, or more generally defined as an α,β-unsaturated carbonyl, such as α-cyanoacrylamide, propiolamide, trans 4-dimethylamino-2-butenamide, or trans 4-piperidinyl-2-butenamide, or any other substituted acrylamide, or N-functionalized vinylsulfonyl, alpha-fluoro acetyl, alpha-chloro acetyl, alpha-bromo acetyl, and alpha-iodo acetyl or other electrophilic moiety. The electrophile can not only be installed in the context of a non-natural amino acid, but also as a chemical cap to the N or C terminus of the cross-linked (e.g., stapled, stitched) polypeptide.

In another aspect, the disclosure features a polypeptide comprising an amino acid sequence that is at least 40%, 50%, 55%, 60%, 65%, 70%, 75%, 80%, 85%, 90%, 95%, or 97% identical to the Bfl-1 interacting alpha-helical face of an amino acid sequence set forth in any one of: JEVESATQLRXFGDXLNFRQKLL (SEQ ID NO:24); JIAQELRXIGDXFNAYYARR (SEQ ID NO:30); or JAT8LRRFGDXLNFRQ (SEQ ID NO:62), wherein J is a non-natural electrophile containing amino acid (but note that this position (i.e., "J") can also be an electrophilic warhead presented in the context of a moiety that is not an amino acid. The electrophile can serve as a chemical cap.), X is a non-natural amino acid, and 8 is R-octenyl alanine. The two X's in a polypeptide sequence can be the same or be different non-natural amino acids with olefinic side chains depending on the spacing. In some instances, each X is S-pentenyl alanine.

In specific aspects, the disclosure features a polypeptide comprising the amino acid sequence: JEVESATQLRXFGDXLNFRQKLL (SEQ ID NO:24): JIAQELRXIGDXFNAYYARR (SEQ ID NO:30); or JAT8LRRFGDXLNFRQ (SEQ ID NO:62), wherein J is a non-natural electrophile containing amino acid (but note that this position (i.e., "J") can also be an electrophilic warhead presented in the context of a moiety that is not an amino acid. The electrophile can serve as a chemical cap.), X is a non-natural amino acid, and 8 is R-octenyl alanine. The two X's in a polypeptide sequence can be the same or be different non-natural amino acids with olefinic side chains depending on the spacing. In some instances, each X is S-pentenyl alanine. In other embodiments, the electrophilic warhead is not an amino acid. For example, the electrophilic moiety and peptide are linked via a nitrogen containing heterocycle, either saturated (aziridine, diaziridine, azetidine, pyrrolidine, imidazolidine, pyrazolidine, oxazolidine, isoxazolidine, thiazolidine, isothiazolidine, piperidine, piperazine, morpholine, thiomorpholine, azepane) or unsaturated (azrine, diazrine, azete, pyrrole, imidazole, pyrazole, oxazole, isoxazole, thiazole, isothiazole, pyridine, diazines, oxazine, thiazine, azepine). The peptide and electrophile can also be linked by a substituted amino-functionalized ring (e.g. N-arylacrylamide) such as phenyl (aniline) or by more complex bicyclic or polycyclic rings, for instance, naphthalene, anthracene, phenanthrene, indole, isoindole, indolizine, quinolone, isoquinoline, quinoxaline, phthalzine, quinazoline, purine, carbazole, indazole, benzimidazole, azaindole. The electrophilic warhead in some embodiments is an acrylamide, or more generally defined as an α,β-unsaturated carbonyl, such as α-cyanoacrylamide, propiolamide, trans 4-dimethylamino-2-butenamide, or trans 4-piperidinyl-2-butenamide, or any other substituted acrylamide. The electrophile can not only be installed in the context of a non-natural amino acid, but also as a chemical cap to the N or C terminus of the cross-linked (e.g., stapled, stitched) polypeptide.

In some embodiments, the linker fulfills several critical roles. The linker servers to position the electrophile with Angstrom or sub-Angstrom precision in a location, orientation, and geometry that enables a covalent reaction to occur between the SH of the target cysteine and the alpha-beta unsaturated amide (or similar electrophilic moiety). Linkers that are rings are able to adopt a configuration that may be compatible with reaction. An aminobenzene or similar amino-derivatized aromatic ring or series of rings is also capable of precise placement. Finally, because the reactivity of the electrophile needs to be precisely tuned so as to enable the desired reaction yet not be promiscuously reactive, substituents on the linker can exert effects on the reactivity and therefore require careful selection.

In certain embodiments, the polypeptides described herein have staples, stitches, or combinations of staples and stitches.

In certain embodiments, the polypeptides described herein are at least 10 amino acids in length but less than 100, 75, 50, or 30 amino acids in length. In certain embodiments, the polypeptides described herein are between 8 and 30 amino acids in length.

In some aspects, the disclosure provides pharmaceutical compositions that include one or more internally cross-linked polypeptides of the disclosure. In some embodiments, such pharmaceutical compositions can also include one or more medicaments for the treatment of cancer In some aspects, the disclosure provides methods for treating cancer in a subject. These methods can include selecting a subject suffering from cancer and administering to the subject an effective amount of the stabilized peptides of claims described herein. These methods can be practiced in concert with administering the subject with chemotherapy, radiotherapy, immunotherapy, or other cancer-treatment modalities, or a combination thereof. These treatments can be administered simultaneously or sequentially with the treatment with the stabilized warhead-containing peptides.

The term "halo" refers to any radical of fluorine, chlorine, bromine or iodine. The term "alkyl" refers to a hydrocarbon chain that may be a straight chain or branched chain, containing the indicated number of carbon atoms. For example, $C_1$-$C_{10}$ indicates that the group may have from 1 to 10 (inclusive) carbon atoms in it. In the absence of any numerical designation, "alkyl" is a chain (straight or branched) having 1 to 20 (inclusive) carbon atoms in it. The term "alkylene" refers to a divalent alkyl (i.e., —R—).

The term "alkenyl" refers to a hydrocarbon chain that may be a straight chain or branched chain having one or more carbon-carbon double bonds in either Z or E geometric configurations. The alkenyl moiety contains the indicated number of carbon atoms. For example, $C_2$-$C_{10}$ indicates that the group may have from 2 to 10 (inclusive) carbon atoms in it. The term "lower alkenyl" refers to a $C_2$-$C_8$ alkenyl chain. In the absence of any numerical designation, "alkenyl" is a chain (straight or branched) having 2 to 20 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_2$-$C_{10}$ indicates that the group may have from 2 to 10 (inclusive) carbon atoms in it. The term "lower alkynyl" refers to a $C_2$-$C_8$ alkynyl chain. In the absence of any numerical designation, "alkynyl" is a chain (straight or branched) having 2 to 20 (inclusive) carbon atoms in it.

The term "aryl" refers to a 6-carbon monocyclic or 10-carbon bicyclic aromatic ring system wherein 0, 1, 2, 3, 4, or 5 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally may be optionally substituted. Preferred cycloalkyl groups include, without limitation, cyclopropyl, cyclobutyl, cyclopentyl, cyclopentenyl, cyclohexyl, cyclohexenyl, cyclohexadienyl, cycloheptyl, cycloheptadienyl, cycloheptatrienyl, cyclooctyl, cyclooctenyl, cyclooctadienyl, cyclooctatrienyl, and cyclooctynyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyrrolyl, pyridyl, furyl or furanyl, imidazolyl, 1,2,3-triazolyl, 1,2,4-triazolyl, benzimidazolyl, pyridazyl, pyrimidyl, thiophenyl, quinolinyl, indolyl, thiazolyl, oxazolyl, isoxazolyl and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, aziridinyl, oxiryl, thiiryl, morpholinyl, tetrahydrofuranyl, and the like.

The term "substituents" refers to a group "substituted" on an alkyl, cycloalkyl, aryl, heterocyclyl, or heteroaryl group at any atom of that group. Suitable substituents include, without limitation, halo, hydroxy, mercapto, oxo, nitro, haloalkyl, alkyl, alkaryl, aryl, aralkyl, alkoxy, thioalkoxy, aryloxy, amino, alkoxycarbonyl, amido, carboxy, alkanesulfonyl, alkylcarbonyl, azido, and cyano groups.

The term "amino acid" refers to a molecule containing both an amino group and a carboxyl group as well as a side chain. Amino acids suitable for inclusion in the peptides disclosed herein include, without limitation, natural alpha-amino acids such as D- and L-isomers of the 20 common naturally occurring alpha-amino acids found in peptides (e.g., Ala (A), Arg (R), Asn (N), Cys (C), Asp (D), Gln (Q), Glu (E), Gly (G), His (H), Ile (I), leu (L), Lys (K), Met (M), Phe (F), Pro (P), Ser (S), Thr (T), Trp (W), Tyr (Y), and Val (V), unnatural alpha-amino acids (including, but not limited to α,α-disubstituted and N-alkylated amino acids), natural beta-amino acids (e.g., beta-alanine), and unnatural beta-amino acids. Amino acids used in the construction of peptides of the present invention can be prepared by organic synthesis, or obtained by other routes, such as, for example, degradation of or isolation from a natural source.

There are many known unnatural amino acids any of which may be included in the peptides of the present invention. Some examples of unnatural amino acids are 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and/para-substituted phenylalanines (e.g., substituted with —C(O)C6H5; —CF3; —CN; -halo; —NO2; CH3), disubstituted phenylalanines, substituted tyrosines (e.g., further substituted with -Q=O)C6H5; —CF3; —CN; -halo; —NO2; CH3), and statine. Additionally, amino acids can be derivatized to include amino acid residues that are hydroxylated, phosphorylated, sulfonated, acylated, and glycosylated, to name a few.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF THE DRAWINGS

FIG. 2: Depicts a number of internally cross-linked NOXA SAHB peptides. X indicates the amino acids whose side chains that can form an internal cross-link (e.g., non-natural amino acids with olefinic side chains). The sequences in the figure have the amino acid sequences set forth in SEQ ID NOs.: 9-21 (from top (SEQ ID NO:9) to bottom (SEQ ID NO:21)).

FIG. 3A: Depicts the results of studies assessing the binding of various NOXA SAHB peptides to MCL-1 and Bfl-1.

FIG. 3B: Depicts NOXA SAHB peptides with substitution at F32. The amino acid sequence shown in the figure has the amino acid sequence set forth in SEQ ID NO:9.

FIG. 6: Depicts various NOXA, BAX, BIM1, BIM2, BAK and BOK SAHB peptides. J indicates the position of the "warhead" for covalent binding to the target protein. The amino acid sequences of the different peptides are, from top to bottom, set forth in SEQ ID NOs.: 22-36, 1, and 37-40. The boldened residues in SEQ ID NOs.: 1, 38, and 39 identify the 25 amino acids that can be replaced with a "warhead."

FIG. 7: Depicts the stapling technology and various staples that can be formed.

FIG. 18: Stapled Peptide Compositions. The 29 amino acid sequences of the peptides in the "Sequence" column are, from top to bottom, set forth in SEQ ID NOs: 9, 9, 13, 13, 184, 184, 186, 186, 184, 184, 184, 184, 184, 186, 186, 195, 195, 197, 197, 195, 195, 195, 195, 195, 197, 197, 208, 197, and 208.

FIG. 20: Crystal structure of human Bfl-1 in complex with NOXA BH3 peptide annotated with protein target cysteine residue number, proximal helix residue number, and distance in Angstroms. Below the crystal structure are exemplary stapled peptide sequences of NOXA BH3. J=non-natural electrophile containing amino acid (but can be an electrophilic warhead that does not comprise an amino acid); 8=R8, X=non-natural amino acid with olefinic side chain (e.g., S5).

FIG. 23: Exemplary BAK BH3 Stapled Peptides with "warhead". J=non-natural electrophile containing amino acid (but can be an electrophilic warhead that does not comprise an amino acid; 8=R8, X=non-natural amino acid with olefinic side chain (e.g., S5).

FIG. 24: Exemplary BAX BH3 Stapled Peptides with "warhead". J=non-natural electrophile containing amino acid (but can be an electrophilic warhead that does not comprise an amino acid); 8=R8, X=non-natural amino acid with olefinic side chain (e.g., S5).

DETAILED DESCRIPTION

Stabilized Peptides

Figure 1:
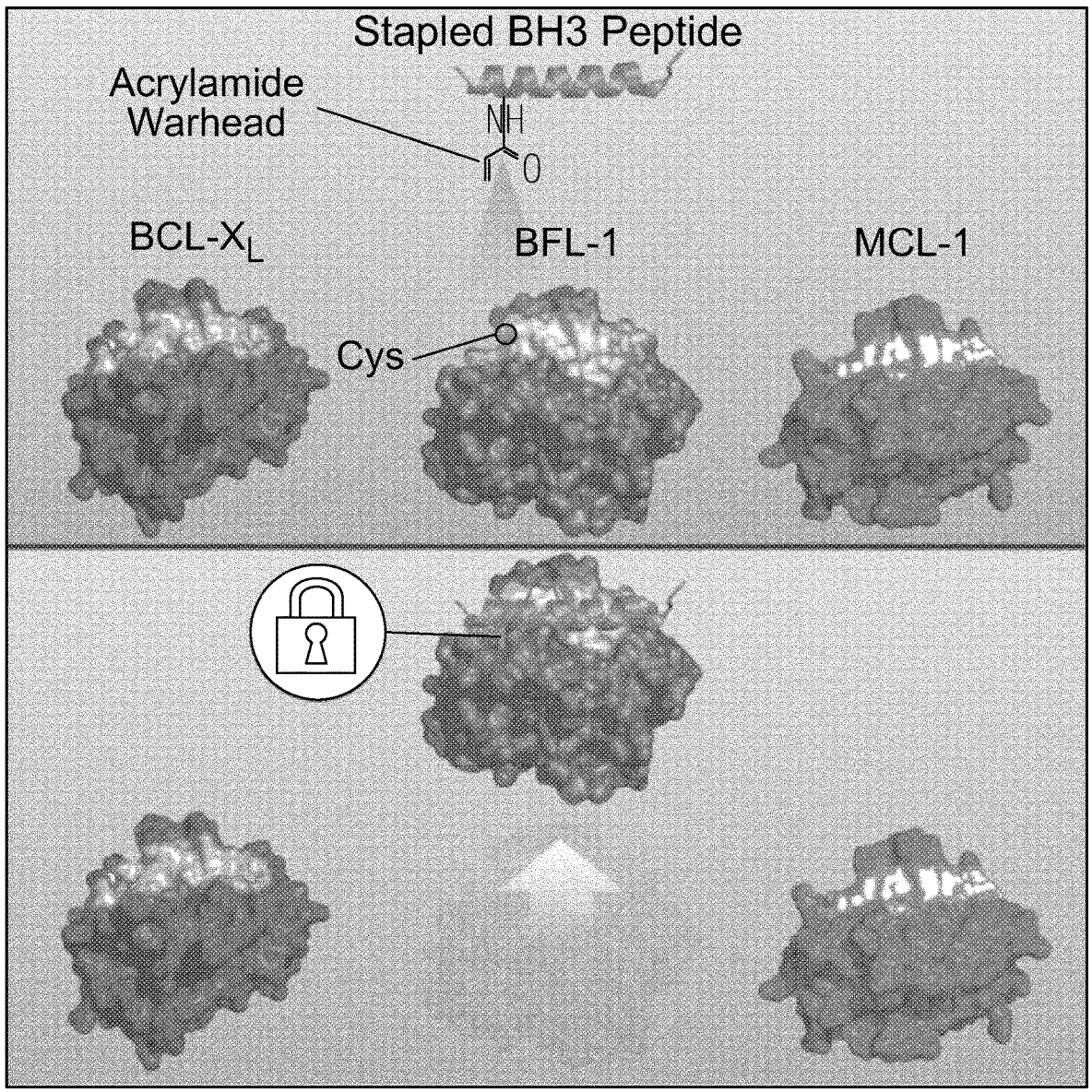
FIG. 1: Depicts the general conceptual strategy of specific targeting of Bfl-1 with acrylamide containing stapled peptides.

The present disclosure provides structurally stabilized peptides related to NOXA, BIM, BAX, BAK, BID, or BOK comprising at least two modified amino acids joined by an internal (intramolecular) cross-link (or staple) and having a reactive group (warhead) that can form a covalent bonding with a Cys residue within a target protein to which the structurally stabilized peptide binds (e.g., Bfl-1). Stabilized peptides as described herein include stapled peptides and stitched peptides as well as peptides containing multiple stitches, multiple staples or a mix or staples and stitches.

In some instances, peptides that bind Bfl-1 can include (e.g., comprise, consist essentially of, or consist of) at least 10 (e.g., 10, 11, 12, 13, 14, 15, 20 or more) or at least 15 (e.g., 15, 16, 17, 18, 19, 20, 21, 22 or more) contiguous amino acids of a sequence selected from:

```
                                    (SEQ ID NO: 1; NOXA)
AELEVESATQLRRFGDKLNFRQKLL (SEQ ID NO: 2; BIM)
DMPREIWIAQELRRIGDEFNAYYARR (SEQ ID NO: 3; BAX)
QDASTKKLSESLKRIGDELDSNMELQR (SEQ ID NO: 4; BAK)
SSTMGQVGRQLAIIGDDINRRYDSEFQTMLQHLQ (SEQ ID NO: 5; BOK)
PGGRLAEVSTVLLRLGDELEQIRPS (SEQ ID NO: 6; BID)
SESQEDIIRNIARHLAQVGDSMDRSIPPG (SEQ ID NO: 7; PUMA)
EEEQWAREIGAQLRRMADDLNAQYERRRQEEQQ (SEQ ID NO: 8; BFl-1)
KKFEPKSGWMTFLEVTGKICEMLSLLKQYC
``` wherein the peptide has a reinforced or stabilized alpha helical secondary structure (e.g., wherein the peptide includes at least one internal crosslink) and a non-natural amino acid bearing an electrophilic group (e.g., non-natural amino acid bearing reactive acrylamide moieties), that can react with the side chain of a cysteine residue.

In some cases the peptides include fewer than 30, fewer than 25 or fewer than 20 amino acids.

In some instances, stabilized peptides that bind to Bfl-1 can have at least 50% (e.g., 40%, 45%, 50%, 55%, 60%, 65%, 70%, 75%, 80%, 85%, 90%, 95%, 98%, 99%, 99.5%, or 100%) identity to one of SEQ ID NOs: 1-7 or 37-40. In certain embodiments, the percent identities referenced above with respect to the peptides refer to the Bfl-1-interacting face of the helix of the peptide. From the crystal structure, Bfl-1 interacting residues are for:

NOXA: Leu-21, Glu-22, Val-23, Glu-24, Cys-25, Ala-26, Gln-28, Leu-29, Arg-30, Phe-32, Gly-33, Asp-34, Leu-36, Asn-37, Gln-40;

BIM: Glu-145, Ile-146, Trp-147, Ile-148, Ala-149, Glu-151, Leu-152, Arg-153, Arg-154, Ile-155, Gly-156, Asp-157, Phe-159, Asn-160, Tyr-162, Tyr-163, Ala-164, Arg-165;

BID: Ile-82, Ile-83, Asn-85, Ile-86, Ala-87, His-89, Leu-90, Ala-91, Val-93, Gly-94, Asp-95, Met-97, Asp-98, Ie-101, Gly-104; and BAK: Gly-72, Val-74, Gly-75, Arg-76, Gln-77, Leu-78, Ala-79, Ile-81, Gly-82. Asp-83, Ile-85, Asn-86.

In some instances, stabilized peptides can have 1 to 10 amino acid substitutions (e.g., 1, 2, 3, 4, 5, 6, 7, 8, 9, or 10) in the non-interacting face of the helix of the stabilized peptide (i.e., the part of the helix that does not interact with Bfl-1). The "interacting face" of the polypeptides described herein includes those amino acid residues of the alpha helix that interact (e.g., interact specifically or bind specifically) with a BFL-1 protein. In certain instances, the peptides have 1 to 10, 1 to 9, 1 to 8, 1 to 7, 1 to 6, 1 to 5, 1 to 4, 1 to 3, or 1 to 2 amino substitutions in the interacting face of the helix of the peptide. In some instances, it can be useful to replace an amino acid on the interacting face of any one of SEQ ID NOS: 1-7 with another amino acid, e.g., Ala. In certain embodiments, the amino acid substitutions are conservative amino acid substitution(s). A conservative amino acid substitution is an amino acid substitution that does not alter the chemical makeup of the interacting face of the peptide. In some instances, the peptides described herein can include one of SEQ ID NOs:1-7 with one or more (e.g., 1, 2, 3, 4, 5, 6, 7, 8, or 9, or 1 to 2, 1 to 3, 1 to 4, 1 to 5, 1 to 6, 1 to 7, 1 to 8, or 1 to 9) conservative amino acid substitutions. Significant variability is permitted in the amino acids that are not on the interacting face of the helix of the peptides described herein. For example, almost all, if not all, of these amino acids can be substituted (e.g., with a conservative amino acid). In some cases the side chain of an amino acid is substituted so as to replace the amino acid with: 3S-1-pyrrolidine-3-carboxylic acid; D-homoproline; L-homoproline; isonipecotic acid; D-nipecotic acid; L-nipecotic acid; D-proline; L-proline; trans-4-dimethylaminocrotonic acid; and acrylic acid. In some cases, the peptide variant has an amino terminal group selected from: 3S-1-pyrrolidine-3-carboxylic acid; D-homoproline; L-homoproline; isonipecotic acid; D-nipecotic acid; L-nipecotic acid; D-proline; L-proline; trans-4-dimethylaminocrotonic acid; and acrylic acid. In certain cases, the warhead is not an amino acid. In some embodiments, the electrophilic moiety and peptide would be linked via a nitrogen containing heterocycle, either saturated (aziridine, diaziridine, azetidine, pyrrolidine, imidazolidine, pyrazolidine, oxazolidine, isoxazolidine, thiazolidine, isothiazolidine, piperidine, piperazine, morpholine, thiomorpholine, azepane) or unsaturated (azirine, diazirine, azete, pyrrole, imidazole, pyrazole, oxazole, isoxazole, thiazole, isothiazole, pyridine, diazines, oxazine, thiazine, azepine). The peptide and electrophile can also be linked by a substituted amino-functionalized ring (e.g. N-arylacrylamide) such as phenyl (aniline) or by more complex bicyclic or polycyclic rings, for instance, naphthalene, anthracene, phenanthrene, indole, isoindole, indolizine, quinolone, isoquinoline, quinoxaline, phthalzine, quinazoline, purine, carbazole, indazole, benzimidazole, azaindole. The electrophilic warhead in some embodiments is an acrylamide, or more generally defined as an α,β-unsaturated carbonyl, such as α-cyanoacrylamide, propiolamide, trans 4-dimethylamino-2-butenamide, or trans 4-piperidinyl-2-butenamide, or any other substituted acrylamide. In some cases, the stabilized peptide has the sequence of one SEQ ID NOs: 1-7 with one or two staples (e.g., one staple between two amino acids separated by 3 (or 6) amino acids or two staples each between two amino acids that are separated by 3 (or 6) amino acids). In addition, 1, 2, 3, 4 or 5 of the amino acids (whose side chains are not replaced with a staple) in this stabilized peptide can be replaced by a conservative substitution and the side chain of one amino acid is replaced by an electrophilic group that can react with the side chain of a cysteine residue. In some embodiments, the internal staple replaces the side chains of 2 amino acids, i.e., each staple is between two amino acids separated by, for example, 3, 4 or 6 amino acids. In some embodiments, the internal stitch replaces the side chains of 3 amino acids, i.e., the stitch is a pair of crosslinks between three amino acids separated by, for example, 3 and 6 amino acids.

In some instances, a "conservative amino acid substitution" can include substitutions in which one amino acid residue is replaced with another amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Methods for determining percent identity between amino acid sequences are known in the art. For example, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The determination of percent identity between two amino acid sequences is accomplished using the BLAST 2.0 program. Sequence comparison is performed using an ungapped alignment and using the default parameters (Blossom 62 matrix, gap existence cost of 11, per residue gapped cost of 1, and a lambda ratio of 0.85). The mathematical algorithm used in BLAST programs is described in Altschul et al. (Nucleic Acids Res. 25:3389-3402, 1997).

In the case of a cross-link between i and i+3 the cross-link can be a C7 alkylene or alkenylene. In the case of a cross-between i and i+4 the cross-link can be a C8 alkylene or alkenylene. In the case of a cross-link between i and i+7 the cross-link can be a C11, C12 or C13 alkylene or alkenylene. When the cross-link is an alkenylene there can one or more double bonds.

In the case of a cross-link between i and i+3 the cross-link can be a C6, CT, or C8 alkyl or alkene (e.g., a C6 alkene having a single double bond). In the case of a cross-link between i and i+4 the cross-link can be a C8 alkyl or alkene. In the case of a cross-link between i and i+7 the cross-link can be a C11, C12 or C13 alkyl or alkene (e.g., a C11 alkene having a single double bond). When the cross-link is an alkene there can be one or more double bonds.

"Peptide stapling" is a term coined from a synthetic methodology wherein two olefin-containing side-chains (e.g., cross-linkable side chains) present in a polypeptide chain are covalently joined (e.g., "stapled together") using a ring-closing metathesis (RCM) reaction to form acrosslinked ring (Blackwell et al., J. Org. Chem., 66: 5291-5302, 2001; Angew et al., Chem. Int. Ed. 37:3281, 1994). As used herein, the term "peptide stapling," includes the joining of two (e.g., at least one pair of) double bond-containing side-chains, triple bond-containing side-chains, or double bond-containing and triple bond-containing side chain, which may be present in a polypeptide chain, using any number of reaction conditions and/or catalysts to facilitate such a reaction, to provide a singly "stapled" polypeptide. The term "multiply stapled" polypeptides refers to those polypeptides containing more than one individual staple, and may contain two, three, or more independent staples of various spacings and compositions. Additionally, the term "peptide stitching," as used herein, refers to multiple and tandem "stapling" events in a single polypeptide chain to provide a "stitched" (e.g., tandem or multiply stapled) polypeptide, in which two staples, for example, are linked to a common residue. Peptide stitching is disclosed in WO 2008121767 and in WO 2010/068684, which are both hereby incorporated by reference. In some instances, staples, as used herein, can retain the unsaturated bond or can be reduced (e.g., as mentioned below in the stitching paragraph description).

While many peptide staples have all hydrocarbon cross-links, other type of cross-links or staples can be used. For example, triazole-containing (e.g, 1, 4 triazole or 1, 5 triazole) crosslinks can be used (Kawamoto et al. 2012 Journal of Medicinal Chemistry 55:1137; WO 2010/060112).

Stapling of a peptide using all-hydrocarbon cross-link has been shown to help maintain its native conformation and/or secondary structure, particularly under physiologically relevant conditions (Schafmiester et al., J. Am. Chem. Soc., 122:5891-5892, 2000: Walensky et al., Science, 305:1466-1470, 2004).

Stapling the polypeptide herein by an all-hydrocarbon crosslink predisposed to have an alpha-helical secondary structure can constrain the polypeptide to its native alpha-helical conformation. The constrained secondary structure may, for example, increase the peptide's resistance to proteolytic cleavage, may increase the peptide's thermal stability, may increase the peptide's hydrophobicity, may allow for better penetration of the peptide into the target cell's membrane, and/or may lead to an improvement in the peptide's biological activity relative to the corresponding uncrosslinked (e.g., "unstitched" or "unstapled") peptide.

Selection of amino acids for modification (e.g., to support an internal cross-link) can also be facilitated by staple scanning. The term "staple scan" refers to the synthesis of a library of stapled peptides whereby the location of the i and i+3: i and i+4; and i and i+7 single and multiple staple, or stitches, are positioned sequentially down the length of the peptide sequence, sampling all possible positions, to identify desired or optimal properties and activities for the stapled or stitched constructs. Examples of staple scanning methods are illustrated in the figures.

Suitable tethers are described herein and in US2005/0250680, PCT/US2008/058575, WO 2009/108261, and WO 2010/148335.

Amino acid side chains suitable for use in the peptides disclosed herein are known in the art. For example, suitable amino acid side chains include methyl (as the alpha-amino acid side chain for alanine is methyl), 4-hydroxyphenylmethyl (as the alpha-amino acid side chain for tyrosine is 4-hydroxyphenylmethyl) and thiomethyl (as the alpha-amino acid side chain for cysteine is thiomethyl), etc. A "terminally unsaturated amino acid side chain" refers to an amino acid side chain bearing a terminal unsaturated moiety, such as a substituted or unsubstituted, double bond (e.g., olefinic) or a triple bond (e.g., acetylenic), that participates in crosslinking reaction with other terminal unsaturated moieties in the polypeptide chain. In certain embodiments, a "terminally unsaturated amino acid side chain" is a terminal olefinic amino acid side chain. In certain embodiments, a "terminally unsaturated amino acid side chain" is a terminal acetylenic amino acid side chain. In certain embodiments, the terminal moiety of a "terminally unsaturated amino acid side chain" is not further substituted.

As noted above an internal tether or cross-link can extend across the length of one helical turn (i.e., about 3.4 amino acids (i.e., i, i+3, or i, i+4) or two helical turns (i.e., about 7 amino acids (i.e., i, i+7). Accordingly, amino acids positioned at i and i+3; i and i+4; or i and i+7 are ideal candidates for chemical modification and cross-linking. Thus, for example, where a peptide has the sequence . . . $Xaa_1$, $Xaa_2$, $Xaa_3$, $Xaa_4$, $Xaa_5$, $Xaa_6$, $Xaa_7$, $Xaa_8$, $Xaa_9$ . . .
(wherein, " . . . " indicates the optional presence of additional amino acids), cross-links between $Xaa_1$ and $Xaa_4$, or between $Xaa_1$ and $Xaa_5$, or between $Xaa_1$ and $Xaa_8$ are useful as are cross-links between $Xaa_2$ and $Xaa_5$, or between $Xaa_2$ and $Xaa_6$, or between $Xaa_2$ and $Xaa_9$, etc.

Polypeptides can include more than one crosslink within the polypeptide sequence to either further stabilize the sequence or facilitate the stabilization of longer polypeptide stretches. If the polypeptides are too long to be readily synthesized in one part, independently synthesized, cross-linked peptides can be conjoined by a technique called native chemical ligation (Bang, et al., J. Am. Chem. Soc. 126:1377). Alternately, large peptides are routinely synthesized using a convergent approach whereby fully protected fragments are specifically and sequentially reacted to form the full length desired product, after final deprotection, such as in the industrial synthesis of Fuzeon.

Peptides can contain one or more asymmetric centers and thus occur as racemates and racemic mixtures, single enantiomers, individual diastereomers and diastereomeric mixtures and geometric isomers (e.g. Z or cis and E or trans) of any olefins present. For example, peptides disclosed herein can exist in particular geometric or stereoisomeric forms, including, for example, cis- and trans-isomers, R- and S-enantiomers, diastereomers, (D)-isomers, (L)-isomers, the racemic mixtures thereof, and other mixtures thereof. Enantiomers can be free (e.g., substantially free) of their corresponding enantiomer, and/or may also be optically enriched. "Optically enriched," as used herein, means that the compound is made up of a significantly greater proportion of one enantiomer. In certain embodiments substantially free means that a composition contains at least about 90% by weight of a preferred enantiomer. In other embodiments the compound is made up of at least about 95%, 98%, or 99% by weight of a preferred enantiomer. Preferred enantiomers may be isolated from racemic mixtures using techniques known in the art, including, but not limited to, for example, chiral high pressure liquid chromatography (HPLC) and the formation and crystallization of chiral salts or prepared by asymmetric syntheses (see, e.g., Jacques, et al, Enantiomers, Racemates and Resolutions (Wiley Interscience, New York, 1981); Wilen, S. H., et al., Tetrahedron 33:2725 (1977); Eliel, EX. Stereochemistry of Carbon Compounds (McGraw-Hill, N Y, 1962); Wilen, S.H. Tables of Resolving Agents and Optical Resolutions p. 268 (EX. Eliel, Ed., Univ. of Notre Dame Press, Notre Dame, Ind. 1972). All such isomeric forms of these compounds are expressly included in the present invention.

Peptides can also be represented in multiple tautomeric forms, in such instances, the invention expressly includes all tautomeric forms of the compounds described herein (e.g., isomers in equilibrium (e.g., keto-enol), wherein alkylation at multiple sites can yield regioisomers), regioisomers, and oxidation products of the compounds disclosed herein (the invention expressly includes all such reaction products). All such isomeric forms of such compounds are included as are all crystal forms.

In some instances, the hydrocarbon tethers (i.e., cross links) described herein can be further manipulated. In one instance, a double bond of a hydrocarbon alkenyl tether, (e.g., as synthesized using a ruthenium-catalyzed ring closing metathesis (RCM)) can be oxidized (e.g., via epoxidation, aminohydroxylation or dihydroxylation) to provide one of compounds below.

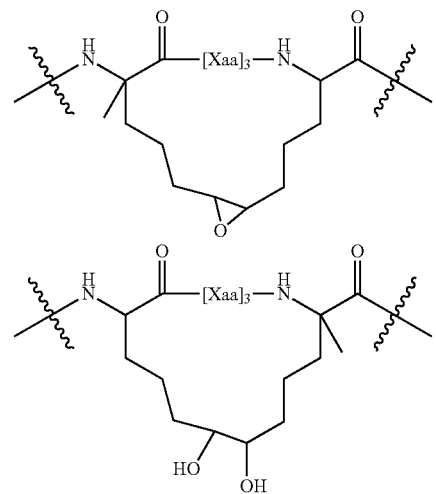

Either the epoxide moiety or one of the free hydroxyl moieties can be further functionalized. For example, the epoxide can be treated with a nucleophile, which provides additional functionality that can be used, for example, to attach a therapeutic agent. Such derivatization can alternatively be achieved by synthetic manipulation of the amino or carboxy-terminus of the polypeptide or via the amino acid side chain. Other agents can be attached to the functionalized tether, e.g., an agent that facilitates entry of the polypeptide into cells.

While hydrocarbon tethers have been described, other tethers are also envisioned. For example, the tether can include one or more of an ether, thioether, ester, amine, or amide moiety. In some cases, a naturally occurring amino acid side chain can be incorporated into the tether. For example, a tether can be coupled with a functional group such as the hydroxyl in serine, the thiol in cysteine, the primary amine in lysine, the acid in aspartate or glutamate, or the amide in asparagine or glutamine. Accordingly, it is possible to create a tether using naturally occurring amino acids rather than using a tether that is made by coupling two non-naturally occurring amino acids. It is also possible to use a single non-naturally occurring amino acid together with a naturally occurring amino acid.

It is further envisioned that the length of the tether can be varied. For instance, a shorter length of tether can be used where it is desirable to provide a relatively high degree of constraint on the secondary alpha-helical structure, whereas, in some instances, it is desirable to provide less constraint on the secondary alpha-helical structure, and thus a longer tether may be desired.

Additionally, while examples of tethers spanning from amino acids i to i+3, i to i+4; and i to i+7 have been described in order to provide a tether that is primarily on a single face of the alpha helix, the tethers can be synthesized to span any combinations of numbers of amino acids.

In some instances, alpha disubstituted amino acids are used in the polypeptide to improve the stability of the alpha helical secondary structure. However, alpha disubstituted amino acids are not required, and instances using mono-alpha substituents (e.g., in the tethered amino acids) are also envisioned.

The stapled polypeptides can include a drug, a toxin, a derivative of polyethylene glycol; a second polypeptide; a carbohydrate, etc. Where a polymer or other agent is linked to the stapled polypeptide is can be desirable for the composition to be substantially homogeneous.

The addition of polyethelene glycol (PEG) molecules can improve the pharmacokinetic and pharmacodynamic properties of the polypeptide. For example, PEGylation can reduce renal clearance and can result in a more stable plasma concentration.

PEG is a water soluble polymer and can be represented as linked to the polypeptide as formula:

$XO-(CH_2CH_2O)_n-CH_2CH_2-Y$ where n is 2 to 10,000 and X is H or a terminal modification, e.g., a C1 alkyl; and Y is an amide, carbamate or urea linkage to an amine group (including but not limited to, the epsilon amine of lysine or the N-terminus) of the polypeptide. Y may also be a maleimide linkage to a thiol group (including but not limited to, the thiol group of cysteine). Other methods for linking PEG to a polypeptide, directly or indirectly, are known to those of ordinary skill in the art. The PEG can be linear or branched. Various forms of PEG including various functionalized derivatives are commercially available.

PEG having degradable linkages in the backbone can be used. For example, PEG can be prepared with ester linkages that are subject to hydrolysis. Conjugates having degradable PEG linkages are described in WO 99/34833; WO 99/14259, and U.S. Pat. No. 6,348,558.

In certain embodiments, macromolecular polymer (e.g., PEG) is attached to an agent described herein through an intermediate linker. In certain embodiments, the linker is made up of from 1 to 20 amino acids linked by peptide bonds, wherein the amino acids are selected from the 20 naturally occurring amino acids. Some of these amino acids may be glycosylated, as is well understood by those in the art. In other embodiments, the 1 to 20 amino acids are selected from glycine, alanine, proline, asparagine, glutamine, and lysine. In other embodiments, a linker is made up of a majority of amino acids that are sterically unhindered, such as glycine and alanine. Non-peptide linkers are also possible. For example, alkyl linkers such as $-NH(CH_2)_nC(O)-$, wherein n=2-20 can be used. These alkyl linkers may further be substituted by any non-sterically hindering group such as lower alkyl (e.g., $C_1$-$C_6$) lower acyl, halogen (e.g., Cl, Br), CN, $NH_2$, phenyl, etc. U.S. Pat. No. 5,446,090 describes a bifunctional PEG linker and its use in forming conjugates having a peptide at each of the PEG linker termini.

The stapled peptides can also be modified, e.g., to further facilitate cellular uptake or increase in vivo stability, in some embodiments. For example, acylating or PEGylating a peptidomimetic macrocycle facilitates cellular uptake, increases bioavailability, increases blood circulation, alters pharmacokinetics, decreases immunogenicity and/or decreases the needed frequency of administration.

In some embodiments, the stapled peptides disclosed herein have an enhanced ability to penetrate cell membranes (e.g., relative to non-stapled peptides).

Methods of synthesizing the compounds of the described herein are known in the art. Nevertheless, the following exemplary method may be used. It will be appreciated that the various steps may be performed in an alternate sequence or order to give the desired compounds. Synthetic chemistry transformations and protecting group methodologies (protection and deprotection) useful in synthesizing the compounds described herein are known in the art and include, for example, those such as described in R Larock, Comprehensive Organic Transformations, VCH Publishers (1989); T. W. Greene and P. G. M. Wuts, Protective Groups in Organic Synthesis, 3d. Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis. John Wiley and Sons (1995), and subsequent editions thereof.

The peptides of this invention can be made by chemical synthesis methods, which are well known to the ordinarily skilled artisan. See, for example, Fields et al., Chapter 3 in Synthetic Peptides: A User's Guide, ed. Grant, W. H. Freeman & Co., New York, N.Y., 1992, p. 77. Hence, peptides can be synthesized using the automated Merrifield techniques of solid phase synthesis with the $\alpha$-$NH_2$ protected by either t-Boc or Fmoc chemistry using side chain protected amino acids on, for example, an Applied Biosystems Peptide Synthesizer Model 430A or 431.

One manner of making of the peptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups.

Longer peptides could be made by conjoining individual synthetic peptides using native chemical ligation. Alternatively, the longer synthetic peptides can be synthesized by well-known recombinant DNA techniques. Such techniques are provided in well-known standard manuals with detailed protocols. To construct a gene encoding a peptide of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

The peptides can be made in a high-throughput, combinatorial fashion, e.g., using a high-throughput multiple channel combinatorial synthesizer available from Advanced Chemtech.

Peptide bonds can be replaced, e.g., to increase physiological stability of the peptide, by: a retro-inverso bonds (C(O)—NH); a reduced amide bond (NH—$CH_2$); a thiomethylene bond (S—$CH_2$ or $CH_2$—S): an oxomethylene bond (O—$CH_2$ or $CH_2$—O); an ethylene bond ($CH_2$—$CH_2$); a thioamide bond (C(S)—NH); a trans-olefin bond (CH=CH): a fluoro substituted trans-olefin bond (CF=CH); a ketomethylene bond (C(O)—CHR) or CHR—C(O) wherein R is H or $CH_3$; and a fluoro-ketomethylene bond (C(O)—CFR or CFR—C(O) wherein R is H or F or $CH_3$.

The polypeptides can be further modified by: acetylation, amidation, biotinylation, cinnamoylation, farnesylation, fluoresceination, formylation, myristoylation, palmitoylation, phosphorylation (Ser, Tyr or Thr), stearoylation, succinylation and sulfurylation. As indicated above, peptides can be conjugated to, for example, polyethylene glycol (PEG); alkyl groups (e.g., C1-C20 straight or branched alkyl groups); fatty acid radicals; and combinations thereof.

α, α-Disubstituted non-natural amino acids containing olefinic side chains of varying length can be synthesized by known methods (Williams et al. J. Am. Chem. Soc., 113: 9276, 1991; Schafmeister et al., J. Am. Chem Soc., 122: 5891, 2000; and Bird et al., Methods Enzymol., 446:369, 2008; Bird et al, Current Protocols in Chemical Biology, 2011). For peptides where an i linked to i+7 staple is used (two turns of the helix stabilized) either: a) one S5 amino acid and one R8 is used; or b) one S8 amino acid and one R5 amino acid is used. R8 is synthesized using the same route, except that the starting chiral auxillary confers the R-alkyl-stereoisomer. Also, 8-iodooctene is used in place of 5-iodopentene. Inhibitors are synthesized on a solid support using solid-phase peptide synthesis (SPPS) on MBHA resin (see. e.g., WO 2010/148335).

Fmoc-protected α-amino acids (other than the olefinic amino acids Fmoc-$S_5$-OH, Fmoc-$R_8$-OH, Fmoc-$R_8$-OH, Fmoc-$S_8$-OH and Fmoc-$R_5$-OH), 2-(6-chloro-1-H-benzotriazole-1-yl)-1,1,3,3-tetramethylaminium hexafluorophosphate (HCTU), and Rink Amide MBHA are commercially available from, e.g., Novabiochem (San Diego, Calif.). Dimethylformamide (DMF), N-methyl-2-pyrrolidinone (NMP), N,N-diisopropylethylamine (DIEA), trifluoroacetic acid (TFA), 1,2-dichloroethane (DCE), fluorescein isothiocyanate (FITC), and piperidine are commercially available from, e.g., Sigma-Aldrich. Olefinic amino acid synthesis is reported in the art (Williams et al., Org. Synth., 80:31, 2003).

Again, methods suitable for obtaining (e.g., synthesizing), stapling, and purifying the peptides disclosed herein are also known in the art (see, e.g., Bird et. al., Methods in Enzymol., 446:369-386 (2008); Bird et al, Current Protocols in Chemical Biology, 2011; Walensky et al., Science, 305:1466-1470 (2004); Schafineister et al., J. Am. Chem. Soc., 122:5891-5892 (2000); U.S. patent application Ser. No. 12/525,123, filed Mar. 18, 2010; and U.S. Pat. No. 7,723,468, issued May 25, 2010, each of which are hereby incorporated by reference in their entirety).

In some embodiments, the peptides are substantially free of non-stapled peptide contaminants or are isolated. Methods for purifying peptides include, for example, synthesizing the peptide on a solid-phase support. Following cyclization, the solid-phase support may be isolated and suspended in a solution of a solvent such as DMSO, DMSO/dichloromethane mixture, or DMSO/NMP mixture. The DMSO/dichloromethane or DMSO/NMP mixture may comprise about 30%, 40%, 50% or 60% DMSO. In a specific embodiment, a 50%/50% DMSO/NMP solution is used. The solution may be incubated for a period of 1, 6, 12 or 24 hours, following which the resin may be washed, for example with dichloromethane or NMP. In one embodiment, the resin is washed with NMP. Shaking and bubbling an inert gas into the solution may be performed.

Properties of the cross-linked polypeptides of the invention can be assayed, for example, using the methods described below.

Assays to Determine α-Helicity: Compounds are dissolved in an aqueous solution (e.g. 5 mM potassium phosphate solution at pH 7, or distilled $H_2O$, to concentrations of 25-50 µM). Circular dichroism (CD) spectra are obtained on a spectropolarimeter (e.g., Jasco J-710, Aviv) using standard measurement parameters (e.g. temperature, 20° C.; wavelength, 190-260 nm; step resolution, 0.5 nm; speed, 20 nm/sec; accumulations, 10; response, 1 sec; bandwidth, 1 nm; path length, 0.1 cm). The α-helical content of each peptide is calculated by dividing the mean residue ellipticity by the reported value for a model helical decapeptide (Yang et al., Methods Enzymol. 130:208 (1986)).

Assays to Determine Melting Temperature (Tm): Crosslinked or the unmodified template peptides are dissolved in distilled $H_2O$ or other buffer or solvent (e.g. at a final concentration of 50 µM) and Tm is determined by measuring the change in ellipticity over a temperature range (e.g. 4 to 95° C.) on a spectropolarimeter (e.g., Jasco J-710, Aviv) using standard parameters (e.g. wavelength 222 nm; step resolution, 0.5 nm; speed, 20 nm/sec; accumulations, 10; response, 1 sec; bandwidth, 1 nm; temperature increase rate: 1° C./min; path length, 0.1 cm).

In Vitro Protease Resistance Assays: The amide bond of the peptide backbone is susceptible to hydrolysis by proteases, thereby rendering peptidic compounds vulnerable to rapid degradation in vivo. Peptide helix formation, however, typically buries and/or twists and/or shields the amide backbone and therefore may prevent or substantially retard proteolytic cleavage. The peptidomimetic macrocycles of the present invention may be subjected to in vitro enzymatic proteolysis (e.g. trypsin, chymotrypsin, pepsin) to assess for any change in degradation rate compared to a corresponding uncrosslinked or alternatively stapled polypeptide. For example, the peptidomimetic macrocycle and a corresponding uncrosslinked polypeptide are incubated with trypsin agarose and the reactions quenched at various time points by centrifugation and subsequent HPLC injection to quantitate the residual substrate by ultraviolet absorption at 280 nm. Briefly, the peptidomimetic macrocycle and peptidomimetic precursor (5 mcg) are incubated with trypsin agarose (Pierce) (S/E ~125) for 0, 10, 20, 90, and 180 minutes. Reactions are quenched by tabletop centrifugation at high speed; remaining substrate in the isolated supernatant is quantified by HPLC-based peak detection at 280 nm. The proteolytic reaction displays first order kinetics and the rate constant, k, is determined from a plot of ln[S] versus time.

Peptidomimetic macrocycles and/or a corresponding uncrosslinked polypeptide can be each incubated with fresh mouse, rat and/or human serum (e.g. 1-2 mL) at 37° C. for, e.g., 0, 1, 2, 4, 8, and 24 hours. Samples of differing macrocycle concentration may be prepared by serial dilution with serum. To determine the level of intact compound, the following procedure may be used: The samples are extracted, for example, by transferring 100 µL of sera to 2 ml centrifuge tubes followed by the addition of 10 µL of 50% formic acid and 500 μL acetonitrile and centrifugation at 14,000 RPM for 10 min at 4+/−2° C. The supernatants are then transferred to fresh 2 ml tubes and evaporated on Turbovap under $N_2$<10 psi, 37° C. The samples are reconstituted in 100 μL of 50:50 acetonitrile:water and submitted to LC-MS/MS analysis. Equivalent or similar procedures for testing ex vivo stability are known and may be used to determine stability of macrocycles in serum.

In Vivo Protease Resistance Assays: A key benefit of peptide stapling is the translation of in vitro protease resistance into markedly improved pharmacokinetics in vivo.

In vitro Binding Assays: To assess the binding and affinity of peptidomimetic macrocycles and peptidomimetic precursors to acceptor proteins, a fluorescence polarization assay (FPA) can be used, for example. The FPA technique measures the molecular orientation and mobility using polarized light and fluorescent tracer. When excited with polarized light, fluorescent tracers (e.g., FITC) attached to molecules with high apparent molecular weights (e.g. FITC-labeled peptides bound to a large protein) emit higher levels of polarized fluorescence due to their slower rates of rotation as compared to fluorescent tracers attached to smaller molecules (e.g. FITC-labeled peptides that are free in solution).

Pharmaceutical Compositions

One or more of the stabilized peptides disclosed herein (e.g., one or more of SEQ ID NOs: 22-36 and 41-119, or one or more of the peptides in FIG. 18) can be formulated for use as or in pharmaceutical compositions. In certain embodiments, the pharmaceutical composition comprises an amino acid sequence that is identical to an amino acid sequence set forth in SEQ ID NOs: 22-36 and 41-119, or one or more of the peptides in FIG. 18, except for 1 to 10, 1 to 9, 1 to 8, 1 to 7, 1 to 6, 1 to 5, 1 to 4, 1 to 3, 1 to 2, or 1 amino acid substitution, insertion, or deletion. These changes to the amino acid sequences can be made on the Bfl-1 non-interacting alpha-helical face of these peptides and/or on the Bfl-1 interacting alpha-helical face. Such compositions can be formulated or adapted for administration to a subject via any route, e.g., any route approved by the Food and Drug Administration (FDA). Exemplary methods are described in the FDA's CDER Data Standards Manual, version number 004 (which is available at fda.give/cder/dsm/DRG/drg00301.htm). For example, compositions can be formulated or adapted for administration by inhalation (e.g., oral and/or nasal inhalation (e.g., via nebulizer or spray)), injection (e.g., intravenously, intra-arterial, subdermally, intraperitoneally, intramuscularly, and/or subcutaneously); and/or for oral administration, transmucosal administration, and/or topical administration (including topical (e.g., nasal) sprays and/or solutions).

In some instances, pharmaceutical compositions can include an effective amount of one or more stabilized peptides. The terms "effective amount" and "effective to treat," as used herein, refer to an amount or a concentration of one or more compounds or a pharmaceutical composition described herein utilized for a period of time (including acute or chronic administration and periodic or continuous administration) that is effective within the context of its administration for causing an intended effect or physiological outcome (e.g., treatment of infection).

Pharmaceutical compositions of this invention can include one or more peptides and any pharmaceutically acceptable carrier and/or vehicle. In some instances, pharmaceuticals can further include one or more additional therapeutic agents in amounts effective for achieving a modulation of disease or disease symptoms.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, may also be advantageously used to enhance delivery of compounds of the formulae described herein.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intra-cutaneous, intra-venous, intra-muscular, intra-articular, intra-arterial, intra-synovial, intra-sternal, intra-thecal, intra-lesional and intra-cranial injection or infusion techniques.

Pharmaceutical compositions can be in the form of a solution or powder for inhalation and/or nasal administration. Such compositions may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

Pharmaceutical compositions can be orally administered in any orally acceptable dosage form including, but not limited to, capsules, tablets, emulsions and aqueous suspensions, dispersions and solutions. In the case of tablets for oral use carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

Alternatively or in addition, pharmaceutical compositions can be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

In some instances, one or more peptides disclosed herein can be conjugated, for example, to a carrier protein. Such conjugated compositions can be monovalent or multivalent. For example, conjugated compositions can include one peptide disclosed herein conjugated to a carrier protein. Alternatively, conjugated compositions can include two or more peptides disclosed herein conjugated to a carrier.

As used herein, when two entities are "conjugated" to one another they are linked by a direct or indirect covalent or non-covalent interaction. In certain embodiments, the association is covalent. In other embodiments, the association is non-covalent. Non-covalent interactions include hydrogen bonding, van der Waals interactions, hydrophobic interactions, magnetic interactions, electrostatic interactions, etc. An indirect covalent interaction is when two entities are covalently connected, optionally through a linker group.

Carrier proteins can include any protein that increases or enhances immunogenicity in a subject. Exemplary carrier proteins are described in the art (see, e.g., Fattom et al., Infect. Immun., 58:2309-2312, 1990; Devi et al., Proc. Natl. Acad. Sci. USA 88:7175-7179, 1991; Li et al., Infect. Immun. 57:3823-3827, 1989; Szu et al., Infect. Immun. 59:4555-4561, 1991; Szu et al., J. Exp. Med. 166:1510-1524, 1987; and Szu et al., Infect. Immun. 62:4440-4444, 1994). Polymeric carriers can be a natural or a synthetic material containing one or more primary and/or secondary amino groups, azido groups, or carboxyl groups. Carriers can be water soluble.

Methods of Treatment

The disclosure includes methods of using any of the peptides described herein for the prophylaxis and/or treatment of cancer. The terms "treat" or "treating," as used herein, refers to partially or completely alleviating, inhibiting, ameliorating, and/or relieving the disease or condition from which the subject is suffering.

The peptides described herein can be useful for treating a human subject with a Bfl-1-expressing cancer. The peptides described herein can also be useful for treating a human subject with a Bfl-1-dependent cancer. In certain embodiments, the cancer is a melanoma, a leukemia, or a lymphoma.

In general, methods include selecting a subject and administering to the subject an effective amount of one or more of the peptides herein, e.g., in or as a pharmaceutical composition, and optionally repeating administration as required for the prophylaxis or treatment of a cancer, e.g., melanoma or lymphoma, and can be administered orally, intravenously or topically. A subject can be selected for treatment based on, e.g., determining that the subject has a cancer that expresses Bfl-1. The peptides of this disclosure can be used to determine if a subject's cancer expresses Bfl-1, or if a subject's cancer is dependent on Bfl-1.

Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments. For example, effective amounts can be administered at least once.

EXAMPLES

Example 1: Preparation of Stapled NOXA Peptides

Structurally-stabilized alpha-helical NOXA-related peptides were prepared by substituting non-natural amino acids with olefinic side chains at [i, i+4] positions in peptides having the sequence of the NOXA BH3 domain followed by ruthenium catalyzed olefin metathesis to yield NOXA SAHB peptides. Variants having deletions or substitutions in the NOXA sequence were prepared in a similar manner. A number of such peptides are depicted in FIG. 2. Fluorescent derivatives of the peptides were utilized in fluorescence polarization binding assays for to assess binding affinities to MCL-1 and Bfl-1.

These studies revealed that when F32 of the NOXA sequence was mutated to an amino acid with a bulkier side chain, the binding exhibited selectivity for Bfl-1 over MCL-1 (FIG. 3A). This might be due to the fact that there is smaller cleft in the MCL-1 binding pocket where modelling suggest F32 is directed, so bulkier residues are not tolerated as well as in the Bfl-1 pocket. A second panel of NOXA variants with substitutions at F32 was synthesized. These variants have variety of bulky side chains at the F32 position. These variants are depicted in FIG. 3B. F32 substitutions imparting greater selectivity for BFL-1 over BCL-1 include: Phe(3-I), Phe(4-I) and Phe(3,4 $CL_2$)

Example 2: Investigation of Disulfide Bond Formation

Figure 4A:
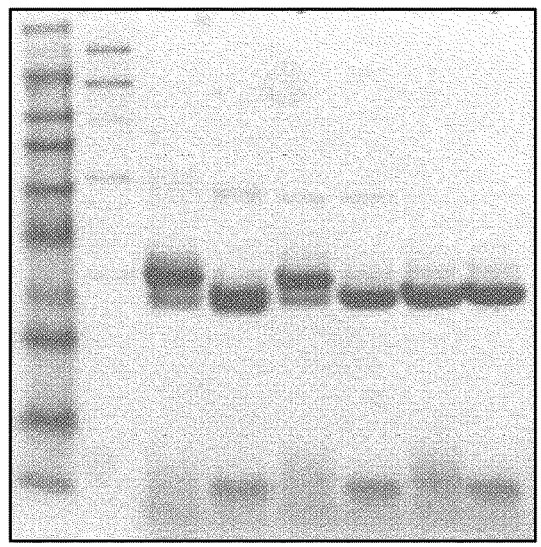
FIG. 4A: Depicts the results of studies assessing the binding of various NOXA SAHB peptides with and without C25S substitution to Bfl-1.
Figure 4B:
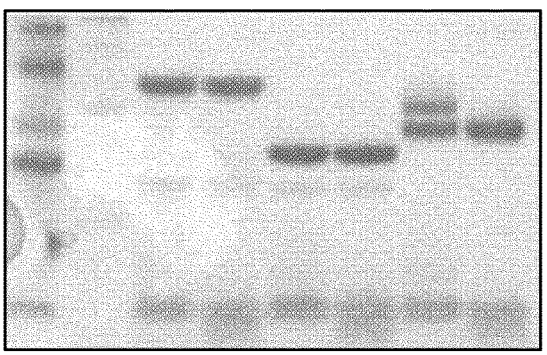
FIG. 4B: Depicts the results of studies assessing the binding of various NOXA SAHB peptides with and without C25S substitution to Bfl-1, MCL-1 and BCL-$X_L$.

Next, the impact of the Cys25 in NOXA was investigated. Modeling suggests that Bfl-1 and NOXA have cysteine residues located near each other when the two proteins are bound to each other. The distance between the sulfurs of the cysteine residues is 3.5 A according to the previously determined crystal structure of the bound proteins (PDB ID 3MQP). In contrast, modeling indicates that MCL-1 does not have a cysteine in close proximity to its NOXA BH3 binding pocket. To examine the impact of Cys25 in NOXA on target interaction, we examined the binding of WT NOXA SAHB and NOXA C25S SAHB to Bfl-1 and to a variety of Bfl-1 cysteine mutants. In vitro conjugation assays were performed in order to verify the formation of the disulfide bond. Global reduction of the protein and the NOXA peptides, followed by the introduction of an oxidant such as GSSG led to production of a disulfide bond, shown as a 3 kDa shift on non-reducing SDS-PAGE (FIG. 4A). When the opportunity for disulfide bond formation was eliminated by introducing a C25S substitution into NOXA SAHB, the binding difference was eliminated, the NOXA C25S SAHB bound with similar affinity to both Bfl-1- and MCL-I, demonstrating that the NOXA SAHB alone did not confer specificity to Bfl-1, but rather the formation of the disulfide bond that can make NOXA selective for Bfl-1. (FIG. 4A). Similar experiments using BCL-XL and MCL-1 demonstrate that only Bfl-1 forms a covalent bond with NOXA, even though BCL-XL and MCL-1 also contain cysteines within their sequences. This shows that NOXA Cys25 is specific for Bfl-1 Cys55 and that the disulfide bond formation is specific (FIG. 4B)

Example 3: Investigation of the Functional Impact of Disulfide Bond Formation

Figure 5A:
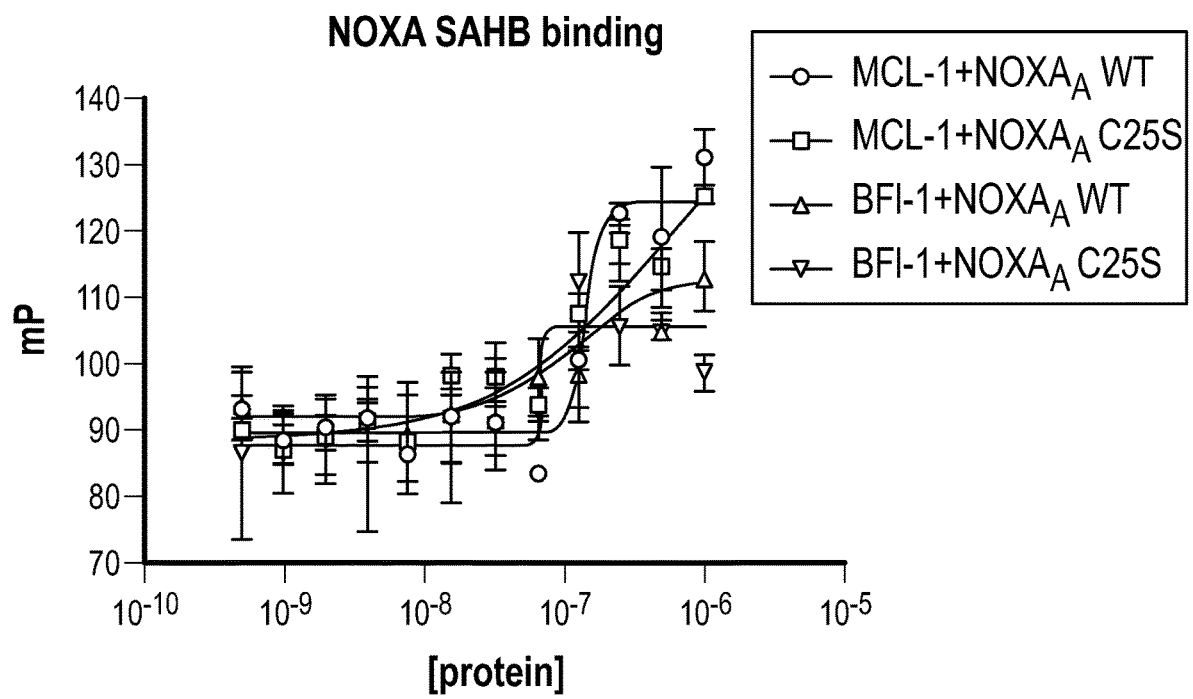
FIG. 5A: Depicts the results of binding studies showing that Cys25 of NOXA exclusively interacts with Bfl-1 Cys55, as demonstrated by testing of Bfl-1 C55S constructs.
Figure 5B:
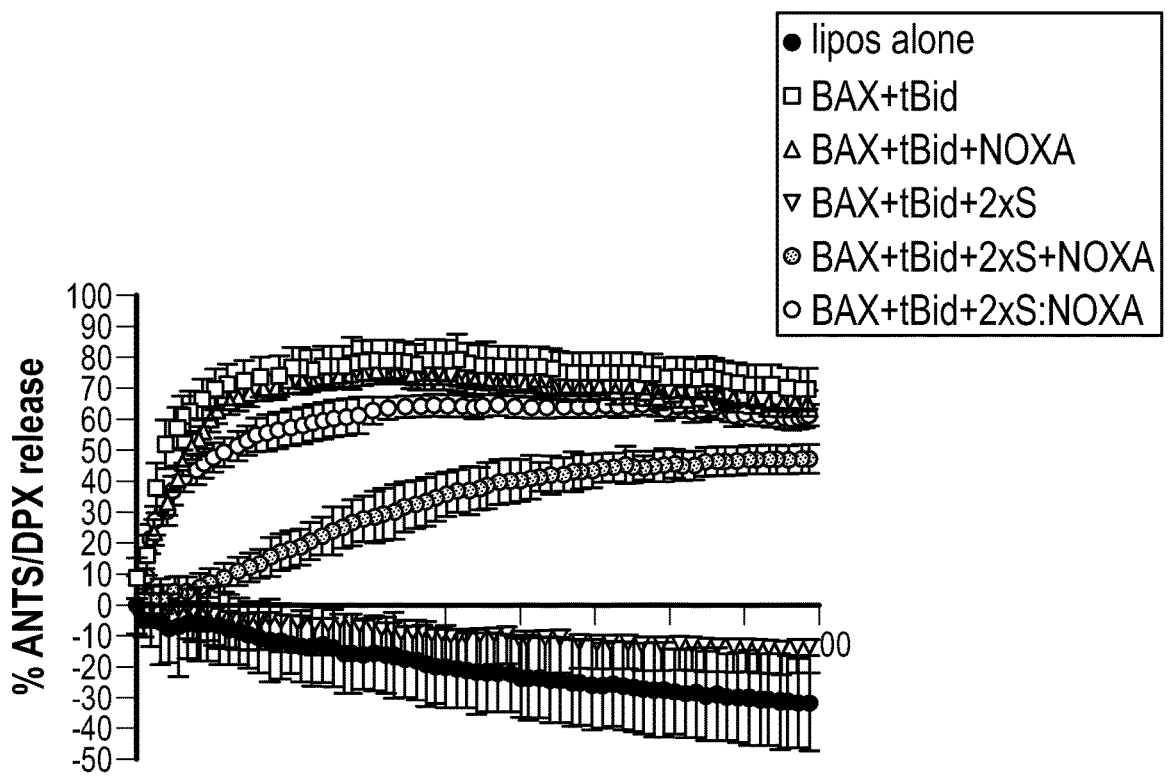
FIG. 5B: Depicts the results of studies showing that formation of a Bfl-1:NOXA disulfide bond prior to liposomal release assay abrogates the anti-apoptotic effects of Bfl-1 on BAX activation and liposomal dye release.

The functional impact of the Bfl-1:NOXA disulfide bond formation was evaluated using competitive binding assays and liposomal release assays. Pre-forming the Bfl-1:NOXA disulfide bond prior to exposure binding to another FITC BH3 domain significantly decreased the availability of the Bfl-1 binding pocket even after reaching solution binding equilibrium. Use of the NOXA C25S SAHB or Bfl-1 C55S constructs abrogated these inhibitory effects. Bfl-1 alone in the liposomal release assay inhibits activation of BAX and subsequent pore formation in the liposomes. When NOXA was added concurrently with Bfl-1, the anti-apoptotic effects of Bfl-1 on BAX were somewhat inhibited. Importantly, allowing formation of the Bfl-1:NOXA disulfide bond prior to performing the liposomal release assay almost completely abrogates the effects of Bfl-1 and restores BAX activity back to that of the positive control. (FIG. 5A and FIG. 5B).

Example 4: Modification of Peptide to Include Electrophilic Warheads

To create additional NOXA SAHB variants with the potential to form a covalent bond with Cys55 of Bfl-1, we generated a number of variants in which a "warhead" replaced either Cys25 or Leu21, both of which are expected to be within 4 A of Cys55 of Bfl-1 when NOXA SAHB binds to Bfl-1. The various NOXA SAHB warhead variants are depicted in FIG. 6. In addition, warhead variants of other BH3 peptides, BIM1. BIM2. BAK, and BOK were designed. In these depictions, J indicates the position of the warhead.

FIG. 7A depicts variant amino acids that can be used to create hydrocarbon staples of various lengths. FIG. 7B depicts how the variant amino acids can be used to create staples (internal cross-links) on various lengths.

Figure 8A:
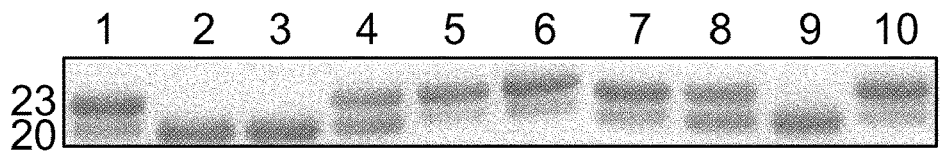
FIG. 8A: Depicts the results of a study showing that several NOXA SAHB warhead peptides bind to Bfl-1 under reducing conditions The electrophilic substitution are: 1=3S-1-pyrrolidine-3-carboxylic acid, 2=D-homoproline, 3=L-homoproline, 4=isonipecotic acid, 5=D-nipecotic acid, 6=L-nipecotic acid, 7=D-proline, 8=L-proline, 9=trans-4-dimethylaminocrotonic acid, 10=acrylic acid.

Various warhead SAHBs were tested in conjugation assays with Bfl-1, and when compared to the disulfide bond, the covalent binding efficiency for several warheads was much higher, >90% for warheads compared to about 75% for disulfide bonds. D-homoproline, L-homoproline and trans-4-dimethylaminocrotonic acid were less efficient (FIG. 8A).

Figure 8B:
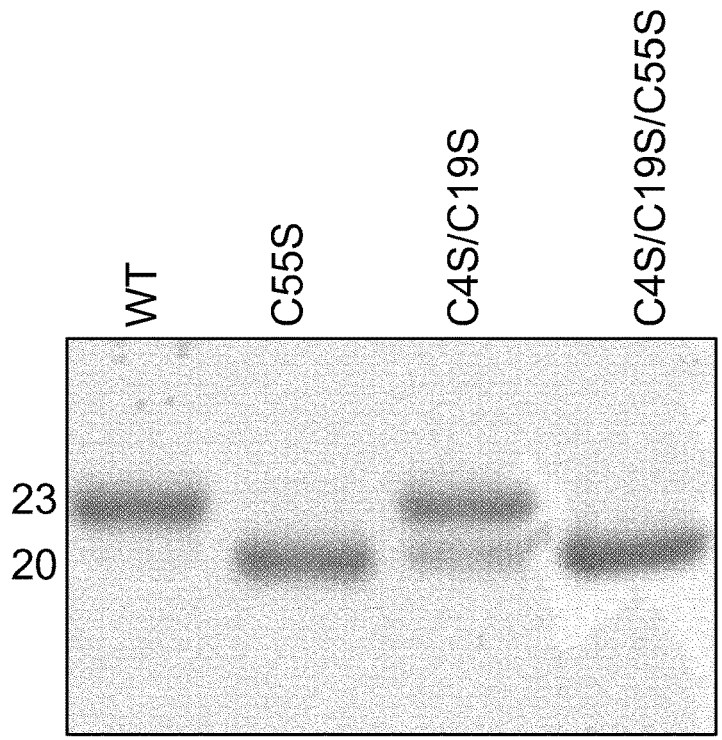
FIG. 8B: Depicts the results of studies using Bfl-1 Cys to Ser mutants verifying that Bfl-1 Cys55, found within the binding pocket, is the only cysteine residue necessary for binding to the NOXA SAHB warhead peptides.
Figure 8C:
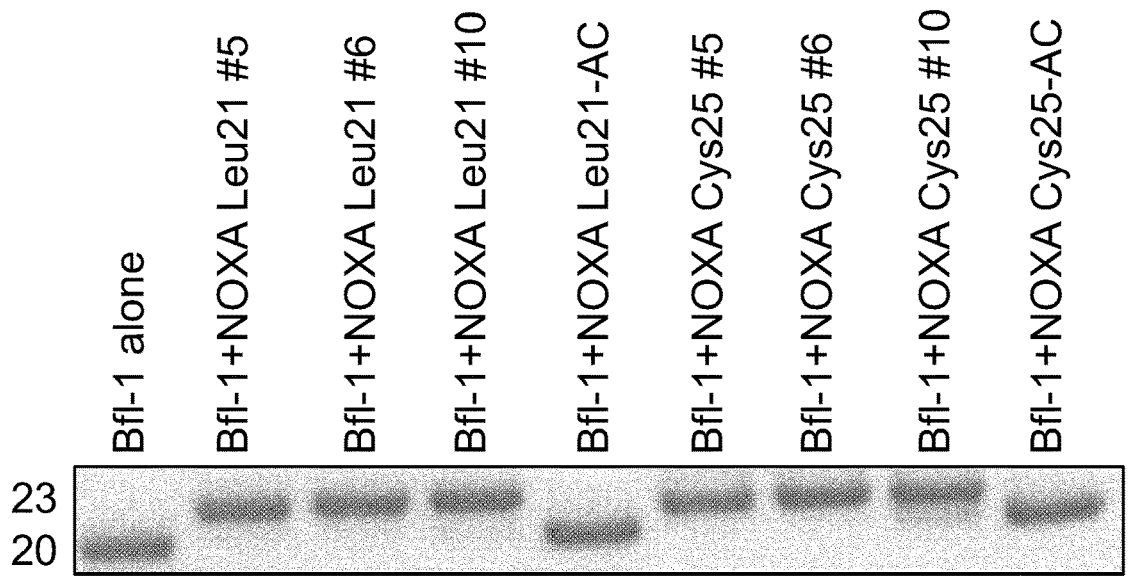
FIG. 8C: Depicts the results of studies showing Bfl-1 forming covalent conjugates with various NOXA warhead stapled peptides, wherein the warhead N-terminates the sequence and replaces first NOXA Leu21 and then Cys25. Linker 5, 6, and 10 are all similar except for "Ac", in which the peptide is capped with acetyl.

To assess whether the reactive warheads reacted substantially with off-target cysteines, we examined the binding in the presence of E. coli lysate or cell culture media with added BSA. No detectable off target binding was found. The NOXA warhead SAHBs interact solely with Cys55 on Bfl-1 (FIG. 8B) BIM and BAX warhead SAHBs were also tested for Bfl-1 binding efficiency with the same results, showing that the proline-based warhead moieties can create an efficient and covalent bond with Bfl-1, both under reducing and non-reducing conditions. This is an improvement on the disulfide bond originally discovered between Bfl-1 and NOXA, which exists in sufficient quantity only under oxidizing conditions.

Figure 9A:
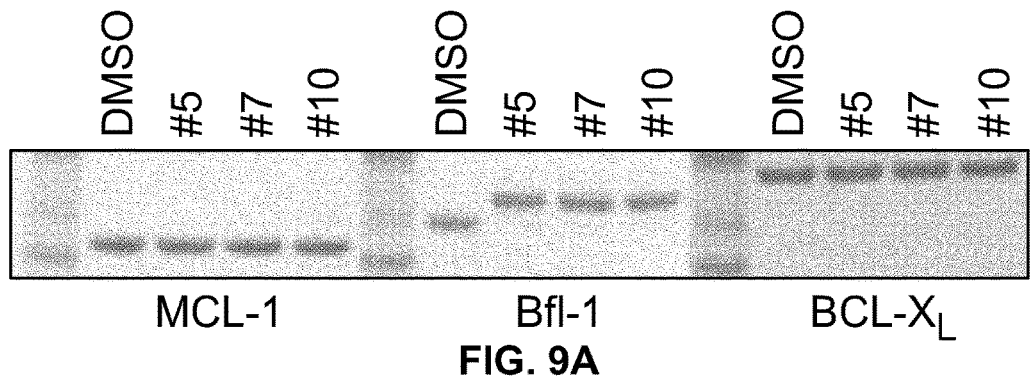
FIG. 9A: Depicts the results of a study showing that when selected NOXA warhead SAHBs were contacted to MCL-1, Bfl-1 and BCL-$X_L$, only Bfl-1 had a molecular weight shift in the presence of the SAHBs.
Figure 9B:
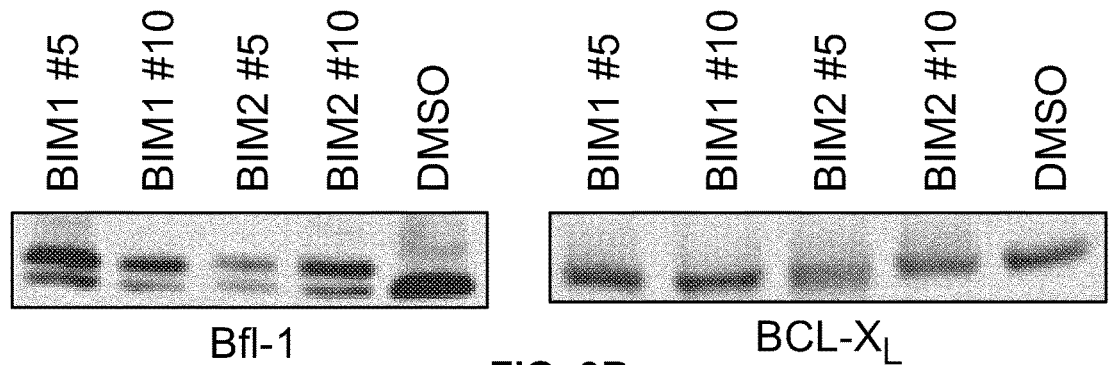
FIG. 9B: *E. coli* lysate overexpressing Bfl-1 and BCL-$X_L$ were spiked with BIM warhead SAHBs or DMSO and a Western blot run to test for molecular weight shifts. Only Bfl-1 displayed a molecular weight shift with the addition of BM warhead SAHBs.
Figure 9C:
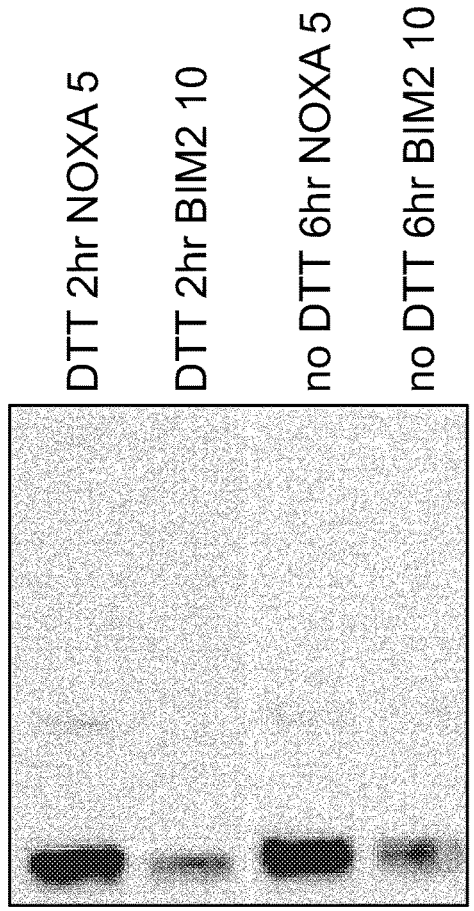
FIG. 9C: Cell culture media spiked with BSA, Bfl- and Btn-NOXA or BIM warhead SAHBs were Western blotted for biotin and displayed no nonspecific binding to other proteins found in the media, with bands only seen at 20 kDa for Bfl-1.

Warhead SAHBs were also tested for their binding to other antiapoptotic BCL-2 family members, which do contain cysteine residues, but not within the binding pocket. NOXA and BIM warhead SAHBs did not interact with cysteines on BCL-XL or MCL-1 FIG. 9A), even though the original BIM stapled peptides are promiscuous binders and NOXA stapled peptides interact with both Bfl-1 and MCL-1-. These results were also seen in E. coli lysate immunoblots (FIG. 9B) and cell media containing BSA (35 cysteine residues), which was spiked with Bfl-1 (FIG. 9C). Overall, the NOXA and BIM warhead SAHBs are Bfl-1 specific binders with much higher efficiency than the prototype cysteine.

Methods Used in Examples 1-4

Solid phase peptide synthesis: Fmoc-based solid-phase peptide synthesis was used to synthesize the peptides and their stapled derivatives. To achieve the various staple lengths, α-methyl, α-alkenyl amino acids were used flanking two, three or six residues. The R5 residue were incorporated at position i and S5 at position i+3, while two S5 residues were used at the i and i+4 locations, and an R8 at position i and S5 at i+7[29]. For the stapling reaction. Grubbs 1st generation ruthenium catalyst dissolved in dichloroethane was added to the peptides while still on resin. To ensure maximal conversion, three to five rounds of stapling were performed. Once stapled, the peptides were cleaved off the resin using trifluoroacetic acid, then precipitated using a hexane:ether (1:1) mixture, and afterwards they were air dried and purified using LC-MS. We performed amino acid analysis both to precisely determine the amount of peptide purified and to ensure the correct sequence was made.

Fluorescence polarization assay: The solution-state equilibrium binding assay was used to determine binding affinities of the stapled peptides to the anti-apoptotic proteins. Proteins were serially diluted from 1 µM, then combined with FITC-labeled SAHB and polarization measured at 5 min on a microplate reader. We then calculated dissociation constants ($K_D$) by nonlinear regression analysis of dose-response curves.

Bfl-1:NOXA conjugation assay: The conjugation assay was developed to test for disulfide bond formation in a non-reducing environment, 3:1 FITC-stapled peptide:protein molar ratio was combined in the presence of DTT, then diluted and incubated with 1.2 molar excess GSSG. Samples were then run on non-reducing SDS-PAGE, scanned for fluorescence, then stained with Coomassie.

Liposomal release assay: Large unilamellar vesicles (LUVs) with lipid composition resembling the mitochondrial outer membrane were generated, encapsulating the fluorescent dye ANTS (8-aminonaphthalene-1,3,6-trisulfonic acid, disodium salt) and the quencher DPX (p-xylene-bis-pyridinium bromide). For measurement of Bfl-1-induced inhibition of BAX, Bfl-1, BAX, tBid activator and liposomes were combined. To test effects of covalently bound Bfl-1:NOXA on BAX activation, Bfl-1 and NOXA SAHB were preincubated as described, then used at the designated concentrations. ANTS release and dequenching due to DPX dissociation (F) was measured over a period of 120 min with an M1000 Infinite plate reader (Tecan) with excitation and emission wavelengths of 355 nm and 520 nm, respectively. Plates were read following liposome lysis with 1% Triton X-100 to determine maximal release (F100). Percent ANTS/DPX release was calculated as [(F−F0)(F10−F0)]×100.

Bfl-1:Warhead SAHB Conjugation Assay

10 µM Bfl-1 was reduced with DTT, then incubated with 3:1 molar ratio of warhead SAHB. Samples were then combined with loading dye, run on a 12% Bis-Tris SDS-PAGE, and stained with Coomassie. The same setup was used for all antiapoptotic proteins tested.

E. coli Lysate WB

E. coli lysate overexpressing 9×His-tagged Bfl-1 or GST-BCL-$X_L$ was reduced with 10 mM DTT for 30 min at RT, then combined with 50 µM biotinylated BIM warhead SAHB for 2 hr at RT. The samples were then run on a 4-12% Bis-Tris SDS-PAGE, transferred, and blotted with α-BCL2A1 (Abcam 125259) and α-BCL-$x_{S/L}$ (S-18) (Santa Cruz Biotechnology).

Example 5: Covalent Reaction Between Cysteines at the Binding Interface of NOXA BH3 and BFL-1

Anti-apoptotic BCL-2 family proteins block cell death by trapping the critical α-helical BH3 domains of pro-apoptotic members in a surface groove. Cancer cells hijack this survival mechanism by overexpressing a spectrum of anti-apoptotic members, mounting formidable apoptotic blockades that resist chemotherapeutic treatment. Drugging the BH3-binding pockets of anti-apoptotic proteins has become a highest priority goal.

Figures 10A, 10B:
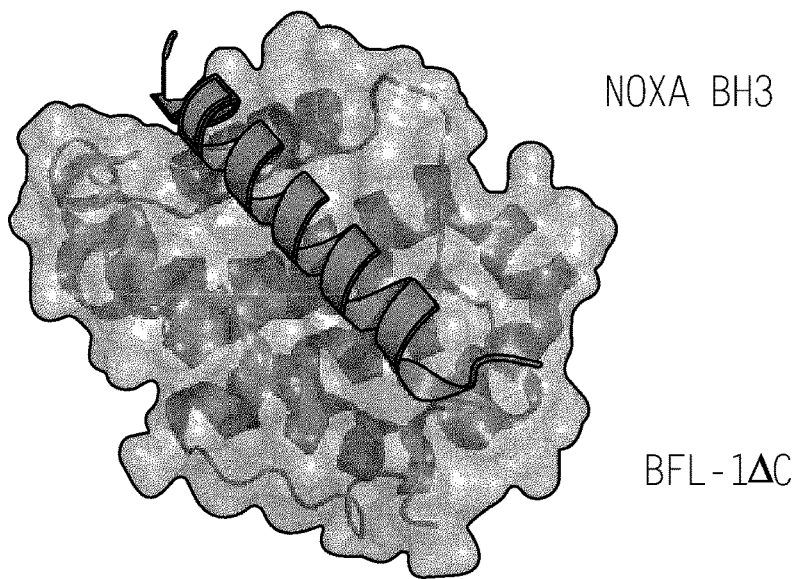
FIG. 10A: Structure of the NOXA BH3/BFL-1ΔC complex (PDB ID 3MQP) highlighting the juxtaposition between NOXA C25 and BFL-1 C55. The amino acid sequence for NOXA $SAHB_A$ shown in the figures is set forth in SEQ ID NO:9; and the amino acid sequence for NOXA $SAHB_A$ C25S shown in the figures is set forth in SEQ ID NO:13.
FIG. 10B: Dissociation constants for the binding interactions between BFL-1ΔC constructs and NOXA $SAHB_A$ peptides bearing the indicated native cysteines and cysteine-to-serine mutations. Binding experiments were performed in technical and biological duplicate.

The BH3-only protein NOXA exhibits natural, dual selectivity for interaction with anti-apoptotic MCL-1 and BFL-1, and therefore, its BH3 sequence was selected as a starting point for developing a BFL-1 inhibitor. In examining the crystal structure of human BFL-1ΔC in complex with NOXA BH3 (PDB ID 3MQP), we observed the proximity of NOXA C25 to BFL-1ΔC C55 at a distance of 3.9 Å, compatible with disulfide bond formation (FIG. 10A). As no other anti-apoptotic BCL-2 family member contains a cysteine in its BH3-binding pocket, we reasoned that C55-targeting by a stapled BH3 peptide could yield a BFL-1 inhibitor with selective covalent reactivity. To test our hypothesis, we first generated stapled NOXA BH3 peptides and recombinant BFL-1ΔC constructs bearing their native cysteines (NOXA: C25, BFL-1: C4. C19, C55) and a series of serine mutants (NOXA: C25S, BFL-1: C4S/C19S, C4S/C19S/C55S) for binding studies. For the stabilized alpha-helices of BCL-2 domains (SAHBs) modeled after NOXA BH3 (aa 19-43), we positioned the i, i+4 all-hydrocarbon staple at our classic "A" position (Walensky et al., Science, 305:1466-1470 (2004)) (substitution of R31 and K35) and derivatized the N-termini with PEG-biotin for biolayer interferometry analyses. We found that the peptide/protein pairs all demonstrated dissociation constants within a 46-165 nM range (FIG. 10B, FIGS. 11A-11F). Thus, serine mutagenesis, in and of itself, appeared to have no detrimental effect on binding affinity and, if anything, somewhat enhanced BFL-1 interaction by up to 3.5-fold.

Figure 10C:
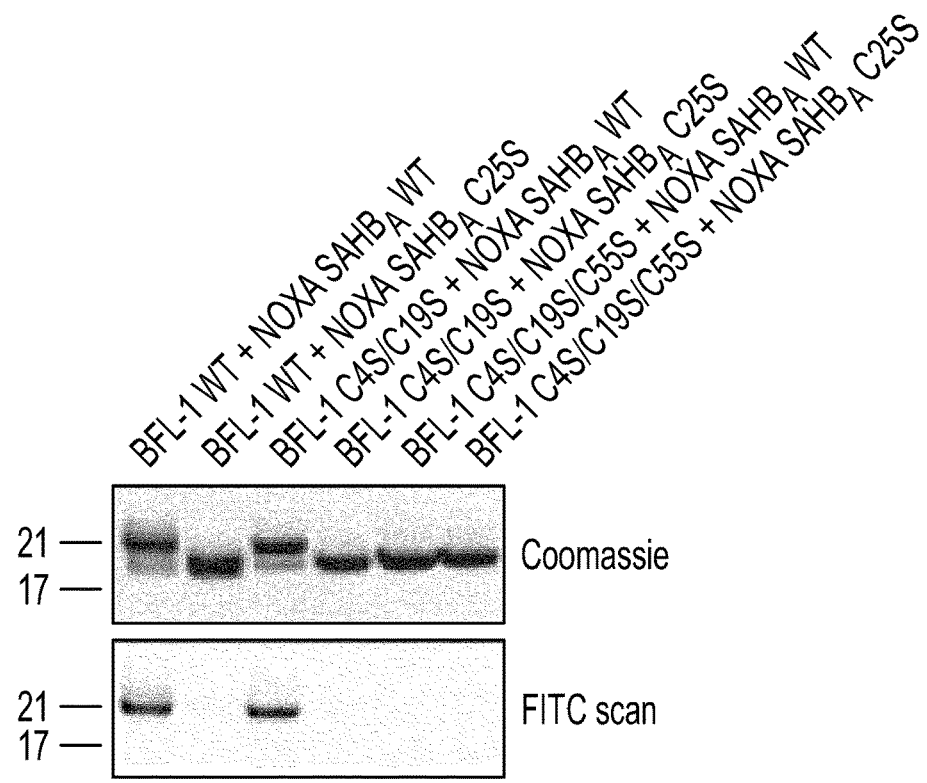
FIG. 10C: Exposure of BFL-1ΔC and FITC-NOXA $SAHB_A$ constructs to oxidizing conditions yielded a molecular weight shift only for peptide/protein pair that retain native NOXA C25 and BFL-1 C55, as detected by Coomassie staining (top). Disulfide bond formation between BFL-1ΔC bearing C55 and wild-type NOXA $SAHB_A$ was confirmed by FITC scan (bottom).
Figure 10D:
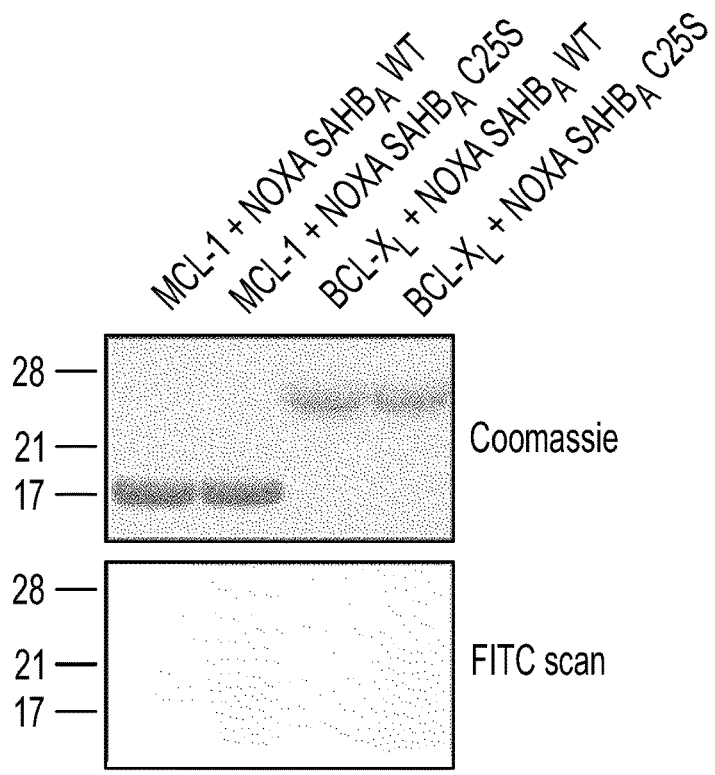
FIG. 10D: Incubation of NOXA SAHB peptides with alternate anti-apoptotic BCL-2 family proteins, such as MCL-1 ΔNΔC or BCL-$X_L$ΔC, under oxidizing conditions caused no molecular weight shift, as evaluated by Coomassie staining.
Figure 11A:
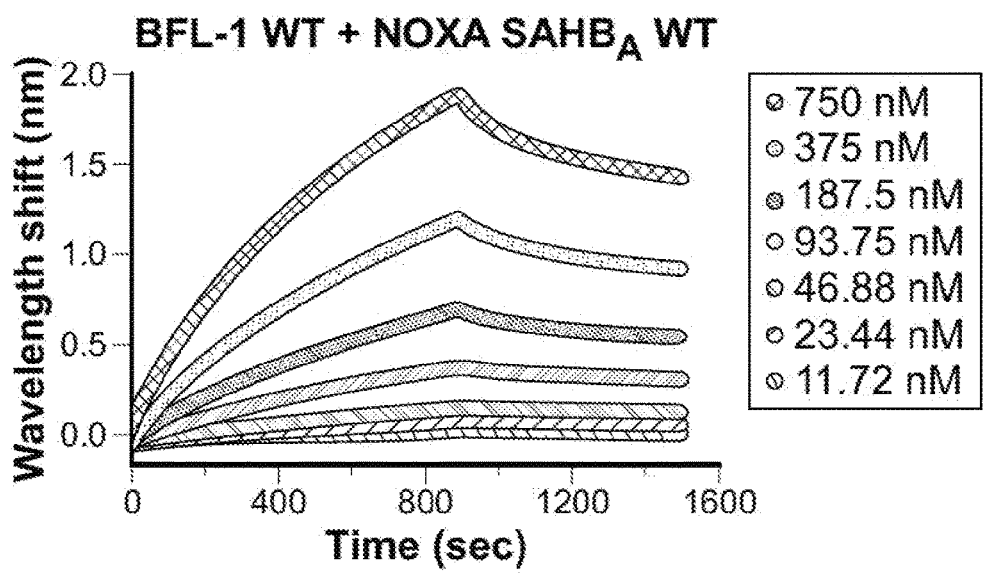
FIG. 11A: BFL-1 Binding Activity of NOXA SAHBs. The association and dissociation binding interactions between BFL-IAC constructs and biotin-PEG-NOXA $SAHB_A$ peptides bearing the indicated native cysteines and cysteine-to-serine mutations were measured by biolayer interferometry. Experiments were performed in technical and biological duplicate, with exemplary association and dissociation profiles shown.
Figure 11B:
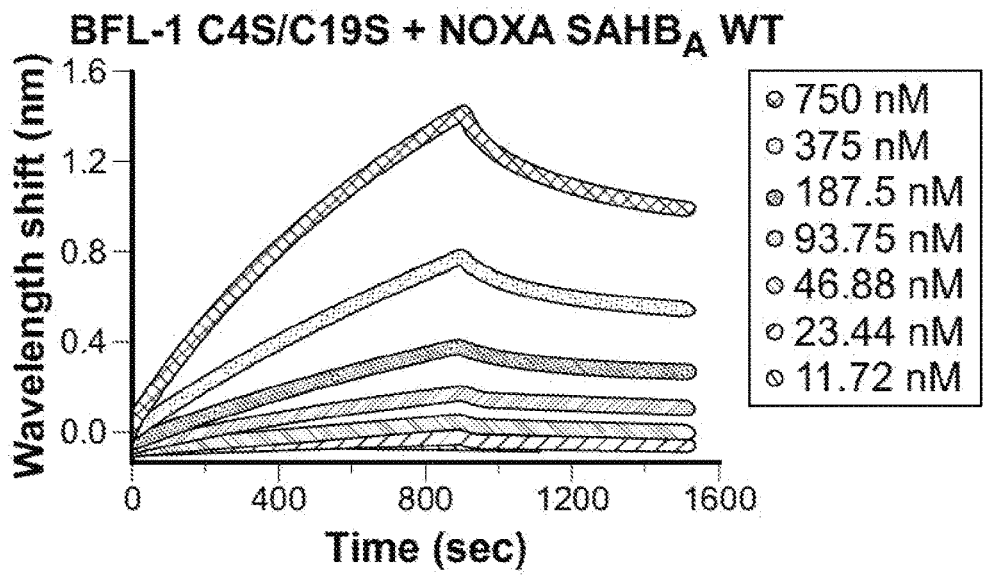
FIG. 11B: BFL-1 Binding Activity of NOXA SAHBs. The association and dissociation binding interactions between BFL-1ΔC constructs and biotin-PEG-NOXA SAHBA peptides bearing the indicated native cysteines and cysteine-to-serine mutations were measured by biolayer interferometry. Experiments were performed in technical and biological duplicate, with exemplary association and dissociation profiles shown.
Figure 11C:
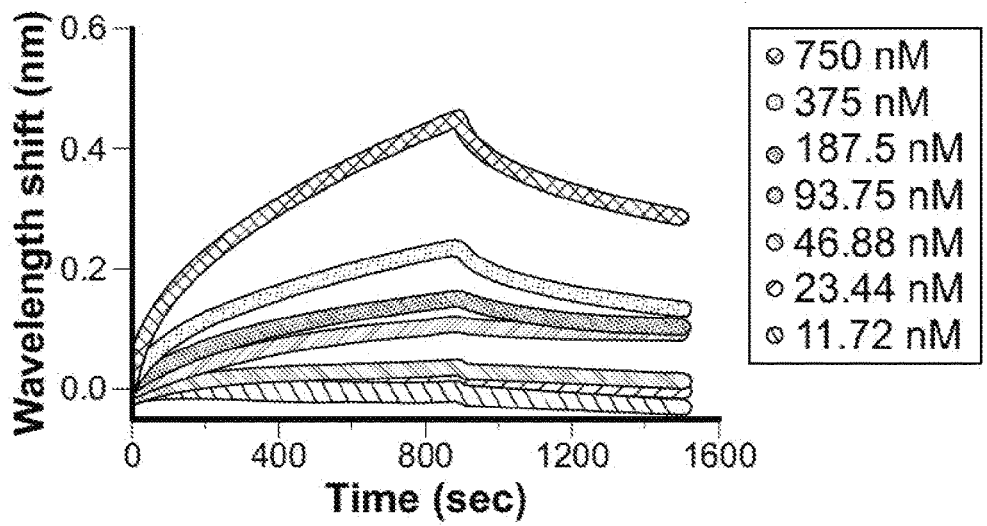
FIG. 11C: BFL-1 Binding Activity of NOXA SAHBs. The association and dissociation binding interactions between BFL-1ΔC constructs and biotin-PEG-NOXA SAHBA peptides bearing the indicated native cysteines and cysteine-to-serine mutations were measured by biolayer interferometry. Experiments were performed in technical and biological duplicate, with exemplary association and dissociation profiles shown.
Figure 11D:
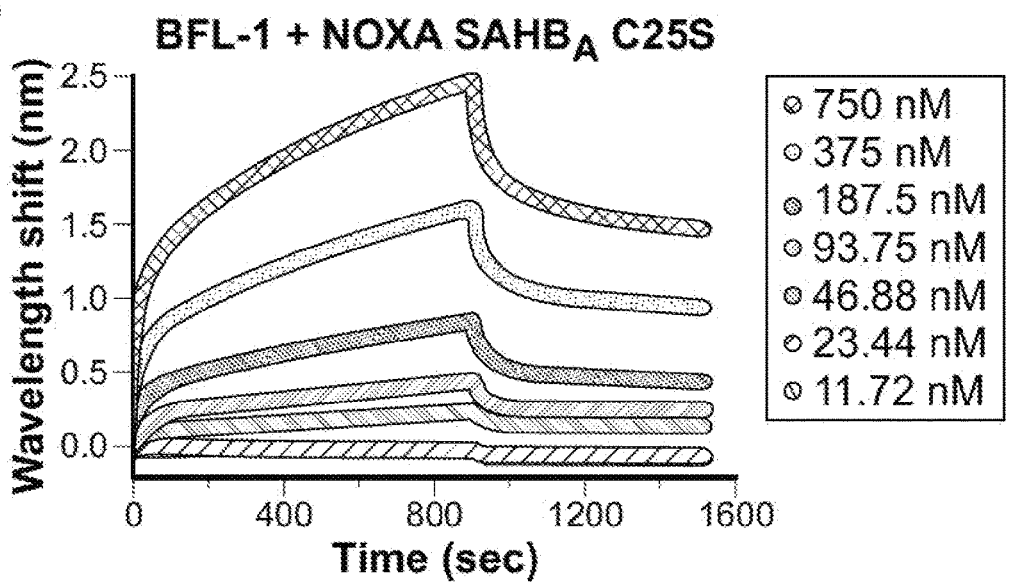
FIG. 11D: BFL-1 Binding Activity of NOXA SAHBs. The association and dissociation binding interactions between BFL-1ΔC constructs and biotin-PEG-NOXA SAHBA peptides bearing the indicated native cysteines and cysteine-to-serine mutations were measured by biolayer interferometry. Experiments were performed in technical and biological duplicate, with exemplary association and dissociation profiles shown.
Figure 11E:
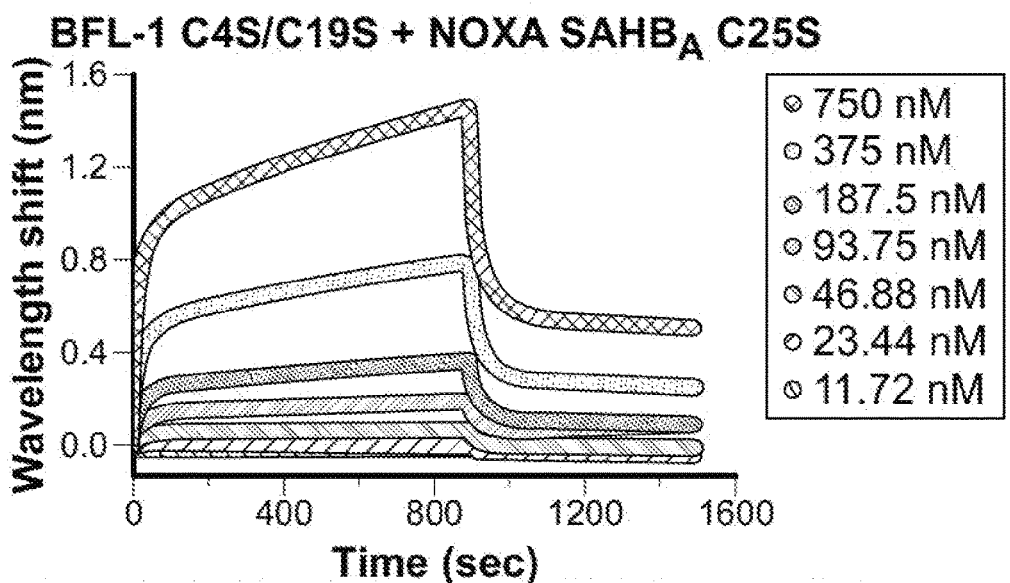
FIG. 11E: BFL-1 Binding Activity of NOXA SAHBs. The association and dissociation binding interactions between BFL-1ΔC constructs and biotin-PEG-NOXA SAHBA peptides bearing the indicated native cysteines and cysteine-to-serine mutations were measured by biolayer interferometry. Experiments were performed in technical and biological duplicate, with exemplary association and dissociation profiles shown.
Figure 11F:
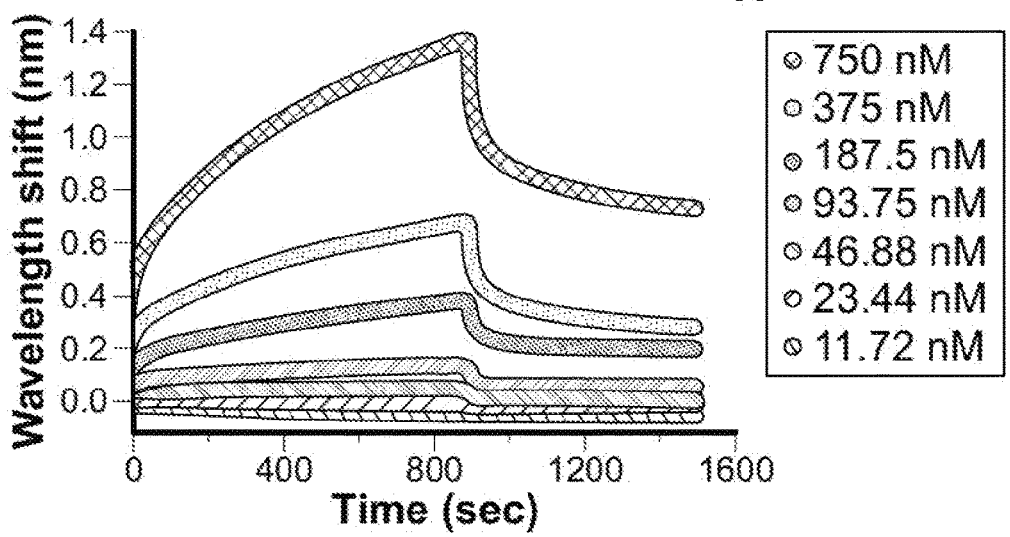
FIG. 11F: BFL-1 Binding Activity of NOXA SAHBs. The association and dissociation binding interactions between BFL-IAC constructs and biotin-PEG-NOXA SAHBA peptides bearing the indicated native cysteines and cysteine-to-serine mutations were measured by biolayer interferometry. Experiments were performed in technical and biological duplicate, with exemplary association and dissociation profiles shown.

We then sought to determine if disulfide bond formation between NOXA C25 and BFL-1ΔC C55 was biochemically feasible. Indeed, upon DTT (10 mM) reduction followed by GSSG oxidation (12 mM), we observed a shift in the molecular weight of wild-type BFL-IAC when incubated with NOXA SAHB$_A$ but not its C25S mutant, as assessed by gel electrophoresis under denaturing and nonreducing conditions and Coomassie staining (FIG. 10C, top). Our use of FITC-NOXA SAHB peptides provided confirmation that the BFL-1 protein was labeled by the wild-type but not C25S mutant peptide, as detected by FITC scan (FIG. 10C, bottom). We likewise determined that NOXA C25 formed a disulfide bond with BFL-1ΔC C55, as demonstrated both by the molecular weight shift (Coomassie stain) and FITC-labeling of the BFL-IAC C4S/C19S construct (in which only C55 is present), but no adduct with the BFL-1ΔC C4S/C19S/C55S construct that lacks C55 (FIG. 10Q. As a measure of cysteine specificity, we repeated the experiment using MCL-1ΔNΔC and BCL-$X_L$ΔC, both of which contain cysteines (MCL-1 C286, BCL-$X_L$ C151), and observed no molecular weight shift or FITC labeling upon incubation with NOXA SAHB under oxidizing conditions (FIG. 10D).

These data show that the juxtaposed cysteines at the NOXA BH3/BFL-1 interface form a disulfide bond in a selective fashion.

Figure 12A:
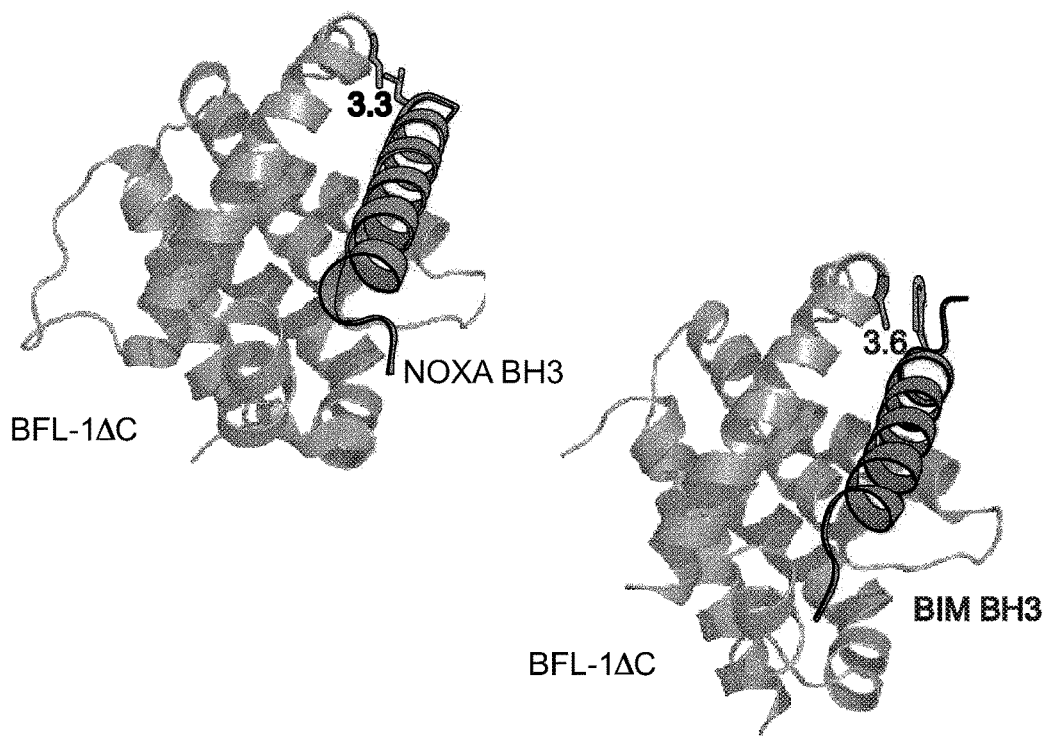
FIG. 12A: The structures of the NOXA BH3/BFL-1ΔC (left, PDB ID 3MQP) and BIM BH3/BFL-1ΔC (right, PDB ID 2VM6) complexes demonstrate the proximity of discrete BH3 residues to C55 for replacement with electrophilic warheads. The amino acid sequence for NOXA $SAHB_A$-WH shown in the figures is set forth in SEQ ID NO:24: the amino acid sequence for BIM $SAHB_A$-WH shown in the figures is set forth in SEQ ID NO:30.
Figure 12B:
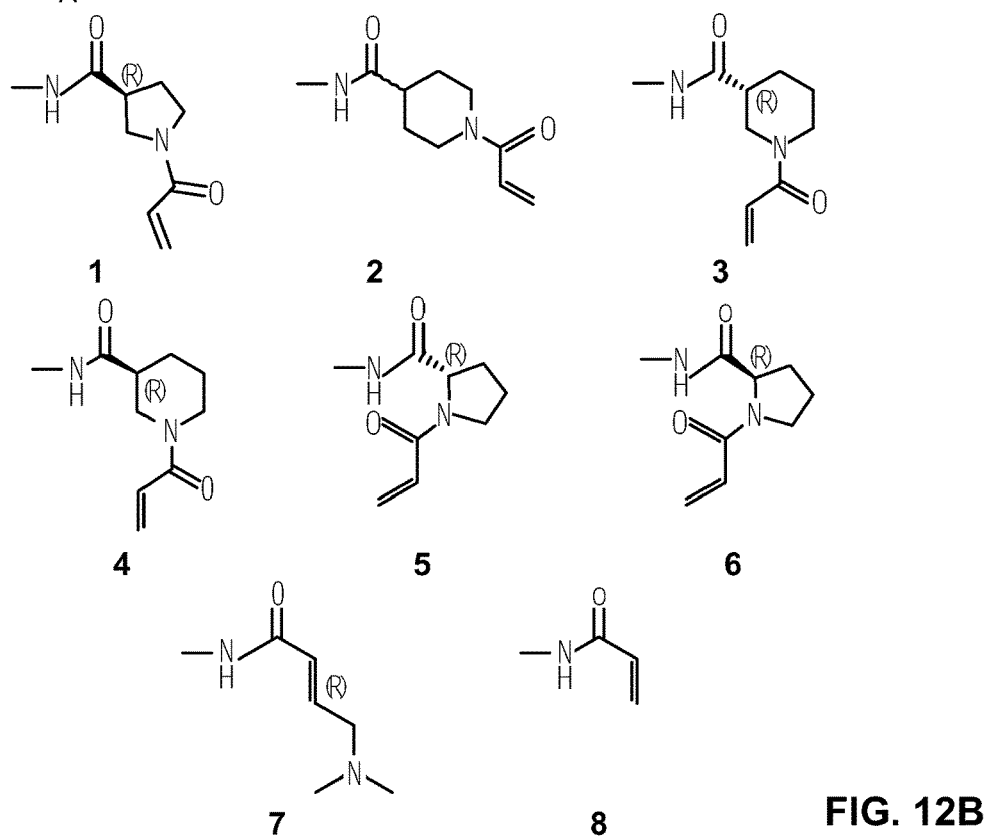
FIG. 12B: Chemical structures of the reactive acrylamide moieties installed at the N-termini of NOXA and BIM SAHB peptides.

Example 6: Selective BFL-1 Reactivity of Stapled BH3 Peptides Bearing Electrophilic Warheads The capacity of NOXA SAHB$_A$ and BFL-1ΔC to engage through disulfide bond formation suggested a novel opportunity to develop stapled peptides for covalent targeting of cysteines localized to key regulatory surfaces, such as the BH3-binding pocket of BFL-1. Because relying on intracellular disulfide bond formation as a basis for protein target inhibition is not a tractable pharmacologic strategy, we instead examined possible sites for insertion of non-natural amino acids bearing reactive acrylamide moieties, and identified NOXA L21 as having even closer proximity to BFL-1 C55 than NOXA C25 (3.3 vs. 3.9 Å, respectively) based on the crystal structure of the NOXA BH3/BFL-1 complex (PDB ID 3MQP) (FIG. 12A, top). In the case of the more promiscuous BIM BH3 sequence, W147 manifests optimal adjacency to BFL-1 C55 (3.6 Å) based on the crystal structure of the BIM BH3/BFL-1 complex (PDB 1D 2VM6) (FIG. 12A, bottom). Thus, we capped NOXA SAHB$_A$ and BIM SAHB$_A$ at positions L21 and W147, respectively, with a series of non-natural amino acids bearing distinct acrylamide species (FIG. 12B).

Figure 12C:
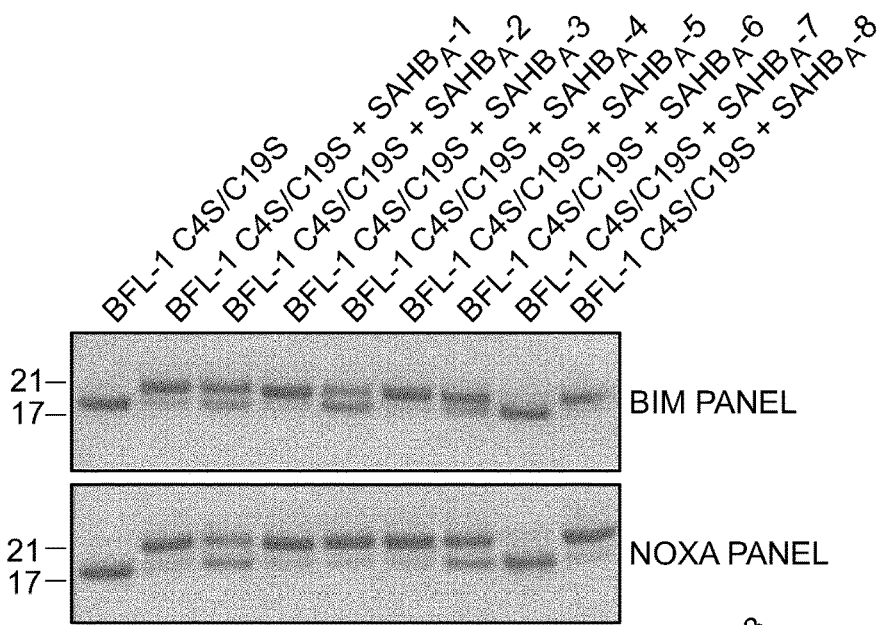
FIG. 12C: Reactivity of BIM and NOXA SAHBs bearing warheads 1-8 with BFL-1ΔC C4S/C19S, which only retains the native C55.

In comparing the reactivity of the electrophilic "warhead"-bearing NOXA (aa 21-43) and BIM SAHB$_A$ (aa 147-166) panels, we observed efficient conversion of BFL-1 to the heavier, conjugated adduct for SAHB$_S$ bearing warheads 1, 3, 5, and 8, as assessed by reducing and denaturing gel electrophoresis and Coomassie staining (FIG. 12C). We advanced NOXA and BIM SAHBs bearing one of the most effective warheads, D-nipecotic acid (3 of FIG. 12B), to specificity testing.

Figure 12D:
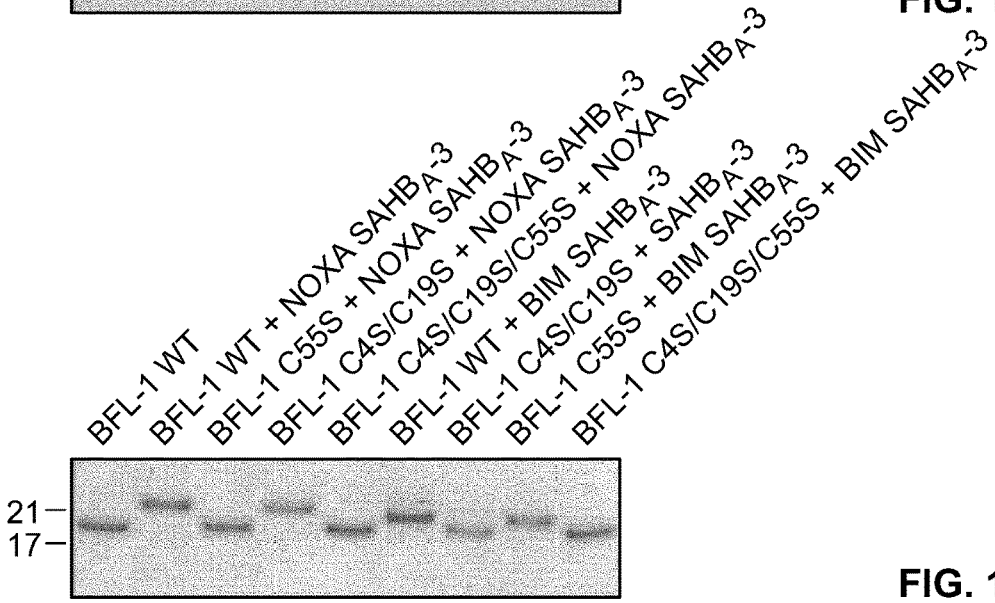
FIG. 12D: BIM and NOXA $SAHB_A$-3 peptides selectively reacted with BFL-1ΔC protein bearing C55.

First, we tested the selectivity of NOXA SAHB$_A$-3 and BIM SAHB$_A$-3 for BFL-1 C55. Upon incubation of SAHB$_A$-3 compounds with BFL-1 constructs bearing all native cysteines (BFL-1 WT), C55-only (BFL-1 C4S/C19S), C4 and C19-only (BFL-1 C55S), or no cysteines (BFL-1 C4S/C19S/C55S), we observed exclusive reactivity with the WT and BFL-1 C4S/C19S constructs, underscoring the cysteine-selectivity of NOXA SAHB$_A$-3 and BIM SAHB$_A$-3 for C55 of the BH3-binding pocket (FIG. 12D).

Figure 12E:
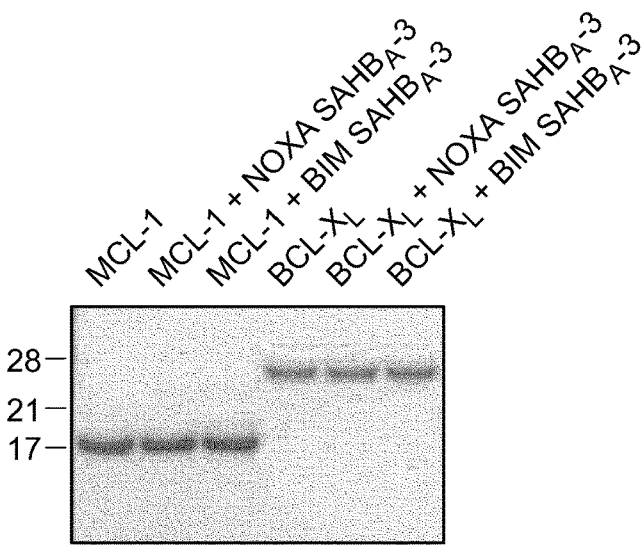
FIG. 12E: BIM and NOXA SAHBA-3 peptides did not react with MCL-1ΔNΔC or BCL-XLΔC, despite the presence of cysteines in these anti-apoptotic targets.

As a further measure of compound specificity, we repeated the experiment using MCL-1ΔNΔC and BCL-X$_L$ΔC and observed no nonspecific reactivity, despite the presence of cysteines in these anti-apoptotic BCL-2 family proteins (FIG. 12E).

Thus, we found that installing a cysteine-reactive warhead in stapled NOXA and BIM BH3 peptides results in efficient and selective covalent-targeting of the BFL-1 BH3-binding groove.

Figure 13A:
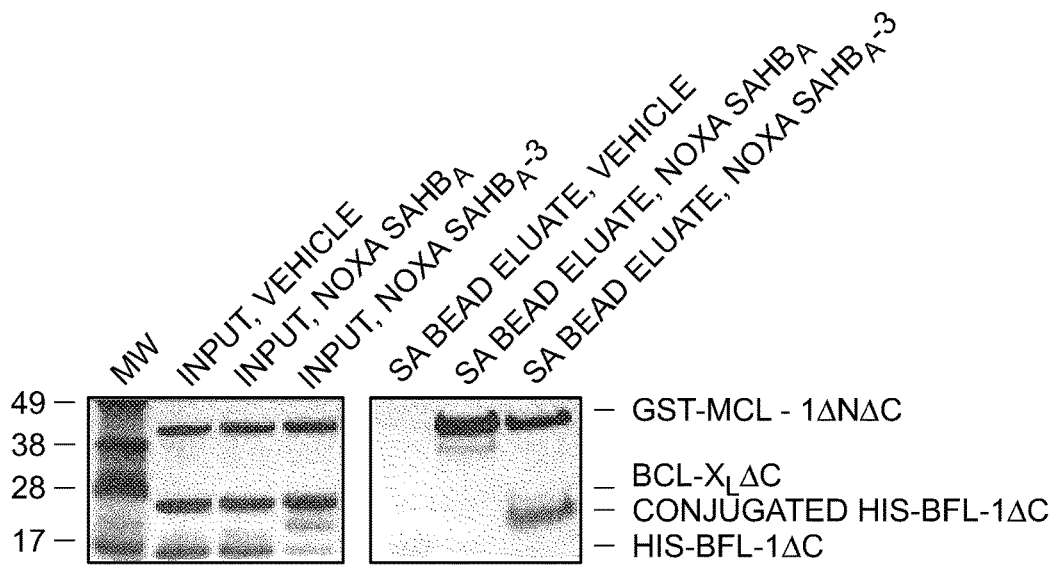
FIG. 13A: Incorporation of an acrylamide moiety into NOXA and BIM SAHBs provided a competitive advantage for BFL-1 targeting, as demonstrated by SA pull-down of a 1:1:1:1 mixture (1 μM each) of biotinylated NOXA SAHBs with recombinant His-BFL-1ΔC, BCL-$X_L$ΔC (tagless), and GST-MCL-1ΔNΔC.
Figure 13B:
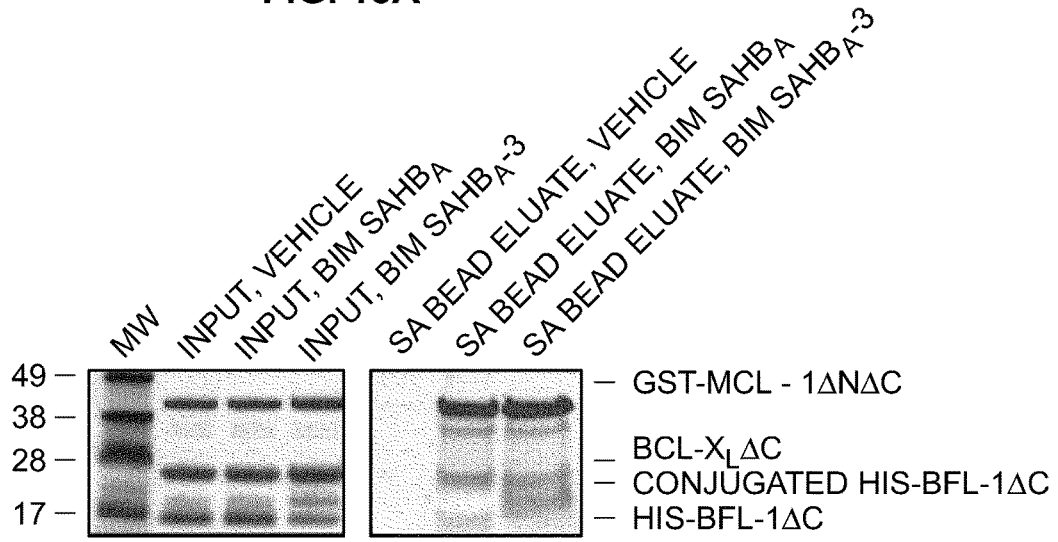
FIG. 13B: Incorporation of an acrylamide moiety into NOXA and BIM SAHBs provided a competitive advantage for BFL-1 targeting, as demonstrated by SA pull-down of a 1:1:1:1 mixture (1 μM each) of biotinylated BIM SAHBs with recombinant His-BFL-IAC, BCL-$X_L$ΔC (tagless), and GST-MCL-1ΔNΔC.

We next explored how conversion of NOXA and BIM SAHBs to BFL-1 C55-reactive agents influenced the balance between noncovalent and covalent SAHB interactions in the context of an anti-apoptotic protein mixture. First, we generated recombinant MCL-1 ΔNΔC, BCL-X$_L$ΔC and BFL-1ΔC proteins with differential N-terminal tags (GST, tagless, and His, respectively) so that each could be readily identified upon gel electrophoresis and silver stain (FIG. 13A-B). Upon incubation of the anti-apoptotic mixture with biotinylated NOXA SAHBA or NOXA SAHB$_A$-3 (1:1:1:1 for each component), we only see a shift in the molecular weight of BFL-1ΔC, corresponding to the selective covalent reaction (FIG. 13A, left). Streptavidin (SA) pull-down revealed prominent non-covalent capture of MCL-ΔNΔC by NOXA SAHB$_A$, but a notable shift in the interaction propensity of NOXA SAHB$_A$-3, with relatively less MCL-1ΔNΔC and notably more BFL-1ΔC engagement as a result of covalent BFL-1ΔC conjugation (FIG. 13A, right). Consistent with the broader anti-apoptotic binding spectrum of BIM BH3, the corresponding BIM SAHBs engaged BCL-X$_L$ΔC in addition to MCL-1ΔNΔC and BFL-1ΔC, but an increased BFL-IAC targeting propensity was again observed for BIM SAHB$_A$-3 relative to BIM SAHB$_A$ as a consequence of covalent conjugation (FIG. 13B).

Thus, the capacity for selective covalent reaction with BFL-IAC can shift the competitive balance of SAHB interactions toward BFL-1.

Example 7: Targeted Blockade of BFL-1 in Liposomes, Lysates, and Cells

Figure 13C:
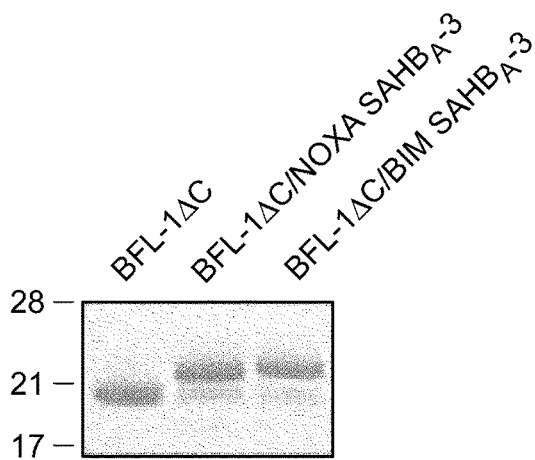
FIG. 13C: Coomassie stain of recombinant BFL-1ΔC and its NOXA SAHBA-3 and BIM SAHBA-3 conjugates employed in liposomal release assays.
Figure 13D:
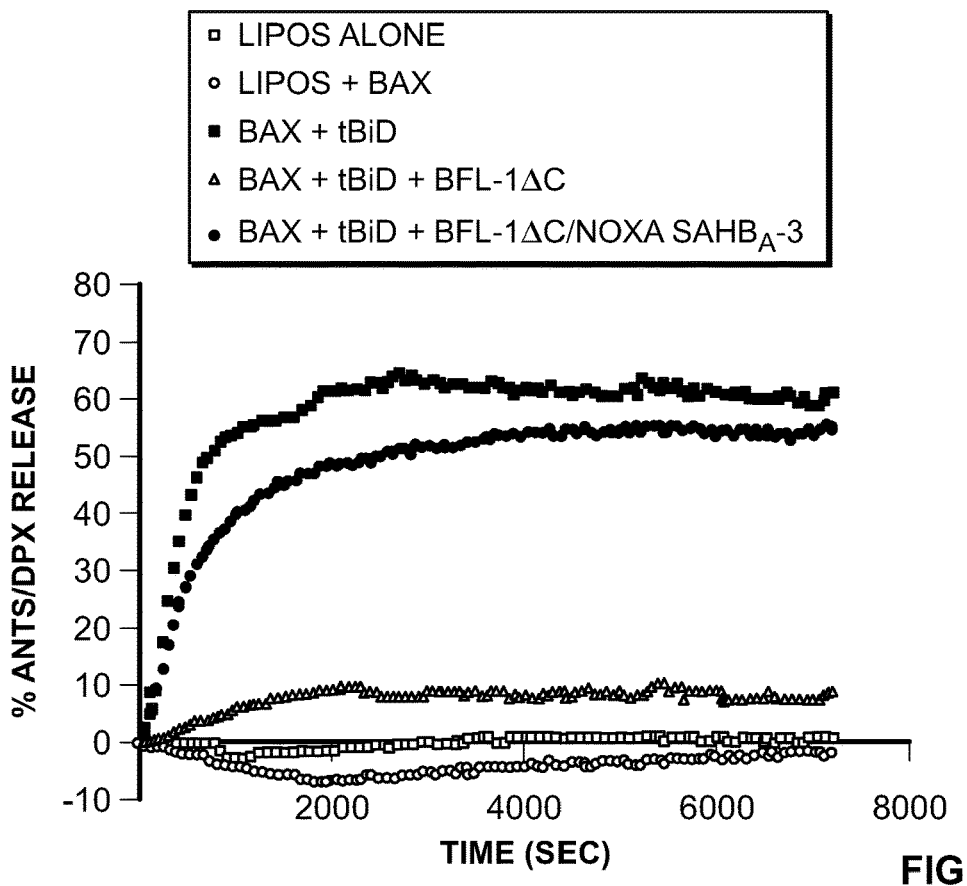
FIG. 13D: BH3-only protein tBID directly activated BAX-mediated liposomal poration, as monitored by ANTS/DPX release. Whereas BFL-1ΔC completely blocked tBID-triggered BAX poration, covalent engagement of BFL-1ΔC by NOXA SAHB$_A$-3 effectively inhibited the functional activity of BFL-1ΔC. Liposomal experiments were performed in triplicate with exemplary release profiles shown.
Figure 13E:
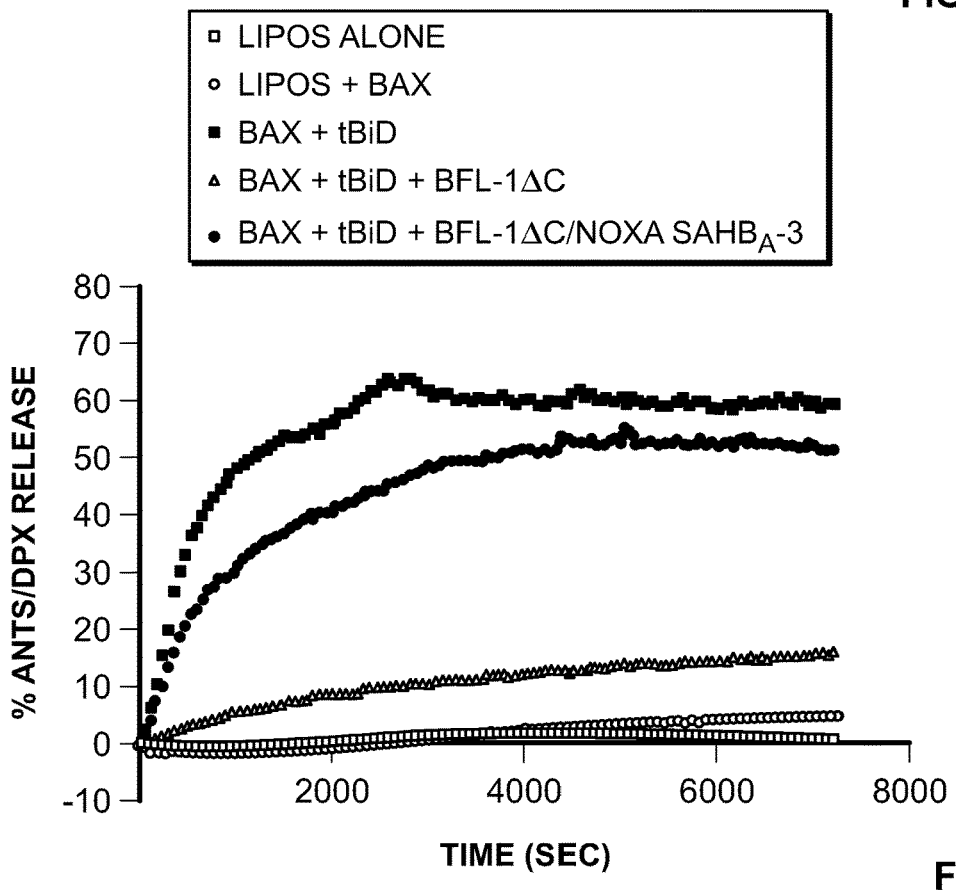
FIG. 13E: BH3-only protein tBID directly activated BAX-mediated liposomal poration, as monitored by ANTS/DPX release. Whereas BFL-1ΔC completely blocked tBD-triggered BAX poration, covalent engagement of BFL-1ΔC by BIM SAHB$_A$-3 effectively inhibited the functional activity of BFL-IAC. Liposomal experiments were performed in triplicate with exemplary release profiles shown.

To determine the functional consequences of covalent targeting of the BFL-1 BH3-binding pocket, we performed liposomal release assays designed to monitor the influence of BFL-1 on direct BAX activation. We generated ANTS/DPX-encapsulated large unilamellar vesicles (LUV) and monitored liposomal release of fluorophore upon BAX-mediated membrane poration. Whereas BAX alone had no effect on the liposomes, the addition of direct activator BH3-only protein tBID, triggered time-responsive, BAX-mediated release, a process that was suppressed by BFL-1ΔC (FIG. 13C-E). However, upon addition of either NOXA SAHB$_A$-3 or BIM SAHB$_A$-3 conjugated BFL-IAC (FIG. 13C), the inhibitory function of BFL-1 was lost (FIGS. 13D-E). These data highlight that covalently "plugging" the BH3-binding pocket of BFL-1 with NOXA SAHB$_A$-3 or BIM SAHB$_A$-3 irreversibly neutralizes its anti-apoptotic function.

Figure 14A:
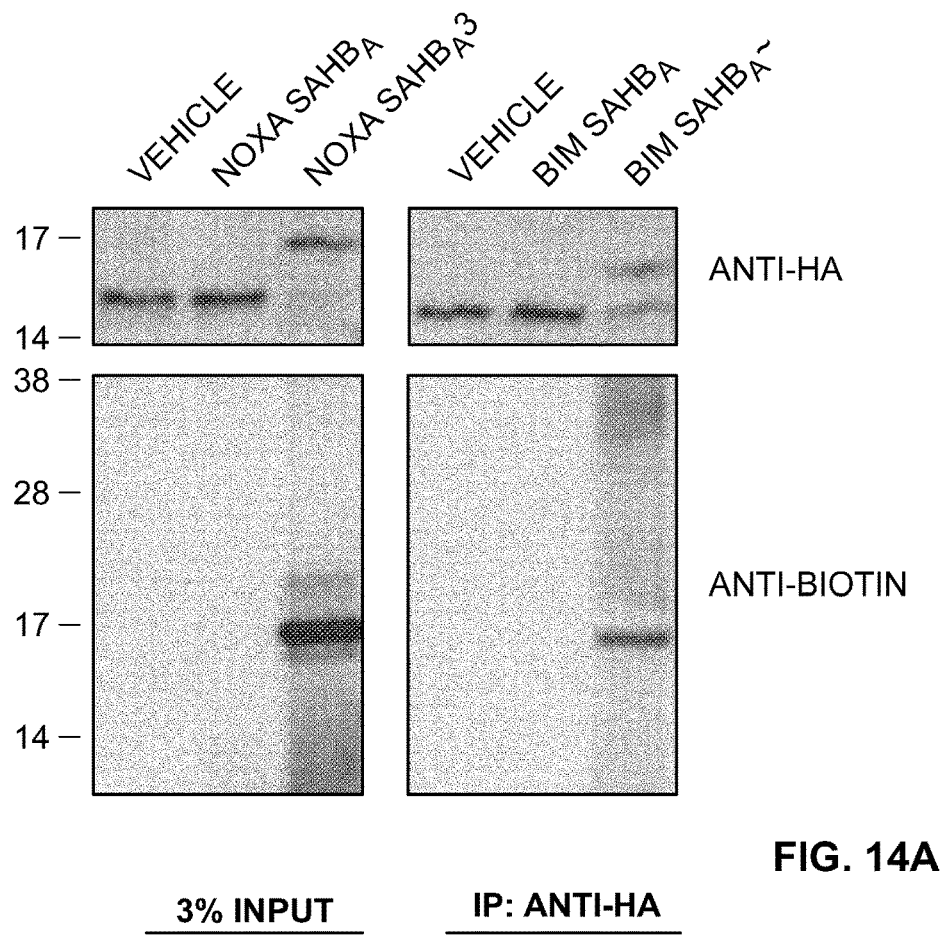
FIG. 14A: Biotinylated NOXA and BIM SAHB$_A$-3 peptides crosslinked to HA-BFL-1ΔC C4S/C19S in lysates from transfected 293T lysates, as evidenced by the shift in molecular weight of BFL-IAC observed upon anti-HA western analysis. Anti-biotin blotting confirmed the selective incorporation of biotin into the HA-BFL-1ΔC band, with little to no crossreactivity with other proteins in the cellular lysate.
Figure 14B:
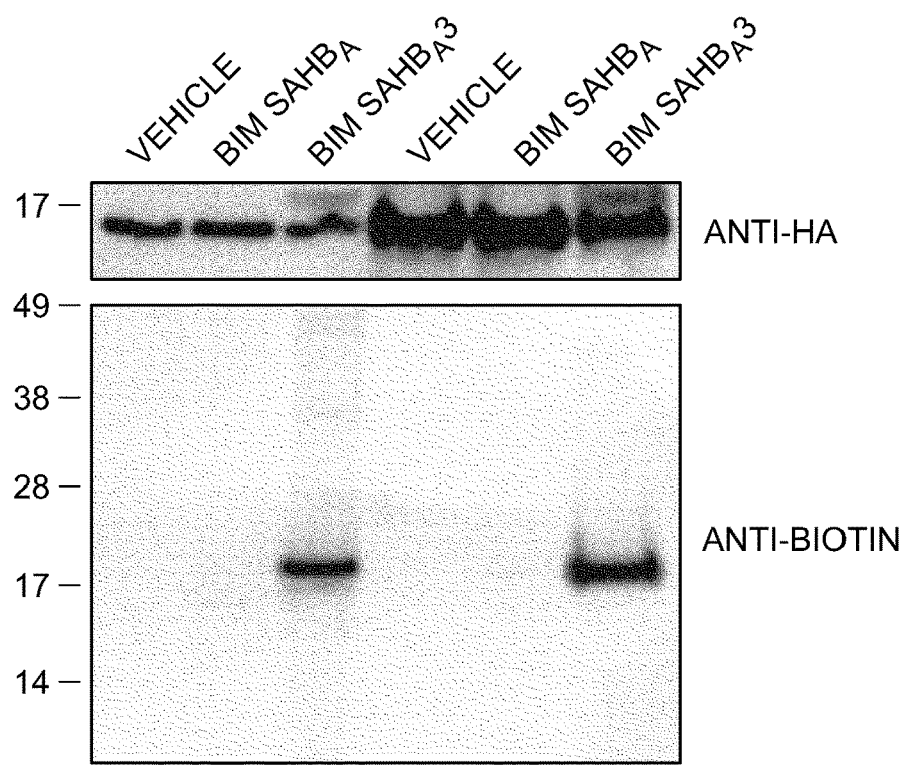
FIG. 14B: Treatment of transfected 293T cells with biotinylated BIM SAHB$_A$-3 followed by cellular lysis, HA immunoprecipitation, and biotin western analysis demonstrated the capacity of a warhead-bearing BIM SAHB to gain intracellular access and covalently target expressed HA-BFL-IAC C4S/C19S containing the native C55.

We next sought to test whether our covalent stapled peptide inhibitors could selectively react with BFL-1 in more complex protein mixtures. To specifically track C55 derivatization, we transiently expressed HA-BFL-1ΔC C4S/C19S in 293T cells and, after 24 hours, harvested cell lysates for crosslinking analyses with C-terminal Lys-biotin derivatized SAHB constructs that either did or did not contain the electrophilic warhead. Anti-HA western analyses revealed prominent molecular weight shifts only for warhead-bearing SAHBs, consistent with covalent incorporation of both NOXA SAHB$_A$-3 and BIM SAHB$_A$-3 into the BFL-1 protein at C55 (FIG. 14A, top). To confirm that the observed molecular weight shifts reflected NOXA SAHB$_A$-3 and BIM SAHB$_A$-3 incorporation, we performed biotin western analyses. We found that the shifted HA-BFL-1 bands were indeed biotin-immunoreactive and, importantly, there was little to no non-specific reactivity with other electrophoresed proteins from the 293T lysates (FIG. 14A, bottom).

Figure 15A:
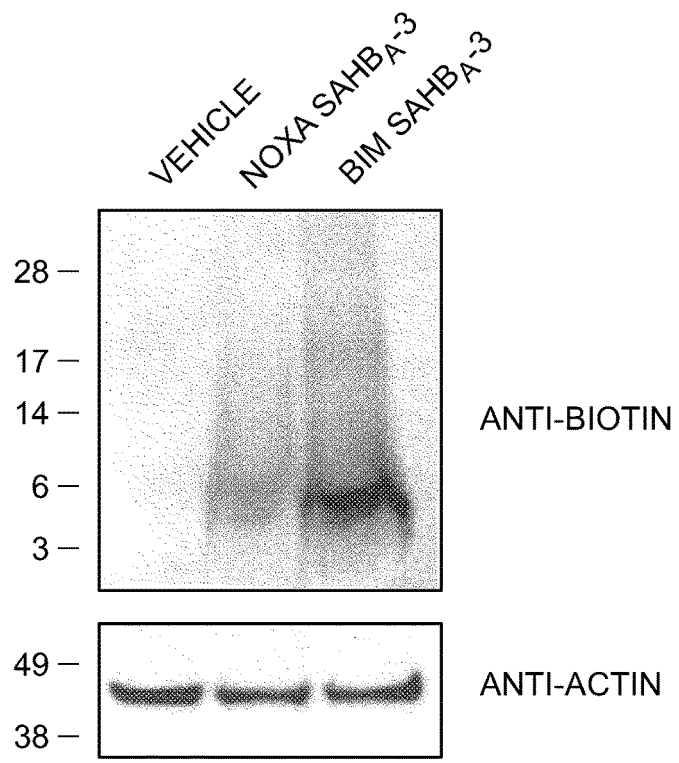
FIG. 15A: 293T cells were treated with biotinylated NOXA SAHB$_A$-3 or BIM SAHB$_A$-3 (20 μM) for 24 h followed by washing, trypsinizing, rewashing and lysing the cells. Comparative stapled peptide uptake was assessed by electrophoresis of the cellular lysates and biotin western analysis.
Figure 15B:
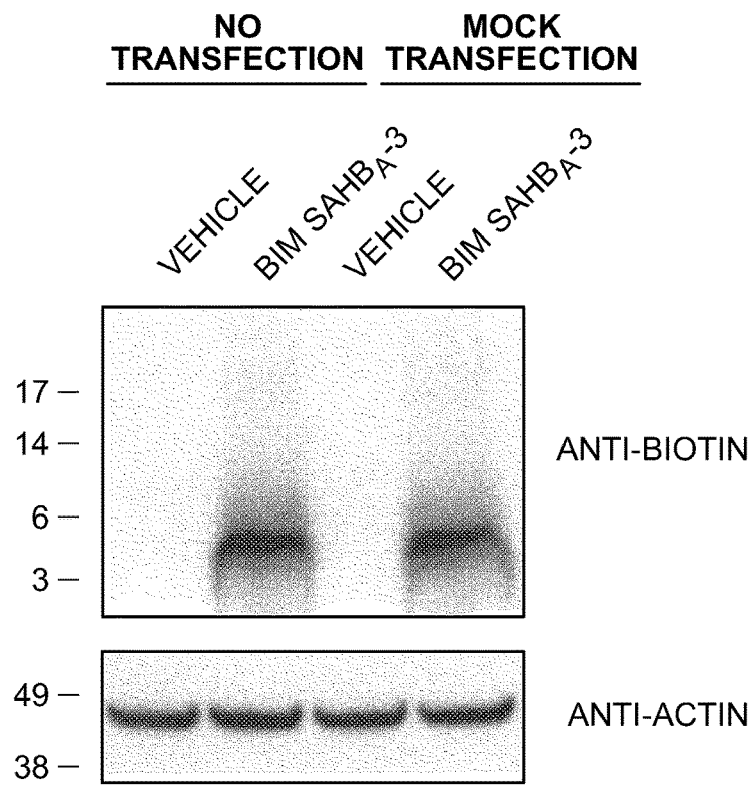
FIG. 15B: 293T cells were either mock transfected or not, and then 24 h later treated with biotinylated BIM SAHB$_A$-3 (20 μM) for an additional 4 h, and then processed as above for comparative biotin blotting of cellular lysates.

To advance our strategy to cellular testing, we first evaluated the cellular uptake potential of our biotinylated NOXA SAHB$_A$-3 and BIM SAHB$_A$-3 constructs. We incubated 293T cells with the compounds at 20 μM dosing for 24 hours, trypsinized and washed the cells to remove any adherent peptide, and then generated lysates for anti-biotin western analyses. We proceeded with BIM SAHB$_A$-3 for cellular testing (FIG. 15A). We further confirmed that the transfection conditions themselves did not independently influence the cellular uptake of BIM SAHB$_A$-3 (FIG. 15B). 293T cells transiently overexpressing HA-BFL-1ΔC C4S/C19S were treated with biotinylated BIM SAHB$_A$ (aa 147-166) or BIM SAHB$_A$-3 (20 μM, 6 h) and then lysates, generated as above, were subjected to anti-HA immunoprecipitation. Biotin western analysis of the input revealed a single, prominent protein band only in the denatured and reduced electrophoresed lysate of cells treated with BIM SAHB$_A$-3 (FIG. 15B, left). Subjecting the immunoprecipitate to anti-HA western analysis revealed the BFL-1 doublet, and biotin western analysis confirmed that the upper band indeed corresponded to biotinylated HA-BFL-1 (FIG. 15B, right).

Figure 14C:
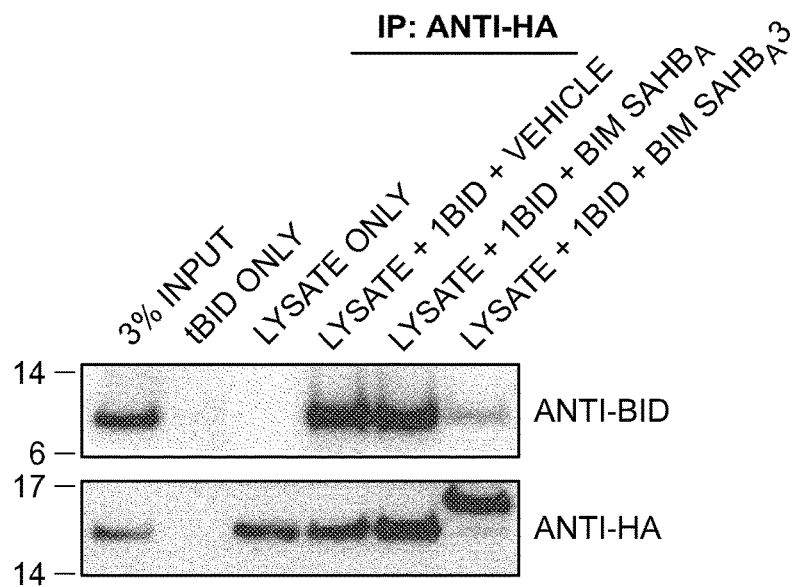
FIG. 14C: BIM SAHB$_A$-3, but not BIM SAHB$_A$, effectively competed with tBID for HA-BFL-1ΔC C4S/C19S interaction in 293T lysates, achieving robust covalent conjugation, as measured by the indicated immunoprecipitation and western analyses.
Figure 14D:
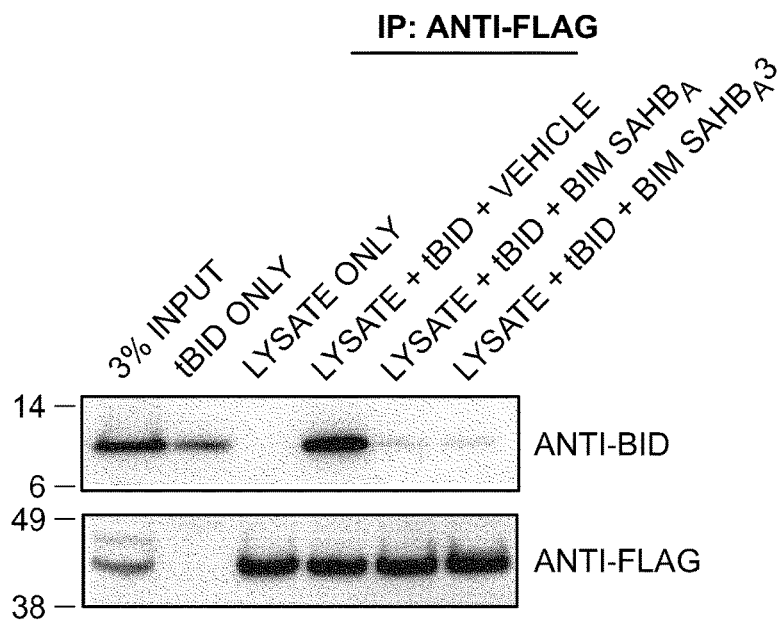
FIG. 14D: In the context of exclusive non-covalent FLAG-MCL-1 interaction, the compounds—BIM SAHB$_A$-3 and BIM SAHB$_A$-were equally effective at competing with tBID, as measured by the indicated immunoprecipitation and western analyses.

Having documented the feasibility of specific labeling of intracellular BFL-1 upon treating cells with biotinylated BIM SAHB$_A$-3, we then examined the relative influence of covalent vs. non-covalent engagement on the capacity of BIM SAHBs to disrupt BFL-1 complexes. For this experiment, we added tBID to the lysates from 293T cells transiently transfected with HA-BFL-1ΔC C4/C19S, incubated the mixture with biotinylated BIM SAHB$_A$ or BIM SAHB$_A$-3, performed anti-HA immunoprecipitation and blotted for HA, tBID, and biotin. Strikingly, BIM SAHB$_A$ was incapable of competing with tBID for HA-BFL-1 binding, whereas the warhead-bearing BIM SAHB$_A$-3 construct covalently trapped HA-BFL-1, as exemplified by complete protein conversion to the higher molecular weight species and near total inhibition of tBID co-immunoprecipitation (FIG. 14C). When the experiment was repeated using lysates from 293T cells transiently expressing FLAG-MCL-1, which bears no cysteine in its BH3-binding pocket, both BIM SAHB$_A$ peptides were equally effective as non-covalent disruptors of tBID/FLAG-MCL-1 co-immunoprecipitation (FIG. 14D). Thus, by installing the warhead and enabling stapled peptide covalent reaction, the BFL-1 targeting efficacy of BIM SAHB$_A$ can be selectively enhanced.

Figure 14E:
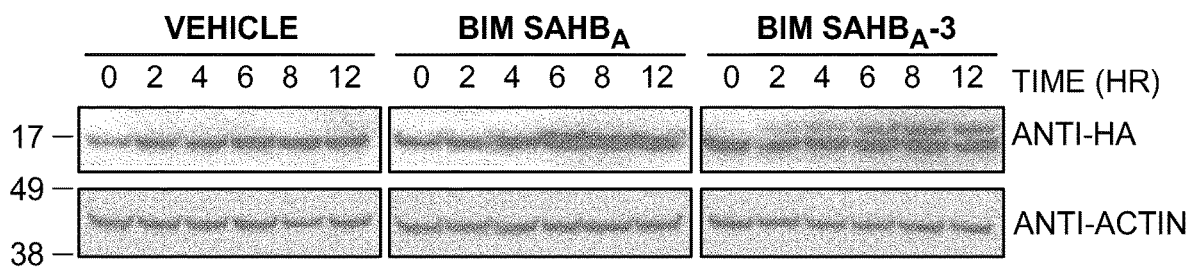
FIG. 14E: Covalent modification of HA-BFL-1ΔC C4S/C19S by cellular treatment with BIM SAHBA-3, but not the corresponding construct lacking the acrylamide-based warhead. Crosslinked BFI-1ΔC was observed by 2 hours and levels continued to increase in a time-dependent fashion throughout the 12 hour treatment period, as monitored by HA western analysis.

Finally, we turned to the corresponding non-biotinylated BIM SAHB$_A$ constructs to probe the kinetics and efficiency of covalent targeting of BFL-1 in cells. Comparing BIM SAHB$_A$- and BIM SAHB$_A$-3-treated 293T cells transiently overexpressing HA-BFL-1ΔC C4S/C19S, we observed a discrete molecular weight shift in BFL-1 by anti-HA western analysis within 2 hours of BIM SAHB$_A$-3 exposure, with a progressive increase in the crosslinked species over the 12 hour evaluation period (FIG. 14E).

Taken together, these data highlight the capacity of a stapled peptide bearing an electrophilic warhead to covalently target BFL-1 in treated lysates and cells.

Example 8: Preferential Activation of Apoptosis by a Cysteine-Reactive BIM SAHBA in BFL-1-Expressing Melanoma BFL-1 has recently been implicated as a lineage-specific driver of human melanoma, with gene amplification observed in ~30% of cases and BFL-1 overexpression mediated by the MITF transcription factor, a melanoma oncogene (Haq et al., *Proc Natl Acad Sci USA* 110:4321-4326 (2013)). Thus, to explore the functional impact of covalent BFL-1 targeting in cancer cells driven by BFL-1 expression, we tested the comparative effect of BIM SAHB$_A$-3 with a noncovalent stapled peptide modulator of BCL-2 family proteins, BIM SAHB$_A$ in A375P melanoma cells. We first confirmed that BIM SAHB$_{A1}$ and BIM SAHB$_A$-3 have equivalent cellular uptake, as quantified by ImageXpress Micro (IXM) high content epifluorescence microscopy of treated A375P cells and mouse embryonic fibroblasts (MEFs), which we have used previously to benchmark the comparative cell penetrance of FITC-labeled stapled peptides (Bird et al., Biophysical determinants for cellular uptake of hydrocarbon-stapled peptide helices. *Nat Chem Biol* in press. 2016) (data not shown). The mechanism of uptake for BIM SAHBs is consistent with micropinocytosis and evidenced by the epifluorescence microscopy pattern of treated A375P and MEF cells at 4 hours (data not shown).

Figure 16A:
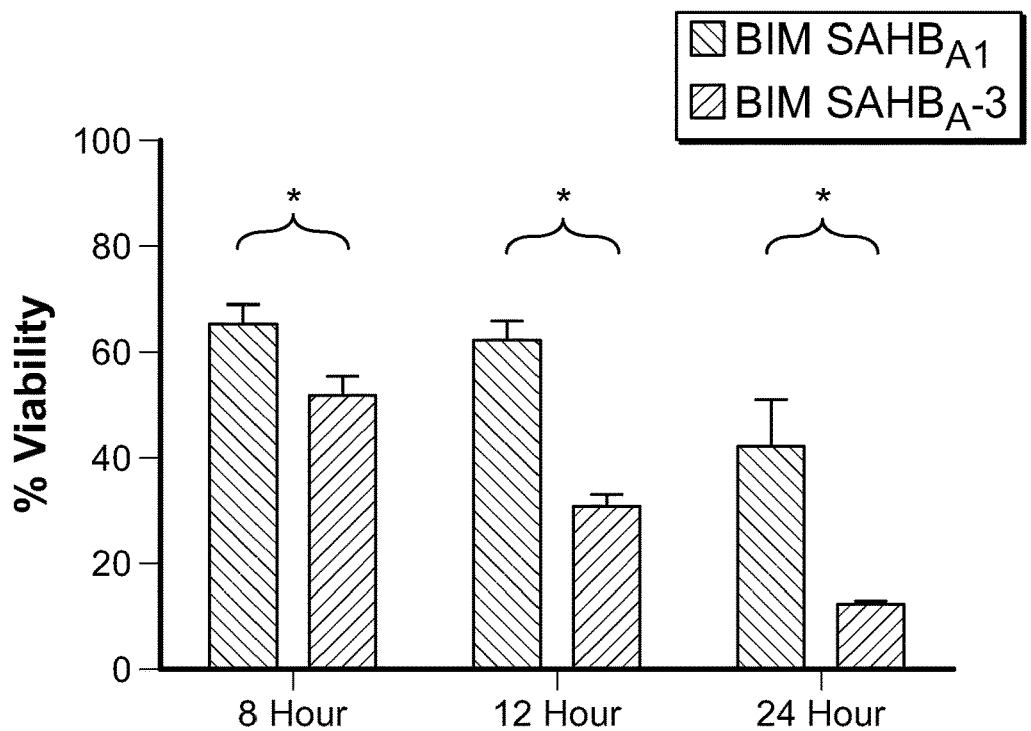
FIG. 16A: A375P cells were treated with BIM SAHB$_{A1}$ or BIM SAHB$_A$-3 (40 μM) and viability measure by CellTiter-Glo assay at the indicated time points. Data are mean+s.d. for experiments performed in technical sextuplicate, and repeated twice using independent cell cultures with similar results.
Figure 16B:
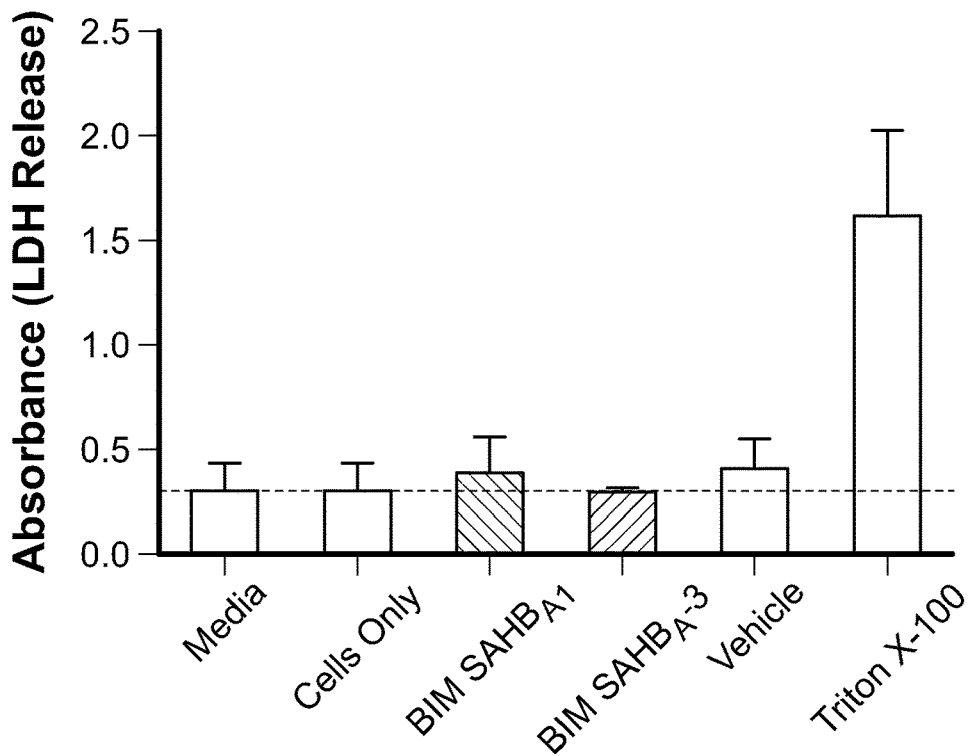
FIG. 16B: Quantitation of LDH release upon treatment of A375P cells BIM SAHB$_{A1}$ or BIM SAHB$_A$-3 (40 μM) for 30 min. Data are mean+s.d. for experiments performed in technical triplicate.
Figure 16C:
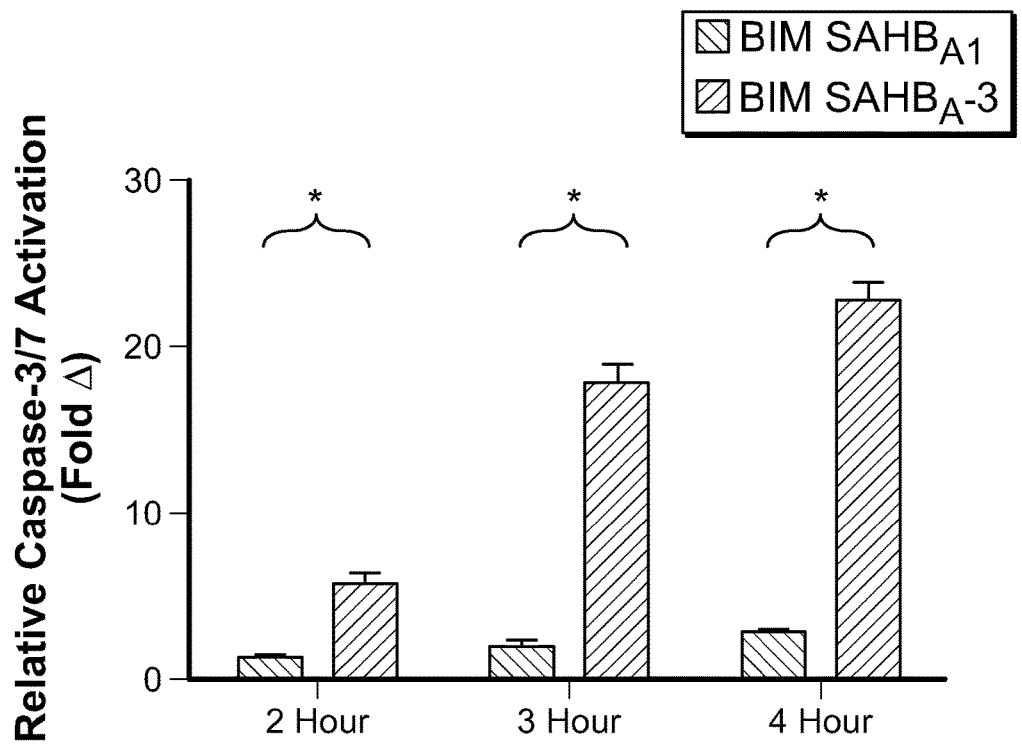
FIG. 16C: A375P cells were treated with BIM SAHB$_{A1}$ or BIM SAHB$_A$-3 (40 μM) and caspase 3/7 activation measured by CaspaseGlo assay at the indicated time points. Data are mean s.d. for experiments performed in technical sextuplicate, and repeated twice using independent cell cultures with similar results.
Figure 16D:
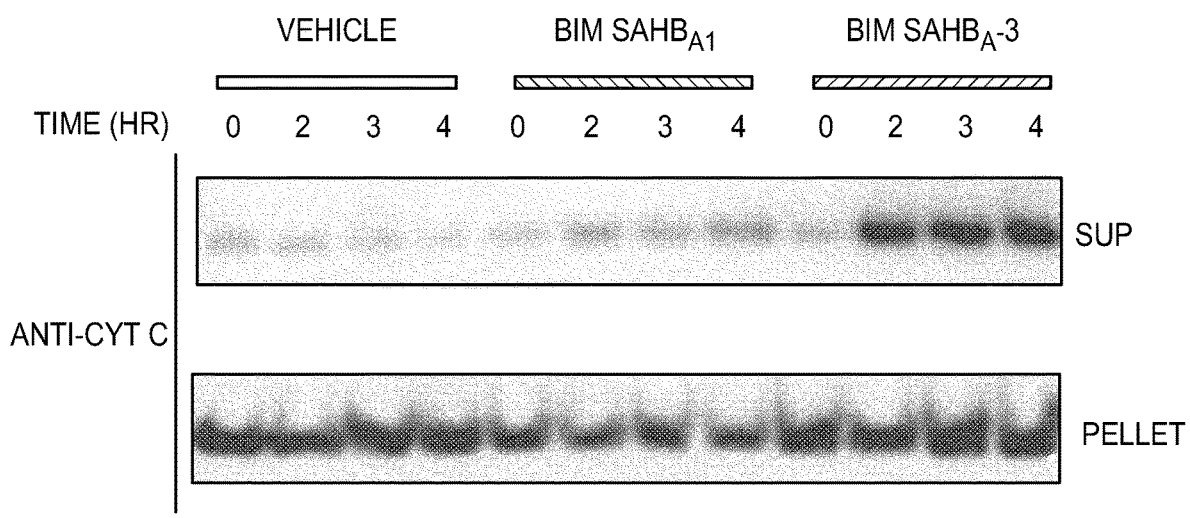
FIG. 16D: Mitochondrial cytochrome c release in A375P cells treated with BIM SAHB$_{A1}$ or BIM SAHB$_A$-3 (40 μM), as detected by cytochrome c western analysis of cytosolic and mitochondrial fractions harvested at the indicated time points. *, p<0.001 by two-tailed Student's t test.
Figure 17A:
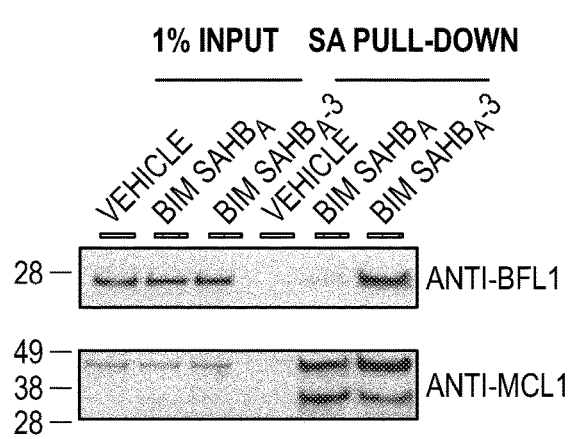
FIG. 17A: Enhanced targeting of native BFL-1 by biotinylated BIM SAHB$_A$-3, as compared to BIM SAHB$_A$, in A375P lysates, as monitored by SA pull-down and BFL-1 western analysis (top). In contrast, both compounds are equally effective at engaging MCL-1, which bears no cysteine in its BH3-binding groove and thus provides no competitive advantage for BIM SAHB$_A$-3 (bottom).
Figure 17B:
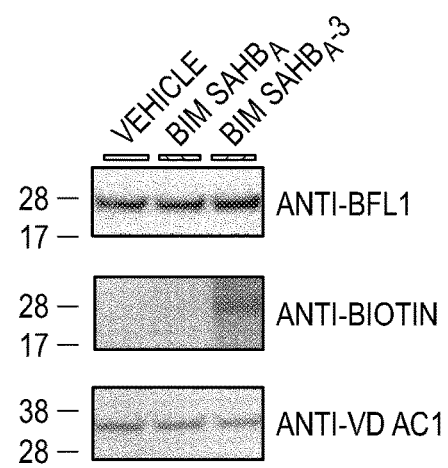
FIG. 17B: BIM SAHB$_A$-3, but not BIM SAHB$_A$, biotinylates mitochondrial protein that migrates at the same molecular weight as immunoreactive BFL-1.
Figure 17C:
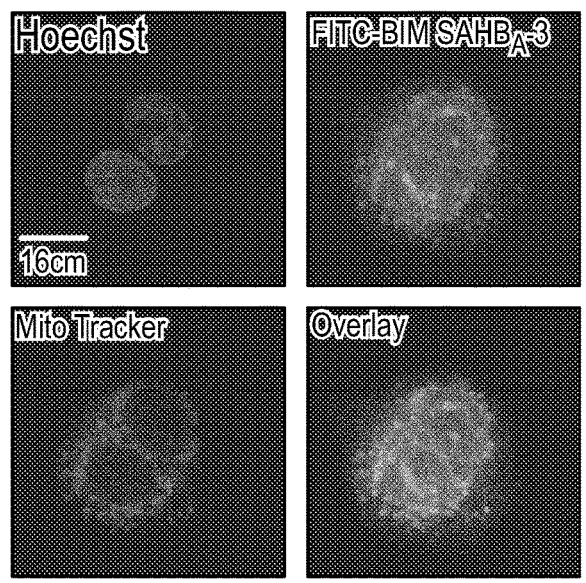
FIG. 17C: Live confocal microscopy of A375P cells treated with FITC-BIM SAHB$_A$-3 reveals its localization at the mitochondria, the intracellular site of native BFL-1. Bar, 10 μm.
Figure 17D:
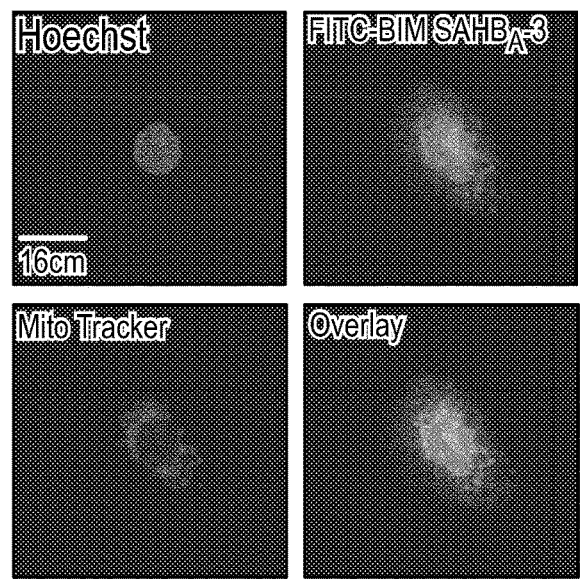
FIG. 17D: A FITC-BIM SAHB$_A$-3-treated A375P cell is observed to undergo apoptosis induction, as manifested by cell shrinkage, nuclear condensation, and membrane blebbing. The colocalization FITC-BIM SAHB$_A$-3 and MitoTracker is also evident, as described above. Bar, 10 μm.
Figure 19:
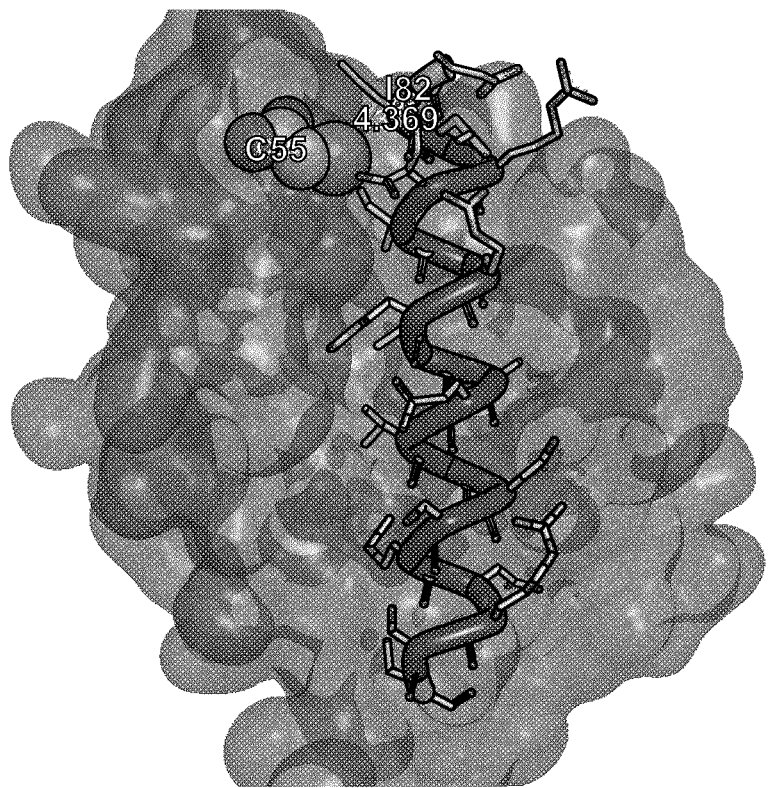
FIG. 19: Crystal structure of human Bfl-1 in complex with Tbid BH3 peptide annotated with protein target cysteine residue number, proximal helix residue number, and distance in Angstroms. Below the crystal structure are exemplary stapled peptide sequences of BID BH3. J=non-natural electrophile containing amino acid (but can be an electrophilic warhead that does not comprise an amino acid); B=norleucine, 8=R8, X=non-natural amino acid with olefinic side chain (e.g., S5).
Figure 21:
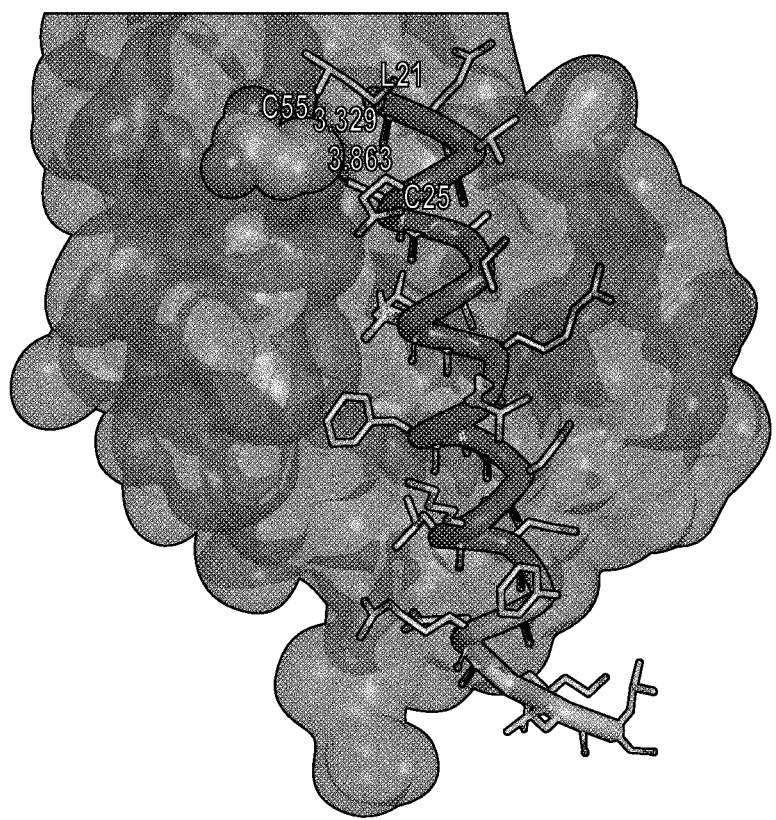
FIG. 21: Crystal structure of human Bfl-1 in complex with NOXA BH3 peptide with 30 position L21 of NOXA BH3 identified.
Figure 22:
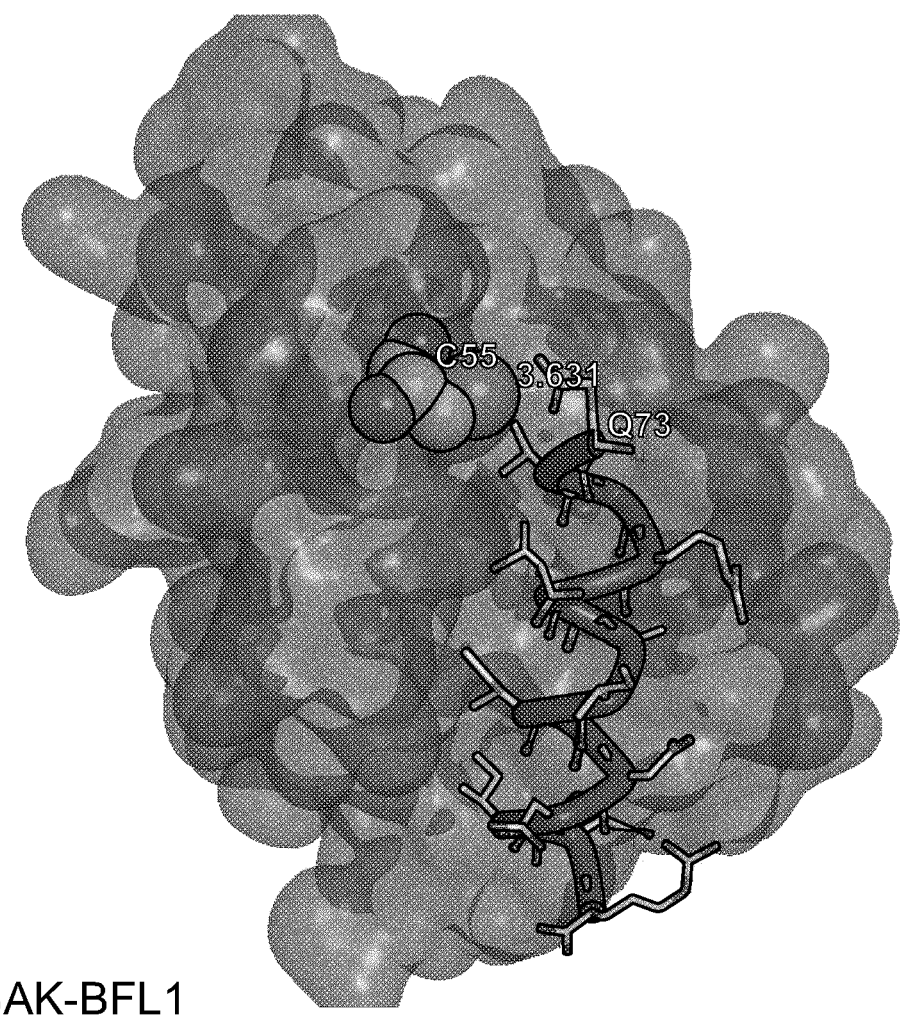
FIG. 22: Crystal structure of human Bfl-1 in complex with BAK BH3 peptide annotated with protein target cysteine residue number, proximal helix residue number, and distance in Angstroms. J=non-natural electrophile containing amino acid (but can be an electrophilic warhead that does not comprise an amino acid): 8=R-octenyl alanine.
Figure 25:
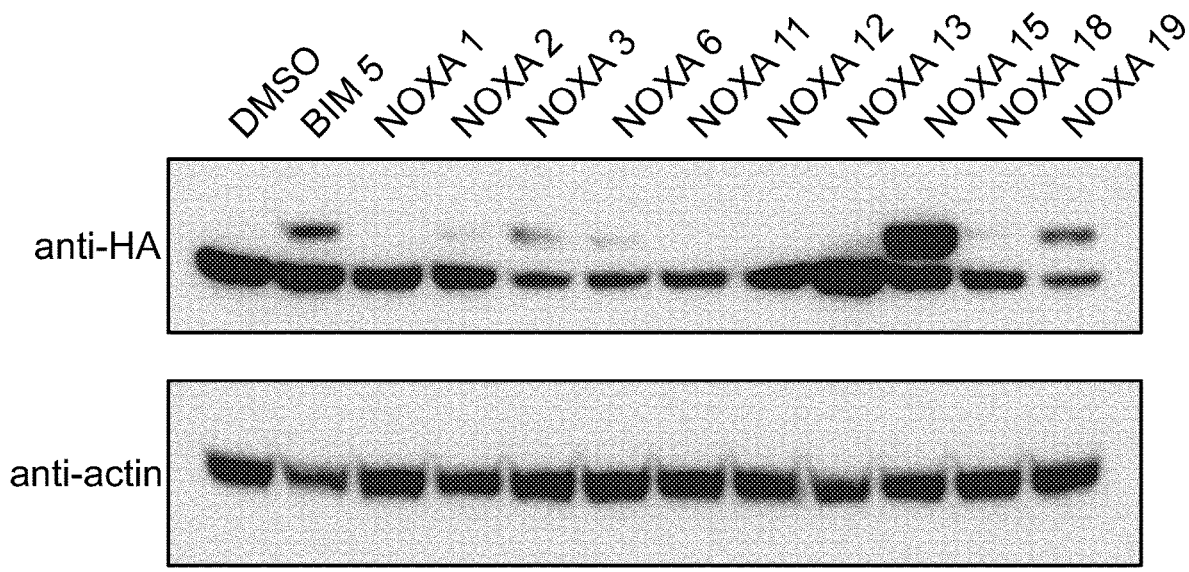
FIG. 25: Warhead-bearing peptides display intracellular crosslinking of expressed BFL-1.

Upon exposure of A375P cells to BIM SAHBs, we observed significant enhancement in cytotoxicity over time for the warhead-bearing BIM SAHB$_A$-3 compared to BIM SAHB$_{A1}$ (FIG. 16A). We confirmed by LDH release assay that BIM SAHBs had no membranolytic effect on the cells (FIG. 16B). The observed cytotoxicity was instead consistent with mitochondrial apoptosis induction, as reflected by time-responsive caspase 3/7 activation (FIG. 16C) and mitochondrial cytochrome c release (FIG. 16D). In accordance with its more pronounced impairment of cell viability, BIM SAHB$_A$-3 treatment induced higher levels of caspase 3/7 activation and cytochrome c release compared to that observed for BIM SAHB$_{A1}$ (FIG. 16C-D). To mechanistically link the enhanced susceptibility of A375P cells to preferential BIM SAHB$_A$-3 engagement of BFL-1, we incubated A375P lysates with the corresponding biotinylated BIM SAHBs, followed by SA pull-down and anti-BFL-1 and MCL-1 western analyses. Whereas BIM SAHB$_A$ and BIM SAHB$_A$-3 demonstrated equivalent binding to anti-apoptotic MCL-1, as previously observed in the context of competitive interaction with recombinant anti-apoptotic proteins (FIG. 13B), the warhead-bearing construct again showed markedly increased engagement of BFL-1 (FIG. 17A). To verify that BIM SAHB$_A$-3 can indeed label native mitochondrial BFL-1, we incubated mitochondria purified from A375P cells with biotinylated BIM SAHBs and observed BIM SAHB$_A$-3-selective biotinylation of mitochondrial protein at the identical molecular weight as immunoreactive BFL-1 (FIG. 17B). Live confocal microscopy imaging of A375P cells treated with FITC-BIM SAHB$_A$-3 further revealed the stapled peptide's striking intracellular localization at the mitochondria, the physiologic site of BFL-1 activity, in both morphologically normal A375P cells (FIG. 17C) and those undergoing apoptosis induction, as reflected by cell shrinkage, nuclear condensation, and membrane blebbing (FIG. 17D).

Importantly, we observed comparative enhancement in cytotoxicity and caspase 3/7 activation for BIM SAHB$_A$-3 in two additional BFL-1 expressing melanoma cell lines (SK-MEL-2, SK-MEL-28) (data not shown), but no evidence of this phenomenon in non-melanoma lines that either lack or maintain BFL-1 expression, but are driven by alternate oncogenic mechanisms (e.g., A549, MCF7, H929) (data not shown).

Taken together, these data highlight the mechanistic advantage of the warhead-bearing BIM SAHB$_A$-3 in the context of BFL-1-dependent cancer, as reflected by more effective engagement of native BFL-1 and greater efficacy in triggering apoptosis. Thus, in addition to harnessing a cysteine-reactive targeting strategy to selectively trap BFL-1, heightened susceptibility to covalent BFL-1 inhibitors such as BIM SAHB$_A$-3 also provide a diagnostic approach for identifying BFL-1 dependency in human cancers.

Methods Used in Examples 5-8

Stapled Peptide Synthesis: Hydrocarbon-stapled peptides corresponding to the BH3 domains of BCL-2 family proteins, and either N-terminally derivatized with acetyl, FITC-βA1a, biotin-PEG, or electrophilic warheads, or C-terminally derivatized with Lys-biotin, were synthesized, purified, and quantitated using our previously reported methods (Bird et al., Methods Enzymol., 446:369-386 (2008); Bird et al., *Curr. Protoc. Chem. Biol.*, 3:99-117 (2011)). Acrylamide-bearing peptides were synthesized by either coupling acrylic acid or trans-crotonic acid to the peptide N-terminus, or by first coupling the Fmoc protected cyclic amino acids (Chem-Impex International) followed by Fmoc deprotection and acylation with acrylic acid, using standard Fmoc coupling and deprotection methods. FITC derivatization of acrylamide-bearing peptides are detailed below. Stapled peptide compositions, and their observed masses and use by figure, are shown in FIG. 18.

FITC Derivatization of Acrylamide-Bearing Stapled Peptides: Cystamine dihydrochloride (1 eq) was dissolved in 10 mL DMSO, accompanied by 270 μL DIEA (3 eq), and then 400 mg (2 eq) of FITC was added. The reaction was monitored by LCMS and, after overnight stirring and reaction completion, 2 eq TCEP in 1 mL of water was added. The reduced product was purified on an Isco CombiFlash purification system equipped with a 40 g C18 reversed phase column using a water-acetonitrile gradient. The fractions containing product were lyophilized to afford 385 mg of FITC-labeled cysteamine. The subsequent conjugation reaction with acrylamide-containing stapled peptide was found to be pH dependent as expected, with no reaction occurring at pH 6 and pH 8, whereas the reaction in pH 10 borate buffer went to completion after overnight incubation in a 1:1:3 solution of 1 mM DMSO peptide stock, 5 mM DMSO stock of FITC-cysteamine, and 0.05 M borate buffer. The FITC-labeled peptide product, FITC-Cyste-3, was then purified by HPLC.

Recombinant Protein Expression and Purification: The recombinant anti-apoptotic proteins. BFL-1ΔC (aa 1-153). MCL-1ΔNΔC (aa 170-327) and BCL-X$_L$ΔC (aa 1-212) were cloned into the pET19b (Novagen; BFL-1ΔC) or pGEX-4T-1 (GE Healthcare; MCL-1ΔNΔC, BCL-X$_L$ΔC) expression vectors, expressed in *Escherichia coli* BL21(DE3), and purified by sequential affinity and size exclusion chromatography as described (Pitter et al., *Methods Enzvmol.*, 446, 387-408 (2008)) and detailed below.

cDNA encoding BFL-1ΔC (aa 1-153) was cloned into the pET19b expression vector (Novagen) followed by DNA sequencing to verify the construct. Constructs bearing cysteine to serine mutations were created by PCR-based site-directed mutagenesis (QuikChange Mutagenesis Kit, Stratagene). Transformed *Escherichia coli* BL2I(DE3) LOBSTR (Andersen et al., 2013) (#EC1001, Kerafast) were cultured in ampicillin-containing Luria broth (LB) and protein expression induced with 0.5 mM isopropyl β-D-1-thiogalactopyranoside (IPTG) overnight at 16° C. Bacterial pellets were resuspended in 20 mM Tris pH 7.5, 250 mM NaCl, and two complete protease inhibitor tablets (Roche), and then microfluidized (M-110L, Microfluidics) and centrifuged at 45,000×g for 1 h. The supernatant was passed over a Ni-NTA (Qiagen) column equilibrated with 50 mM Tris pH 7.5, 250 mM NaCl. The column was sequentially washed with 25 mL of equilibration buffer containing 5 mM, 10 mM and 20 mM imidazole, and then His-BFL-IAC was eluted in equilibration buffer containing 300 mM imidazole. The fraction containing His-BFL-1ΔC was dialyzed against 50 mM Tris pH 8, 100 mM NaCl at 4° C. and then concentrated and loaded onto a Superdex S-75 (GE Healthcare) gel filtration column equilibrated with 50 mM Tris pH 8.0, 100 mM NaCl. The column was washed with 30 mL equilibration buffer and fractions containing His-BFL-1ΔC were pooled and analyzed both by SDS-PAGE electrophoresis/Coomassie stain and anti-BFL-1 (Abcam, #125259) and anti-His (Abcam, #18184) western blotting. Purified protein was then concentrated, flash frozen using liquid nitrogen, and stored at −80° C. until use.

MCL-1ΔNΔC (aa 170-327) and BCL-$X_L$ΔC (aa 1-212) constructs were cloned into pGEX-4T-1 (GE Healthcare) followed by DNA sequencing to verify the constructs. Transformed *Escherichia coli* BL21(DE3) (Sigma-Aldrich) were cultured in ampicillin-containing LB, and protein expression induced with 0.5 mM IPTG and grown for 4 h at 37° C. Bacterial pellets were resuspended in phosphate-buffered saline (PBS), 0.1% Triton X-100, and complete protease inhibitor tablet (Roche), and then microfluidized and centrifuged at 45,000×g for 1 h. Supernatants were passed over a glutathione sepharose (GE Healthcare) column equilibrated with PBS containing 0.1% Triton X-100. The column was sequentially washed with 25 mL of PBS containing 0.1% Triton X-100 and PBS, and then GST cleaved on-resin with thrombin (Sigma) overnight at 25° C. The GST-free protein was eluted with PBS, concentrated, and loaded onto a Superdex S-75 (GE Healthcare) gel filtration column equilibrated with 50 mM Tris pH 7.4, 150 mM NaCl. The column was washed with 30 mL equilibration buffer and fractions containing MCL-1 ΔNΔC or BCL-$X_L$ΔC were pooled and analyzed by SDS-PAGE electrophoresis and Coomassie staining. For GST-MCL-ΔNΔC purification, protein was eluted from the column using 50 mM Tris, pH 8.0, 10 mM GSH, concentrated, and purified by size exclusion chromatography using a Superdex S-75 gel filtration column, as described above. Purified proteins were concentrated, flash frozen using liquid nitrogen, and stored at −80° C.

Biolayer Interferometry: Binding analyses of NOXA peptide interactions with BFL-1ΔC were performed on an Octet RED384 system (Fortebio, Menlo Park, Calif.) at 30° C. Super streptavidin (SSA) tips were prewetted in 1× kinetics buffer (PBS, pH 7.4, 0.01% BSA, 0.002% Tween-20) and then conjugated to NOXA SAHBs bearing an N-terminal biotin-PEG linker (10 μg/mL). Excess streptavidin was quenched by incubation with 2 μg/mL biocytin. The tips were then washed with kinetics buffer and soaked in a serial dilution of BFL-IAC for 10 min to measure association rate, followed by a 15 min incubation in kinetics buffer to measure dissociation rate. Dissociation constants were calculated using Octet Data Analysis version 9.0.

In Vitro Covalent Conjugation Assay: BFL-1ΔC constructs (40 μM) were combined with NOXA $SAHB_A$ or NOXA $SAHB_A$ C25S (120 μM) and 10 mM DTT in 50 mM Tris pH 8.0, 100 mM NaCl (final volume, 5 μL), and then incubated in the dark for 1 h at room temperature (RT). After this incubation in a reducing environment, the mixture was diluted 5-fold into 50 mM Tris pH 8.0, 100 mM NaCl, 12 mM GSSG and incubated in the dark for an additional 30 min at RT. The samples were then boiled in 4× loading buffer lacking DTT and electrophoresed on 12% Bis-Tris gel. The gel was rinsed with water, subjected to FITC scan (Typhoon FLA 9500, GE Healthcare) and then Coomassie staining.

For warhead-bearing SAHBs, His-BFL-1ΔC C4S/C19S protein was pretreated with 10 mM DTT in 50 mM Tris pH 8.0, 100 mM NaCl for 30 min at RT (final volume, 9.5 μL), and then combined with a 10:1 molar ratio of NOXA $SAHB_A$ or BIM $SAHB_A$ peptides bearing warheads 1-8 (final volume, 10 μL) for an additional 2 h incubation at RT. Processing for gel electrophoresis and Coomassie staining was performed as above.

Streptavidin Pull-down: Recombinant His-BFL-1ΔC, BCL-$X_L$ΔC (tagless) and GST-MCL-1ΔNΔC (1 μM each) were combined and reduced with 3 mM DTT in PBS for 30 min at RT, and then incubated with 1 μM biotinylated $SAHB_A$, $SAHB_A$-3 or vehicle for 4 h at RT. The mixtures were then combined with PBS-washed high-capacity SA agarose (Thermo Fisher Pierce) and incubated with rotation for 2 h at RT. The beads were centrifuged at 3000 rpm, washed twice with NP-40 lysis buffer (1% NP40, 50 mM Tris pH 8.0, 100 mM NaCl, 2.5 mM $MgCl_2$), once with PBS, and then bound protein eluted by boiling in 10% SDS containing 10 mg/mL biotin. Inputs (10%) and eluates were electrophoresed on a 12% Bis-Tris gel and then subjected to silver stain and imaging.

Liposomal Release Assay: Liposomal release assays were performed as detailed below, with $SAHB_A$-3/BFL-1ΔC conjugates prepared by treating BFL-1ΔC (10 μM) with DTT (20 mM) for 30 min at 4° C., followed by sequential incubation with NOXA $SAHB_A$-3 or BIM $SAHB_A$-3 peptides at peptide:protein molar ratios of 1.2×, 0.75×, and 0.5× for 1 h each at 4° C.

Large unilamellar vesicles (LUVs) with encapsulated ANTS and DPX were generated and purified as described (Leshchiner et al., 2013; Lovell et al., 2008). The indicated combinations of BAX (400 nM), tBID (40 nM), and BFL-1ΔC or $SAHB_A$-3/BFL-1ΔC conjugates (1.5 μM), were added to liposomes (5 μL) in 384 well plates (final volume, 30 μL), and released fluorophore was measured over 120 min using an M1000 Infinite plate reader (Tecan) with excitation and emission wavelengths of 355 nm and 520 nm, respectively. $SAHB_A$-3/BFL-1ΔC conjugates were prepared by treating BFL-1ΔC (10 μM) with DTT (20 mM) for 30 min at 4° C., followed by sequential incubation with NOXA $SAHB_A$-3 or BIM $SAHB_A$-3 peptides at peptide:protein molar ratios of 1.2×, 0.75×, and 0.5× for 1 h each at 4° C. Conjugation efficiency was confirmed by 12% Bis-Tris gel electrophoresis and Coomassie staining. The protein conjugate was then concentrated to 75 μM, loaded onto a Superdex S-75 (GE Healthcare) gel filtration column equilibrated with 20 mM HEPES pH 7.5, 300 mM NaCl, 1 mM DTT, washed with 30 mL equilibration buffer, and fractions collected, analyzed by SDS-PAGE electrophoresis, and used fresh in liposomal assays. Percent ANTS/DPX release was calculated as $[(F-F0)/(F100-F0)] \times 100$, where F0 is baseline fluorescence at time 0, F is the fluorescence recorded for each time point, and F100 is the maximum amount of ANTS/DPX release based on liposomal treatment with 1% Triton X-100.

BFL-1 Targeting in Lysates and Cells: A series of NOXA and BIM SAHB constructs, with and without installed biotin handles and/or acrylamide warheads, were employed in comparative BFL-1 targeting assays in lysates containing or intact cells expressing HA-BFL-1ΔC C4S/C19S (transfected 293T cells) or native BFL-1 (A375P), performed as described in detail below.

293T cells were maintained in DMEM containing 10% FBS and penicillin/streptomycin, and transfections performed with 2 μg pCMV plasmid containing HA-BFL-1ΔC C4S/C19S using X-tremeGENE 9 (Roche). For lysate experiments, cells were trypsinized 24 hours post-transfection, washed with PBS, and lysed by incubation with 1% CHAPS lysis buffer (150 mM NaCl, 50 mM Tris pH 7.4, 100 mM DTT). Protein concentration of the soluble fraction was measured using a BCA kit according to manufacturer's instructions (Thermo Scientific). Biotinylated NOXA SAHB$_A$-3 or BIM SAHB$_A$-3 (10 μM) was added to 100 μg of lysate and incubated at RT for 2 h. Samples were then boiled in LDS buffer and subjected to western analysis using 1:1000 dilutions of HA (Sigma-Aldrich. #12CA5) and biotin (Abcam, #53494) antibodies. To evaluate the capacity of biotinylated SAHBs to compete with tBID for interactions with BFL-1 and MCL-1, 293T cells were transfected with either HA-BFL-1ΔC C4S/C19S or FLAG-MCL-1 in the p3XFLAG-CMV-10 vector (Sigma) as above. After 24 h, cells were trypsinized, washed with PBS, lysed in 1% CHAPS buffer, and the supernatant collected for protein concentration determination by BCA kit. Lysate samples (0.5 mg) were incubated with 0.25 μM recombinant tBID (R&D Systems) and 5 μM biotinylated BIM SAHB$_A$ or BIM SAHB$_A$-3 for 6 h at RT. The mixtures were then subjected to HA or FLAG (Sigma-Aldrich, F7425) immunoprecipitation, followed by western analysis using 1:1000 dilutions of HA, FLAG, biotin, and BID (Santa Cruz sc-11423) antibodies. For HA-immunoprecipitation from 293T cells treated with biotinylated peptides, cells were transfected with HA-BFL-1ΔC C4S/C19S as above and, after 24 hours, incubated with 20 μM biotinylated BIM SAHB$_A$ or BIM SAHB$_A$-3 in DMEM containing 5% FBS for 6 hours. Cells were harvested and lysed as above, and incubated overnight with anti-HA agarose beads (Pierce). The beads were washed 3 times with lysis buffer, eluted by boiling in LDS buffer, and subjected to western analysis with HA and biotin antibodies. For 293T treatment with non-biotinylated SAHBs, cells were transfected with HA-BFL-1ΔC C4S/C19S as above, incubated with 20 μM BIM SAHB$_A$ or BIM SAHB$_A$-3 in DMEM containing 5% FBS, and lysates harvested as above at the indicated time points for western analysis using the HA and actin antibodies. For A375P melanoma studies, cells were maintained in DMEM containing 10% FBS and penicillin/streptomycin, and biotinylated NOXA SAHB$_A$-3 or BIM SAHB$_A$-3 (30 μM) was added to 1 mg of lysate, followed by overnight incubation in CHAPS lysis buffer at 4° C. Biotin capture was accomplished by incubating the mixture with high-capacity SA agarose (Thermo Scientific) for 2 h at 4° C., followed by centrifugation and washing the pelleted beads with 3×1 mL lysis buffer. Bead-bound proteins were eluted by boiling in 10% SDS containing 10 mg/mL biotin for 10 min and then subjected to electrophoresis and western blotting using BFl-1 (Abcam, #125259) and MCL-1 (Rockland, #600-401-394S) antibodies.

Cell Viability, LDH Release, and Caspase-3/7 Activation Assays: Cancer cells were cultured using their standard culture media containing 10% FBS and penicillin/streptomycin (A375P: DMEM; SK-MEL-2, SK-MEL-28 and MCF-7: EMEM: A549, H929: RPMI). Cells were plated in 96-well plates (5×10' cells per well) and, after overnight incubation, treated with the indicated concentrations of BIM SAHB$_{A1}$ or BIM SAHB$_A$-3 in the corresponding media supplemented with 5% FBS for the indicated durations. Cell viability and caspase 3/7 activation was measured using CellTiter-Glo and Caspase-Glo 3/7 chemiluminescence reagents (Promega), respectively, and luminescence detected by a microplate reader (Spectramax M5, Molecular Devices). LDH release was quantified after 30 min peptide incubation by plate centrifugation at 1500 rpm for 5 min at 4° C., transfer of 100 μL cell culture media to a clear plate (Corning), incubation with 100 μL LDH reagent (Roche) for 30 min while shaking, and measurement of absorbance at 490 nm on a Spectramax M5 microplate reader.

Mitochondrial Cytochrme c Release and Biotinylation Assays: A375P cells were plated in 6-well Corning plates (3×10$^5$ cells/well) and cultured as above. After 24 h, the cells were treated with BIM SAHB$_{A1}$ or BIM SAHB$_A$-3 (40 μM) in DMEM containing 5% FBS for the indicated durations, and then trypsinized, washed with PBS, and cytosol (supernatant) and mitochondrial (pellet) fractions isolated as described (Dewson, 2015). Briefly, pelleted cells were resuspended at 1×10$^7$ cells/mL in permeabilization buffer (20 mM HEPES/KOH pH 7.5, 250 mM sucrose, 50 mM KCl, 2.5 mM MgCl$_2$) supplemented with 0.025% digitonin and protease inhibitors, followed by incubation on ice for 10 min and centrifugation at 13,000 g.

The resultant supernatant and pellet fractions were boiled in LDS buffer and subjected to western analysis using a 1:1000 dilution of cytochrome c antibody (BD Pharmingen #556433). For biotinylation studies, A375P mitochondria were isolated as above, resuspended in permeabilization buffer, and then treated with biotinylated BIM SAHB$_A$ or BIM SAHB$_4$-3 (50 μM) for 4 h at RT. Samples were then boiled in LDS buffer and subjected to western analysis using 1:1000 dilutions of BFL1 (Abcam #125259), biotin (Abcam, #53494), and VDAC1 (Abcam #14734) antibodies.

Confocal Microscopy: A375P cells were plated in chambered coverglass (1.5×10$^4$ cells/well) and cultured as above. After 24 h, cells were treated with FITC-BIM SAHB$_{A1}$ or BIM SAHB$_A$-3 (1 μM) for 4 h in phenol-free DMEM containing 5% FBS. Cells were washed, stained with MitoTracker Red (Thermo), Hoescht 33342, and imaged live. Confocal images were collected with a Yokogawa CSU-X1 spinning disk confocal (Andor Technology) mounted on a Nikon Ti-E inverted microscope (Nikon Instruments). Images were acquired using a 100×1.4 NA Plan Apo objective lens with an Orca ER CCD camera (Hamamatsu Photonics) and 488 nm laser. Acquisition parameters, shutters, filter positions and focus were controlled by Andor iQ software (Andor Technology).

Cellular Uptake of Stapled Peptides: To evaluate cellular uptake of biotinylated SAHBs by biotin western analysis of electrophoresed lysates from treated cells, 293T cells were plated in 6-well Corning plates (2×10$^5$ cells/well) in DMEM containing 10% FBS and penicillin/streptomycin. After 24 h, biotinylated NOXA SAHB$_A$-3 or BIM SAHB$_A$-3 peptides (20 μM) were added to the cells in DMEM containing 5% FBS for an additional 24 h incubation. The cells were then trypsinized to remove any surface-bound peptide, washed with PBS, lysed as above in 1% CHAPS lysis buffer, and the supernatant collected for protein concentration determination by BCA kit according to manufacturer's instructions (Thermo Scientific). Cellular lysate samples (50 μg) were boiled in LDS buffer and subjected to western analysis using a 1:1000 dilution of anti-biotin (Abcam, #53494) and 1:2000 dilution of anti-actin (Sigma-Aldrich, #A1978) antibodies. To evaluate the potential effect of transfection conditions on stapled peptide uptake, 293T cells were plated in 6-well Corning plates (2×10⁵ cells/well) and cultured as above. After 24 h, a mock transfection was performed with X-tremeGENE 9 (Roche) and no plasmid alongside control cells that were not transfected. After an addition 24 hour incubation, 20 µM biotinylated BIM SAHB$_A$-3 peptide was added to the cells in DMEM containing 5% FBS and incubated for 4 h. Cells were then washed, trypsinized, and lysed as above, and lysates subjected to biotin and actin western analyses. For cellular uptake analysis by ImageXpress high-content epifluorescence microscopy, the indicated cell lines were plated in black, clear bottom 96-well plates overnight at a density of 1.5×10' cells per well for MEFs or 1×10⁴ cells per well for A375P cells in DMEM supplemented with 10% FBS, 1% penicillin/streptomycin, and 1% glutamine. The following day, cells were treated with the FITC-labeled peptides or the equivalent amount of vehicle (0.1% DMSO) for 4 h in DMEM supplemented with 5% FBS, and then stained with Hoechst 33342 and CellMask Deep Red (CMDR, Invitrogen) for 10 min. The media was then aspirated and cells fixed with 4% (wt/vol) paraformaldehyde for 10 min, followed by washing three times with PBS and an imaging by ImageXpress Microscopy (Molecular Devices). Data were collected for five sites per well at 20× magnification, with each treatment performed in triplicate, and then analyzed and quantified using MetaXpress software. The CMDR stain was used to visualize the boundaries of the cell and to create a mask for measuring FITC-peptide inside the cell, thereby excluding fluorescent debris from the analysis. A custom module in MetaXpress was applied to incrementally recede the CMDR image mask from the cellular border, further restricting the analyzed FITC signal to internalized peptide. The measurement of Total Internalized Fluorescence Intensity (TIFI) represents the level of absolute fluorescence detected per cell, per peptide construct. Maximum and minimum thresholding was utilized to exclude FITC and Cy5 outliers that were much larger and brighter than average, and total intensity and average intensity per cell thresholds were set such that vehicle-treated cells scored negative by the analysis.

Statistical Analysis: Datasets were analyzed by two-tailed Student's t test, with $p<0.05$ considered statistically significant.

Example 9: Warhead-Bearing NOXA Peptides Display Intracellular Crosslinking of Expressed BFL-1

293T cells were transfected with HA-BFL-1ΔC C4S/C19S and subsequently incubated with 20 µM warhead-bearing BIM or NOXA-SAHBs in DMEM containing 5% FBS for 2 hours. Cells were washed and lysed, and then lysates isolated for western analysis using the HA and actin antibodies. A series of warhead-bearing NOXA peptides display intracellular crosslinking of expressed BFL-1, with the most effective agent of the tested panel being NOXA 15.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A polypeptide that binds to Bfl-1, the polypeptide comprising:
   (a) the amino acid sequence set forth in SEQ ID NO: 22-36, 41-119, 184, 186, 195, 197, or 208, wherein the polypeptide comprises a non-natural amino acid bearing an electrophilic group or an electrophilic warhead at the N-terminus of the amino acid sequence;
   (b) an amino acid sequence that is at least 50% identical to the Bfl-1 interacting alpha-helical face of ATQLRRFGDKLNFRQ (SEQ ID NO:121) and that selectively binds Bfl-1 over MCL-1, wherein at least two amino acids in the amino acid sequence of SEQ ID NO:121 are substituted by non-natural amino acids with olefinic side chains, wherein F at position 7 of the amino acid sequence of SEQ ID NO:121 is substituted with an amino acid with a bulkier side chain, and wherein the polypeptide comprises a non-natural amino acid bearing an electrophilic group or an electrophilic warhead at the N-terminus of the amino acid sequence;
   (c) an amino acid sequence that is at least 50% identical to the Bfl-1 interacting alpha-helical face of an amino acid sequence set forth below:

(i)
   (SEQ ID NO: 122)
   AELEVECATQLRRFGDKLNFRQKLLN;

(ii)
   (SEQ ID NO: 123)
   EIWIAQELRRIGDEFNAYYARR;

(iii)
   (SEQ ID NO: 124)
   DIIRNIARHLAQVGDSMDRSI;

(iv)
   (SEQ ID NO: 125)
   SSTMGQVGRQLAIIGDDINRRY;

-continued (v)
QDASTKKLSESLKRIGDELDSNMEL; (SEQ ID NO: 126)
or (vi)
RLAEVCAVLLRLGDELEMIR, (SEQ ID NO: 127)

wherein the polypeptide selectively binds Bfl-1 over MCL-1;
wherein at least two amino acids in each amino acid sequence are substituted by non-natural amino acids with olefinic side chains,
wherein at least one cysteine if present in the polypeptide is optionally replaced by serine, and wherein at least one methionine if present in the polypeptide is optionally replaced by norleucine; and
wherein the polypeptide comprises a non-natural amino acid bearing an electrophilic group or a non-amino acid warhead at the N-terminus of the amino acid sequence;
(d) an amino acid sequence that is at least 50% identical to the Bfl-1 interacting alpha-helical face of JATQLRRFGDKLNFRQKLL (SEQ ID NO: 128) and that selectively binds Bfl-1 over MCL-1; wherein the polypeptide forms a covalent bond with Cys 55 of Bfl-1; wherein at least two amino acids in the amino acid sequence of SEQ ID NO:128 are substituted by non-natural amino acids with olefinic side chains, and wherein J is a non-natural amino acid bearing an electrophilic group, or an electrophilic warhead that does not comprise an amino acid;
(e) an amino acid sequence that is at least 50% identical to the Bfl-1 interacting alpha-helical face of JEVESATQLRRFGDKLNFRQKLL (SEQ ID NO:129) and that selectively binds Bfl-1 over MCL-1; wherein the polypeptide forms a covalent bond with Cys 55 of Bfl-1; wherein at least two amino acids in the amino acid sequence of SEQ ID NO:129 are substituted by non-natural amino acids with olefinic side chains, and wherein J is a non-natural amino acid bearing an electrophilic group, or an electrophilic warhead that does not comprise an amino acid;
(f) an amino acid sequence that is at least 50% identical to the Bfl-1 interacting alpha-helical face of JIAQELRRIGDEFNAYYARR (SEQ ID NO: 130) and that selectively binds Bfl-1 over MCL-1; wherein the polypeptide forms a covalent bond with Cys 55 of Bfl-1; wherein at least two amino acids in the amino acid sequence of SEQ ID NO:130 are substituted by non-natural amino acids with olefinic side chains, and wherein J is a non-natural amino acid bearing an electrophilic group, or an electrophilic warhead that does not comprise an amino acid;
(g) an amino acid sequence with 1 to 5 amino acid substitutions relative to the amino acid sequence set forth in SEQ ID NO: 22-36, 41-119, 184, 186, 195, 197, or 208, wherein the polypeptide selectively binds Bfl-1 over MCL-1 and forms a covalent bond with Cys 55 of Bfl-1, and wherein the polypeptide comprises a non-natural amino acid bearings an electrophilic group or an electrophilic warhead at the N-terminus of the amino acid sequence; or
(h) an amino acid sequence with 1 to 5 amino acid substitutions relative to the amino acid sequence set forth in SEQ ID NO: 128, wherein the polypeptide selectively binds Bfl-1 over MCL-1 and forms a covalent bond with Cys 55 of Bfl-1, and wherein the polypeptide comprises a non-natural amino acid bearing an electrophilic group or an electrophilic warhead at the N-terminus of the amino acid sequence.

2. A method for treating a human subject suffering from a cancer that exhibits expression of BFL-1 or dependency on BFL-1, the method comprising administering a therapeutically effective amount of the polypeptide of claim 1 to the human subject.

3. The method of claim 2, wherein a biological sample comprising a tumor from the human subject is or has previously been determined to express Bfl-1.

4. A pharmaceutical composition comprising the polypeptide of claim 1, and a pharmaceutically acceptable carrier.

5. A method for treating a human subject suffering from a cancer that exhibits expression of BFL-1 or dependency on BFL-1, the method comprising administering to the human subject a therapeutically effective amount of the pharmaceutical composition of claim 4.

6. The polypeptide of claim 1, wherein the polypeptide comprises the amino acid sequence set forth in SEQ ID NQ: 22-36, 41-119, 184, 186, 195, 197, or 208, and wherein the polypeptide comprises a non-natural amino acid bearing an electrophilic group or an electrophilic warhead at the N-terminus of the amino acid sequence.

7. The polypeptide of claim 1, wherein the polypeptide comprises an amino acid sequence with 1 to 5 amino acid substitutions relative to the amino acid sequence set forth in SEQ ID NO: 22-36, 41-119, 184, 186, 195, 197, or 208, wherein the polypeptide comprises a non-natural amino acid bearing an electrophilic group or an electrophilic warhead at the N-terminus of the amino acid sequence, and wherein the polypeptide selectively binds Bfl-1 over MCL-1 and forms a covalent bond with Cys 55 of Bfl-1.

8. The polypeptide of claim 1, wherein the polypeptide comprises an amino acid sequence with 1 or 2 amino acid substitutions relative to the amino acid sequence set forth in SEQ ID NQ: 22-36, 41-119, 184, 186, 195, 197, or 208, wherein the polypeptide comprises a non-natural amino acid bearing an electrophilic group or an electrophilic warhead at the N-terminus of the amino acid sequence, and wherein the polypeptide selectively binds Bfl-1 over MCL-1 and forms a covalent bond with Cys 55 of Bfl-1.

9. The polypeptide of claim 1, wherein the polypeptide is stapled.

10. A pharmaceutical composition comprising the polypeptide of claim 9 and a pharmaceutically acceptable carrier.

11. A method for treating a human subject suffering from a cancer that exhibits expression of BFL-1 or dependency on BFL-1, the method comprising administering a therapeutically effective amount of the polypeptide of claim 9 to the human subject.

12. The polypeptide of claim 1, wherein the polypeptide comprises an amino acid sequence with 1 to 5 amino acid substitutions relative to the amino acid sequence set forth in SEQ ID NO: 128, wherein the polypeptide comprises a non-natural amino acid bearing an electrophilic group or an electrophilic warhead at the N-terminus of the amino acid sequence, and wherein the polypeptide selectively binds Bfl-1 over MCL-1 and forms a covalent bond with Cys 55 of Bfl-1.

13. The polypeptide of claim 1, wherein the polypeptide comprises an amino acid sequence with 2 to 3 amino acid substitutions relative to the amino acid sequence set forth in SEQ ID NO: 128, wherein the polypeptide comprises a non-natural amino acid bearing an electrophilic group or an electrophilic warhead at the N-terminus of the amino acid sequence, and wherein the polypeptide selectively binds Bfl-1 over MCL-1 and forms a covalent bond with Cys 55 of Bfl-1.

14. The polypeptide of claim 1, wherein the polypeptide comprises the amino acid sequence set forth in SEQ ID NO: 22-25, 49-67, 184, or 186, and wherein the polypeptide comprises a non-natural amino acid bearing an electrophilic group or an electrophilic warhead at the N-terminus of the amino acid sequence.

15. The polypeptide of claim 1, wherein the polypeptide comprises an amino acid sequence that is at least 50% identical to the Bfl-1 interacting alpha-helical face of ATQLRRFGDKLNFRQ (SEQ ID NO:121) and that selectively binds Bfl-1 over MCL-1, wherein at least two amino acids in the amino acid sequence of SEQ ID NO:121 are substituted by non-natural amino acids with olefinic side chains, wherein F at position 7 of the amino acid sequence of SEQ ID NO:121 is substituted with an amino acid with a bulkier side chain, and wherein the polypeptide comprises a non-natural amino acid bearing an electrophilic group or an electrophilic warhead at the N-terminus of the amino acid sequence.

16. The polypeptide of claim 1, wherein the polypeptide comprises an amino acid sequence that is at least 90% identical to the Bfl-1 interacting alpha-helical face of ATQLRRFGDKLNFRQ (SEQ ID NO:121) and that selectively binds Bfl-1 over MCL-1, wherein at least two amino acids in the amino acid sequence of SEQ ID NO:121 are substituted by non-natural amino acids with olefinic side chains, wherein F at position 7 of the amino acid sequence of SEQ ID NO:121 is substituted with an amino acid with a bulkier side chain, and wherein the polypeptide comprises a non-natural amino acid bearing an electrophilic group or an electrophilic warhead at the N-terminus of the amino acid sequence.

17. The polypeptide of claim 1, wherein the polypeptide comprises the amino acid sequence that is at least 50% identical to the Bfl-1 interacting alpha-helical face of JATQLRRFGDKLNFRQKLL (SEQ ID NO: 128) and that selectively binds Bfl-1 over MCL-1; wherein the polypeptide forms a covalent bond with Cys 55 of Bfl-1; wherein at least two amino acids in the amino acid sequence of SEQ ID NO:128 are substituted by non-natural amino acids with olefinic side chains, and wherein J is a non-natural amino acid bearing an electrophilic group, or an electrophilic warhead that does not comprise an amino acid.

18. The polypeptide of claim 1, wherein the polypeptide comprises the amino acid sequence that is at least 90% identical to the Bfl-1 interacting alpha-helical face of JATQLRRFGDKLNFRQKLL (SEQ ID NO: 128) and that selectively binds Bfl-1 over MCL-1; wherein the polypeptide forms a covalent bond with Cys 55 of Bfl-1; wherein at least two amino acids in the amino acid sequence of SEQ ID NO:128 are substituted by non-natural amino acids with olefinic side chains, and wherein J is a non-natural amino acid bearing an electrophilic group, or an electrophilic warhead that does not comprise an amino acid.

19. The polypeptide of claim 1, wherein the polypeptide comprises the amino acid sequence that is at least 50% identical to the Bfl-1 interacting alpha-helical face of JEVE-SATQLRRFGDKLNFRQKLL (SEQ ID NO:129) and that selectively binds Bfl-1 over MCL-1; wherein the polypeptide forms a covalent bond with Cys 55 of Bfl-1; wherein at least two amino acids in the amino acid sequence of SEQ ID NO:129 are substituted by non-natural amino acids with olefinic side chains, and wherein J is a non-natural amino acid bearing an electrophilic group, or an electrophilic warhead that does not comprise an amino acid.

20. The polypeptide of claim 1, wherein the polypeptide comprises the amino acid sequence that is at least 90% identical to the Bfl-1 interacting alpha-helical face of JEVE-SATQLRRFGDKLNFRQKLL (SEQ ID NO:129) and that selectively binds Bfl-1 over MCL-1; wherein the polypeptide forms a covalent bond with Cys 55 of Bfl-1; wherein at least two amino acids in the amino acid sequence of SEQ ID NO:129 are substituted by non-natural amino acids with olefinic side chains, and wherein J is a non-natural amino acid bearing an electrophilic group, or an electrophilic warhead that does not comprise an amino acid.

21. The polypeptide of claim 1, wherein the polypeptide comprises the amino acid sequence that is at least 50% identical to the Bfl-1 interacting alpha-helical face of JIAQELRRIGDEFNAYYARR (SEQ ID NO: 130) and that selectively binds Bfl-1 over MCL-1; wherein the polypeptide forms a covalent bond with Cys 55 of Bfl-1; wherein at least two amino acids in the amino acid sequence of SEQ ID NO:130 are substituted by non-natural amino acids with olefinic side chains, and wherein J is a non-natural amino acid bearing an electrophilic group, or an electrophilic warhead that does not comprise an amino acid.

22. The polypeptide of claim 1, wherein the polypeptide comprises the amino acid sequence that is at least 90% identical to the Bfl-1 interacting alpha-helical face of JIAQELRRIGDEFNAYYARR (SEQ ID NO: 130) and that selectively binds Bfl-1 over MCL-1; wherein the polypeptide forms a covalent bond with Cys 55 of Bfl-1; wherein at least two amino acids in the amino acid sequence of SEQ ID NO:130 are substituted by non-natural amino acids with olefinic side chains, and wherein J is a non-natural amino acid bearing an electrophilic group, or an electrophilic warhead that does not comprise an amino acid.

23. The polypeptide of claim 1, wherein the polypeptide comprises an amino acid sequence with 1 to 5 amino acid substitutions relative to the amino acid sequence set forth in SEQ ID NO: 22-25, 49-67, 184, or 186, wherein the polypeptide comprises a non-natural amino acid bearing an electrophilic group or an electrophilic warhead at the N-terminus of the amino acid sequence, and wherein the polypeptide selectively binds Bfl-1 over MCL-1 and forms a covalent bond with Cys 55 of Bfl-1.

24. The polypeptide of claim 1, wherein the polypeptide comprises an amino acid sequence with 1 or 2 amino acid substitutions relative to the amino acid sequence set forth in SEQ ID NO: 22-25, 49-67, 184, or 186, wherein the polypeptide comprises a non-natural amino acid bearing an electrophilic group or an electrophilic warhead at the N-terminus of the amino acid sequence, and wherein the polypeptide selectively binds Bfl-1 over MCL-1 and forms a covalent bond with Cys 55 of Bfl-1.

25. The polypeptide of claim 1, wherein the non-natural amino acid bearing an electrophilic group or the electrophilic warhead at the N-terminus of the amino acid sequence is (S)-1-acryloylpyrrolidine-3-carboxamide, 1-acryloylpiperidine-4-carboxamide, (R)-1-acryloylpiperidine-3-carboxamide, (S)-1-acryloylpiperidine-3-carboxamide, (S)-1-acryloylpyrrolidine-2-carboxamide, (R)-1-acryloylpyrrolidine-2-carboxamide, (E)-4-(dimethylamino)but-2-enamide, or acrylamide.

26. The polypeptide of claim 1, wherein the non-natural amino acid bearing an electrophilic group or the electrophilic warhead at the N-terminus of the amino acid sequence is (R)-1-acryloylpiperidine-3-carboxamide.

27. The polypeptide of claim 1, wherein the polypeptide comprises an amino acid sequence that is at least 90% identical to the Bfl-1 interacting alpha-helical face of an amino acid sequence set forth below:

(i)
AELEVECATQLRRFGDKLNFRQKLLN;   (SEQ ID NO: 122)

(ii)
EIWIAQELRRIGDEFNAYYARR;   (SEQ ID NO: 123)

(iii)
DIIRNIARHLAQVGDSMDRSI;   (SEQ ID NO: 124)

(iv)
SSTMGQVGRQLAIIGDDINRRY;   (SEQ ID NO: 125)

(v)
QDASTKKLSESLKRIGDELDSNMEL;   (SEQ ID NO: 126)
or (vi)
RLAEVCAVLLRLGDELEMIR,   (SEQ ID NO: 127)

wherein the polypeptide selectively binds Bfl-1 over MCL-1;
wherein at least two amino acids in each amino acid sequence are substituted by non-natural amino acids with olefinic side chains,
wherein at least one cysteine if present in the polypeptide is optionally replaced by serine, and wherein at least one methionine if present in the polypeptide is optionally replaced by norleucine; and
wherein the polypeptide comprises a non-natural amino acid bearing an electrophilic group or a non-amino acid warhead at the N-terminus-of the amino acid sequence.

28. A polypeptide that binds to Bfl-1, the polypeptide comprising an amino acid sequence that is at least 70% identical to the Bfl-1 interacting alpha-helical face of the amino acid sequence set forth in SEQ ID N: 22-36, 41-119, 184, 186, 195, 197, or 208, wherein the polypeptide comprises a non-natural amino acid bearing an electrophilic group or a non-amino acid warhead at the N-terminus in of the amino acid sequence.

29. A pharmaceutical composition comprising the polypeptide of claim 28, and a pharmaceutically acceptable carrier.

30. A method for treating a human subject suffering from a cancer that exhibits expression of BFL-1 or dependency on BFL-1, the method comprising administering to human subject therapeutically effective amount of the pharmaceutical composition of claim 29.

31. A method for treating a human subject suffering from a cancer that exhibits expression of BFL-1 or dependency on BFL-1, the method comprising administering to the human subject a therapeutically effective amount of the polypeptide of claim 28.

32. The method of claim 31, wherein a biological sample comprising a tumor from the human subject is or has previously been determined to express Bfl-1.

33. The polypeptide of claim 28, wherein the poly comprises an amino acid sequence that is at least 90% identical to the Bfl-1 interacting alpha-helical face of the amino acid sequence set forth in SEQ ID NO: 62, wherein the polypeptide comprises a non-natural amino acid bearing an electrophilic group or a non-amino acid warhead at the N-terminus of the amino acid sequence.

34. The polypeptide of claim 33, which is stapled.

35. A pharmaceutical composition comprising the polypeptide of claim 34 and a pharmaceutically acceptable carrier.

36. A method for treating a human subject suffering from a cancer that exhibits expression of BFL-1 or dependency on BFL-1, the method comprising administering a therapeutically effective amount of the polypeptide of claim 34 to the human subject.

37. The polypeptide of claim 28, which is stapled.

38. A pharmaceutical composition comprising the polypeptide of claim 37 and a pharmaceutically acceptable carrier.

39. A method for treating a human subject suffering from a cancer that exhibits expression of BFL-1 or dependency on BFL-1, the method comprising administering a therapeutically effective amount of the polypeptide of claim 37 to the human subject.

40. The polypeptide of claim 28, wherein the polypeptide comprises the amino acid sequence of:

(i)
JEVESATQLRXFGDXLNFRQKLL;   (SEQ ID NO: 24)
or (ii)
JIAQELRXIGDXFNAYYARR;   (SEQ ID NO: 30)

wherein J is a non-natural electrophile containing amino acid or an electrophilic warhead that does not comprise an amino acid, and each X is a non-natural amino acid with an olefinic side chain.

41. The polypeptide of claim 40, wherein the non-natural amino acid bearing an electrophilic group or the electrophilic warhead at the N-terminus of the amino acid sequence is (R)-1-acryloylpiperidine-3-carboxamide.

42. A method for treating a human subject suffering from a cancer that exhibits expression of BFL-1 or dependency on BFL-1, the method comprising administering a therapeutically effective amount of the polypeptide of claim 41 to the human subject.

43. A pharmaceutical composition comprising the polypeptide of claim 41, and a pharmaceutically acceptable carrier.

44. The polypeptide of claim 28, wherein the polypeptide comprises: (S)-1-acryloylpyrrolidine-3-carboxamide-EVESATQLRXFGDXLNFRQKLLK (SEQ ID NO: 184), 1-acryloylpiperidine-4-carboxamide-EVESATQLRXFGDXLNFRQKLLK (SEQ ID NO: 184), (R)-1-acryloylpiperidine-3-carboxamide-EVESATQLRXFGDXLNFRQKLL (SEQ ID NO: 186), (R)-1-acryloylpiperidine-3-carboxamide-EVESATQLRXFGDXLNFRQKLL (SEQ ID NO: 186)-Lys(biotin), (S)-1-acryloylpiperidine-3-carboxamide-EVESATQLRXFGDXLNFRQKLLK (SEQ ID NO: 184), (S)-1-acryloylpyrrolidine-2-carboxamide-EVESATQLRXFGDXLNFRQKLLK (SEQ ID NO: 184), (R)-1-acryloylpyrrolidine-2-carboxamide-EVESATQLRXFGDXLNFRQKLLK (SEQ ID NO: 184), (E)-4-(dimethylamino)but-2-enamide-EVESATQLRXFGDXLNFRQKLLK (SEQ ID NO: 184), or acrylamide-EVESATQLRXFGDXLNFRQKLLK (SEQ ID NO: 184), wherein X indicates non-natural amino acids that are joined by an intramolecular cross-link.

45. The polypeptide of claim 28, wherein polypeptide comprises an amino acid sequence that is at least 90% identical to the Bfl-1 interacting alpha-helical face of the amino acid sequence set forth in SEQ ID NO: 22-36, 41-119, 184, 186, 195, 197, or 208, wherein the polypeptide comprises a non-natural amino acid bearing an electrophilic group or a non-amino acid warhead at the N-terminus of the amino acid sequence.

46. The polypeptide of claim 28, wherein polypeptide comprises an amino acid sequence that is at least 90% identical to the Bfl-1 interacting alpha-helical face of the amino acid sequence set forth in SEQ ID NO: 62, wherein the polypeptide comprises a non-natural amino acid bearing an electrophilic group or a non-amino acid warhead at the N-terminus of the amino acid sequence.

47. The polypeptide of claim 28, wherein the polypeptide comprises the amino acid sequence of:
(i) JGRQLAXIGDXINR (SEQ ID NO:72)
(ii) JGR8LAIIGDXINR (SEQ ID NO:79)
(iii) JVGRQLAXIGDXINR (SEQ ID NO:89)
(iv) JVGR8LAIIGDXINR (SEQ ID NO:96)
(v) JLSESLKXIGDXLDS (SEQ ID NO:107); or
(vi) JLSE8LKRIGDXLDS (SEQ ID NO:115);
wherein J is a non-natural electrophile containing amino acid or an electrophilic warhead that does not comprise an amino acid, each X is a non-natural amino acid with olefinic side chain, and 8 is R-octenyl alanine.

48. The polypeptide of claim 47, wherein the polypeptide is stapled and each X is S-pentenyl-alanine.

49. A polypeptide that binds to Bfl-1, the polypeptide comprising the amino acid sequence JAT8LRR- FGDXLN-FRQ (SEQ ID NO:62) with 0 to 5 amino acid substitutions relative to the amino acid sequence of SEQ ID NO:62, wherein J is a non-natural electrophile containing amino acid or an electrophilic warhead that does not comprise an amino acid at the N-terminus of the amino acid sequence, 8 is R-octenyl alanine, and X is a non-natural amino acid with an olefinic side chain.

50. The polypeptide of claim 49, wherein the polypeptide is stapled.

51. A pharmaceutical composition comprising the polypeptide of claim 50 and a pharmaceutically acceptable carrier.

52. A method for treating a human subject suffering from a cancer that exhibits expression of BFL-1 or dependency on BFL-1, the method comprising administering a therapeutically effective amount of the polypeptide of claim 50 to the human subject.

53. The polypeptide of claim 49, wherein X is S-pentenyl alanine.

54. The polypeptide of claim 53, wherein the polypeptide is stapled, and wherein the R-octenyl alanine is linked to the S-pentenyl alanine.

55. The polypeptide of claim 49, wherein the polypeptide comprises the amino acid sequence JAT8LRR- FGDXLN-FRQ (SEQ ID NO:62) with 1 to 5 amino acid substitutions relative to the amino acid sequence of SEQ ID NO:62, wherein J is a non-natural electrophile containing amino acid or an electrophilic warhead that does not comprise an amino acid at the N-terminus of the amino acid sequence, 8 is R-octenyl alanine, and X is a non-natural amino acid with an olefinic side chain.

56. The polypeptide of claim 55, wherein the polypeptide is stapled, wherein X is S-pentenyl alanine, and wherein the R-octenyl alanine is linked to the S-pentenyl alanine.

57. A pharmaceutical composition comprising the polypeptide of claim 56 and a pharmaceutically acceptable carrier.

58. A method for treating a human subject suffering from a cancer that exhibits expression of BFL-1 or dependency on BFL-1, the method comprising administering a therapeutically effective amount of the polypeptide of claim 56 to the human subject.

59. The polypeptide of claim 56, wherein J is (S)-1-acryloylpyrrolidine-3-carboxamide, 1-acryloylpiperidine-4-carboxamide, (R)-1-acryloylpiperidine-3-carboxamide, (S)-1-acryloylpiperidine-3-carboxamide, (S)-1-acryloylpyrrolidine-2-carboxamide, (R)-1-acryloylpyrrolidine-2-carboxamide, (E)-4-(dimethylamino)but-2-enamide, or acrylamide.

60. The polypeptide of claim 56, wherein J is (R)-1-acryloylpiperidine-3-carboxamide.

61. A method for treating a human subject suffering from a cancer that exhibits expression of BFL-1 or dependency on BFL-1, the method comprising administering a therapeutically effective amount of the polypeptide of claim 60 to the human subject.

62. A pharmaceutical composition comprising the polypeptide of claim 60, and a pharmaceutically acceptable carrier.

63. The polypeptide of claim 49, wherein the polypeptide comprises the amino acid sequence JAT8LRRF- GDXLN-FRQ (SEQ ID NO:62) with 1 or 2 amino acid substitutions relative to the amino acid sequence of SEQ ID NO:62, wherein J is a non-natural electrophile containing amino acid or an electrophilic warhead that does not comprise an amino acid at the N-terminus of the amino acid sequence, 8 is R-octenyl alanine, and X is a non-natural amino acid with an olefinic side chain.

64. The polypeptide of claim 63, wherein the polypeptide is stapled, wherein X is S-pentenyl alanine, and wherein the R-octenyl alanine is linked to the S-pentenyl alanine.

65. A pharmaceutical composition comprising the polypeptide of claim 64 and a pharmaceutically acceptable carrier.

66. A method for treating a human subject suffering from a cancer that exhibits expression of BFL-1 or dependency on BFL-1, the method comprising administering a therapeutically effective amount of the polypeptide of claim 64 to the human subject.

67. The polypeptide of claim 64, wherein J is (S)-1-acryloylpyrrolidine-3-carboxamide, 1-acryloylpiperidine-4-carboxamide, (R)-1-acryloylpiperidine-3-carboxamide, (S)-1-acryloylpiperidine-3-carboxamide, (S)-1-acryloylpyrrolidine-2-carboxamide, (R)-1-acryloylpyrrolidine-2-carboxamide, (E)-4-(dimethylamino)but-2-enamide, or acrylamide.

68. The polypeptide of claim 64, wherein J is (R)-1-acryloylpiperidine-3-carboxamide.

69. A method for treating a human subject suffering from a cancer that exhibits expression of BFL-1 or dependency on BFL-1, the method comprising administering a therapeutically effective amount of the polypeptide of claim 68 to the human subject.

70. A pharmaceutical composition comprising the polypeptide of claim 68, and a pharmaceutically acceptable carrier.

71. The polypeptide of claim 49, wherein the polypeptide comprises the amino acid sequence JAT8LRRFG- DXLN-FRQ (SEQ ID NO:62), wherein J is a non-natural electrophile containing amino acid or an electrophilic warhead that does not comprise an amino acid at the N-terminus of the amino acid sequence, 8 is R-octenyl alanine, and X is a non-natural amino acid with an olefinic side chain.

72. A polypeptide that binds to Bfl-1, the polypeptide comprising an amino acid sequence that is at least 70% identical to the Bfl-1 interacting alpha-helical face of the amino acid sequence set forth in SEQ ID NO: 131, wherein the polypeptide selectively binds Bfl-1 over MCL-1; wherein at least two amino acids in the amino acid sequence are substituted by non-natural amino acids with olefinic side chains, wherein the at least two amino acids are separated by three or six amino acids, and wherein the polypeptide comprises a non-natural amino acid bearing an electrophilic group at the N-terminus of the amino acid sequence.

73. The polypeptide of claim 72, which is stapled.

74. A pharmaceutical composition comprising the polypeptide of claim 73 and a pharmaceutically acceptable carrier.

75. A method for treating a human subject suffering from a cancer that exhibits expression of BFL-1 or dependency on BFL-1, the method comprising administering a therapeutically effective amount of the polypeptide of claim 73 to the human subject.

76. The polypeptide of claim 72, wherein the polypeptide comprises an amino acid sequence that is at least 90% identical to the Bfl-1 interacting alpha-helical face of the amino acid sequence set forth in SEQ ID NO: 131, wherein the polypeptide selectively binds Bfl-1 over MCL-1; wherein at least two amino acids in the amino acid sequence are substituted by non-natural amino acids with olefinic side chains, wherein the at least two amino acids are separated by three or six amino acids, and wherein the polypeptide comprises a non-natural amino acid bearing an electrophilic group at the N-terminus of the amino acid sequence.

* * * * *

UNITED STATES PATENT AND TRADEMARK OFFICE
CERTIFICATE OF CORRECTION

| | |
|---|---|
| PATENT NO. | : 11,078,246 B2 |
| APPLICATION NO. | : 15/752358 |
| DATED | : August 3, 2021 |
| INVENTOR(S) | : Loren D. Walensky and Gregory H. Bird |

It is certified that error appears in the above-identified patent and that said Letters Patent is hereby corrected as shown below:

On the Title Page

Column 2, Line 5 [Other Publications]:
Delete "applicat6ion" and insert -- application --, therefor.

In the Claims

Column 173, Line 61, in Claim 1:
Delete "bearings" and insert -- bearing --, therefor.

Column 174, Line 21, in Claim 6:
Delete "NQ:" and insert -- NO: --, therefor.

Column 174, Line 38, in Claim 8:
Delete "NQ:" and insert -- NO: --, therefor.

Column 177, Line 38, in Claim 27:
Delete "N-terminus-of" and insert -- N-terminus of --, therefor.

Column 177, Line 42, in Claim 28:
Delete "N:" and insert -- NO: --, therefor.

Column 177, Line 45, in Claim 28:
After "N-terminus" delete "in".

Column 177, Line 52, in Claim 30:
After "to" insert -- the --.

Column 177, Line 53, in Claim 30:
After "subject" insert -- a --.

Signed and Sealed this
Tenth Day of January, 2023

Katherine Kelly Vidal
*Director of the United States Patent and Trademark Office*

CERTIFICATE OF CORRECTION (continued)
U.S. Pat. No. 11,078,246 B2

Column 177, Line 63, in Claim 33:
Delete "poly" and insert -- polypeptide --, therefor.

Column 178, Line 32, in Claim 40:
Delete "JIAQELRXIGDXFNAYYARR;" and insert -- JIAQELRXIGDXFNAYYARR, --, therefor.

Column 178, Lines 63-64, in Claim 44:
Delete "EVES ATQLRXFGDXLNFRQKLLK" and insert -- EVESATQLRXFGDXLNFRQKLLK --, therefor.

Column 179, Lines 32-33, in Claim 49:
Delete "JAT8LRR- FGDXLNFRQ" and insert -- JAT8LRRFGDXLNFRQ --, therefor.

Column 179, Lines 57-58, in Claim 55:
Delete "JAT8LRR- FGDXLNFRQ" and insert -- JAT8LRRFGDXLNFRQ --, therefor.

Column 180, Lines 27-28, in Claim 63:
Delete "JAT8LRRF- GDXLNFRQ" and insert -- JAT8LRRFGDXLNFRQ --, therefor.

Column 180, Lines 64-65, in Claim 71:
Delete "JAT8LRRFG- DXLNFRQ" and insert -- JAT8LRRFGDXLNFRQ --, therefor.